US008624034B2

(12) United States Patent
Reilly et al.

(10) Patent No.: US 8,624,034 B2
(45) Date of Patent: *Jan. 7, 2014

(54) FLUORO-PYRIDINONE DERIVATIVES USEFUL AS ANTIBACTERIAL AGENTS

(75) Inventors: Usa Reilly, West Haven, CT (US); Michael Melnick, Portage, MI (US); Matthew F. Brown, Stonington, CT (US); Mark S. Plummer, Westbrook, CT (US); Justin Montgomery, Ledyard, CT (US); Ye Che, Groton, CT (US); Loren Price, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/414,057

(22) Filed: Mar. 7, 2012

(65) Prior Publication Data

US 2012/0232083 A1    Sep. 13, 2012

Related U.S. Application Data

(60) Provisional application No. 61/449,825, filed on Mar. 7, 2011.

(51) Int. Cl.
*A61K 31/44* (2006.01)
*C07D 211/72* (2006.01)

(52) U.S. Cl.
USPC .......................................... 546/290; 514/341

(58) Field of Classification Search
None
See application file for complete search history.

(56) References Cited

U.S. PATENT DOCUMENTS

| | | | |
|---|---|---|---|
| 4,769,461 | A | 9/1988 | Musser et al. |
| 5,110,831 | A | 5/1992 | Magolda et al. |
| 6,673,965 | B1 | 1/2004 | Ward et al. |
| 2005/0119305 | A1 | 6/2005 | Naka et al. |
| 2006/0247271 | A1 | 11/2006 | Bruton |
| 2006/0276409 | A1 | 12/2006 | Hunter et al. |
| 2008/0085893 | A1 | 4/2008 | Yang et al. |
| 2008/0234297 | A1 | 9/2008 | Qian et al. |
| 2011/0178042 | A1 | 7/2011 | Brown et al. |
| 2012/0232083 | A1 | 9/2012 | Reilly et al. |
| 2012/0258948 | A1 | 10/2012 | Brown et al. |

FOREIGN PATENT DOCUMENTS

| | | |
|---|---|---|
| EP | 1437349 | 7/2004 |
| WO | 0130747 | 5/2001 |
| WO | 2004062601 | 7/2004 |
| WO | 2004067502 | 8/2004 |
| WO | 2006063281 | 6/2006 |
| WO | 2006118155 | 11/2006 |
| WO | 2006124897 | 11/2006 |
| WO | WO 2007 069020 | 6/2007 |
| WO | 2008045671 | 4/2008 |
| WO | 2008105515 | 9/2008 |
| WO | 2008115262 | 9/2008 |
| WO | 2009008905 | 1/2009 |
| WO | WO 2010 017060 | 2/2010 ........... C07D 207/06 |
| WO | 2010024356 | 3/2010 |
| WO | 2010031750 | 3/2010 |
| WO | 2010032147 | 3/2010 |
| WO | 2010100475 | 9/2010 |
| WO | WO 2011 073845 | 6/2011 |
| WO | 2012120397 | 9/2012 |
| WO | 2012137094 | 10/2012 |
| WO | 2012137099 | 10/2012 |

OTHER PUBLICATIONS

PCT/IB2012/050812 International Search Report and Written Opinion mailed Apr. 23, 2012, 4 pages.
Rice, Louis B., "Unmet medical needs in antibacterial therapy", Biochemical Pharmacology, Mar. 30, 2006, pp. 991-995, 71(7).
Raetz, C.R.H., et al., "Lipid a Modification Systems in Gram-Negative Bacteria", Annual Review Biochemistry 2007, pp. 295-329, vol. 76.
Gipstein, E., et al., "Synthesis and Polymerization of alkyl α-(Alkylsulfonyl)acrylates[1a]", Journal of Organic Chemistry, 1980, pp. 1486-1489, 45(8).
Machine Translation of WO 2010/024356 published Mar. 4, 2010.
"455710(Antibiotics and Antibacterial Drugs)", Annual Drug Data Report, Jan. 1, 2007, p. 629, 29(7).
Barlaam, B., et al., "New Alpha-Substituted Succinate-Based Hydroxamic Acids As TNFALPHA Convertase Inhibitors", Journal of Medicinal Chemistry, Jan. 1, 1999, pp. 4890-4908, 42(23).
Clements, J.M., et al., "Antimicrobial Activities and Characterization of Novel Inhibitors of LpxC", Antimicrobial Agents and Chemotherapy, American Society for Microbiology, Jun. 1, 2002, pp. 1793-1799, 46(6).
Conreaux, D., et al., "A practical procedure for the selective N-alkylation of 4-alkoxy-2-pyridones and its use in a sulfone-mediated synthesis of N-methyl-4-methoxy-2-pyridone", Tetrahedron Letters, 2005, pp. 7917-7920, 46(46).
Dube, Peter H., et al., "Protective Role of Interleukin-6 During *Yersinia enterocolitica* Infection Is Mediated through the Modulation of Inflammatory Cytokines", Infection and Immunity, Jun. 2004, pp. 3561-3570, 72(6).
English Translation of International Patent Application WO 2008/105515 publication date Sep. 4, 2008.
Gennadios, H., et al., "Mechanistic Inferences from the Binding of Ligands to LpxC, a Metal-Dependent Deacetylase", Biochemistry, 2006, pp. 7940-7948, 45(26).
Gipstein, E., et al., "Synthesis and Polymerization of alkyl α-(Alkylsulfonyl)acrylates1a", Journal of Organic Chemistry, 1980, pp. 1486-1489, 45(8).
Hennigan, Stephanie, et al., "Interleukin-6 Inhibitors in the Treatment of Rheumatoid Arthritis", Therapeutics and Clinical Risk Management, 2008, pp. 767-775, 4(4).
Imanishi, Jiro, "Expression of Cytokines in Bacterial and Viral Infections and Their Biochemical Aspects", The Japanese Biochemical Society, 2000, pp. 525-530, 127(4).

(Continued)

*Primary Examiner* — Janet L Andres
*Assistant Examiner* — Heidi Reese
(74) *Attorney, Agent, or Firm* — John A. Wichtowski

(57) ABSTRACT

The present invention is directed to a new class of hydroxamic acid derivatives, their use as LpxC inhibitors and, more specifically, their use to treat bacterial infections.

11 Claims, No Drawings

(56) References Cited

OTHER PUBLICATIONS

International Patent Application No. PCT/IB2010/055596, publication No. WO 2011/073845, Search Report and Written Opinion mailed Mar. 23, 2011, 15 pages.

IUPAC, E.D., et al., "alkyl groups", Compendium of Chemical Terminology: IUPAC Recommendations; http://www.iupac.org/goldbook/A00228.pdf Jan. 1, 1997.

Kirsch, P., et al., "Super-Fluorinated Liquid Crystals: Towards the Limits of Polarity", European Journal Organic Chemistry, Jul. 2008, pp. 3479-3487, 2008(20).

Kwok, A., et al., "*Helicobacter pylori* eradication therapy: indications, efficacy and safety", Expert Opinion Drug Safety, May 2008, pp. 271-281, 7(3).

International Patent Application No. PCT/IB2009/053809, PCT International Search Report (ISR), mailed Apr. 4, 2010, 7 pages.

International Patent Application No. PCT/IB2009/053809, PCT International Written Opinion, mailed Apr. 4, 2010, 7 pages.

Product Label—ACTEMRA* (toclizumab) Injection, for intravenous infusion; revised Apr. 2013, pp. 1-35.

Qu, W., et al., "Quick Assembly of 1,4-Diphenyltriazoles as Probes Targeting β-Amyloid Aggregates in Alzheimer's Disease", Journal of Medicinal Chemistry, 2007, pp. 3380-3387, 50(14).

Wang, Y., et al., "A novel and efficient synthesis of terminal arylacetylenes via Sonogashira coupling reactions catalysed by MCM-41-supported bidentate phosphine palladium (0) complex", Journal of Chemical Research, Dec. 2007, pp. 728-732, 2007(12).

Apfel, Christian et al., "Hydroxamic Acid Derivatives as Potent Peptide Deformylase Inhibitors and Antibacterial Agents", Journal of Medicinal Medicinal Chemistry, Jun. 15, 2000, pp. 2324-2331, 43(12).

Brown, Matthew F., et al., "Potent Inhibitors of LpxC for the Treatment of Gram-Negative Infections", Journal of Medicinal Chemistry, Dec. 18, 2011, pp. 914-923, 55(18).

International Patent Application No. PCT/IB2012/051406 PCT International Search Report (ISR) and Written Opinion mailed Oct. 7, 2012, 5 pages.

FLUORO-PYRIDINONE DERIVATIVES USEFUL AS ANTIBACTERIAL AGENTS

FIELD OF THE INVENTION

This invention relates to novel hydroxamic acid derivatives. The invention also relates to methods of using such compounds in the treatment of bacterial infections (especially Gram-negative infections) and to pharmaceutical compositions containing such compounds.

BACKGROUND OF THE INVENTION

Infection by Gram-negative bacteria such as *Pseudomonas aeruginosa*, Extended Spectrum β-lactamase producing (ESBL) Entgerobacteriaceae, and *Acinetobacter baumannii* is a major health problem, especially in the case of hospital-acquired infections. In addition, there is an increasing level of resistance to current antibiotic therapies, which severely limits treatment options. For example, in 2002, 33% of *Pseudomonas aeruginosa* infections from intensive care units were resistant to fluoroquinolones, while resistance to imipenem was 22% (CID 42: 657-68, 2006). In addition, multi-drug resistant (MDR) infections are also increasing; in the case of *Pseudomonas aeruginosa*, MDR increased from 4% in 1992 to 14% in 2002 (Biochem Pharm 71: 991, 2006).

Gram-negative bacteria are unique in that their outer membrane contains lipopolysaccharide (LPS), which is crucial for maintaining membrane integrity, and is essential for bacterial viability (reviewed in Ann. Rev. Biochem 76: 295-329, 2007). The major lipid component of LPS is Lipid A, and inhibition of Lipid A biosynthesis is lethal to bacteria. Lipid A is synthesized on the cytoplasmic surface of the bacterial inner membrane via a pathway that consists of nine different enzymes. These enzymes are highly conserved in most Gram-negative bacteria. LpxC [UDP-3-O—(R-3-hydroxymyristoyl)-N-acetylglucosamine deacetylase] is the enzyme that catalyzes the first committed step in the Lipid A biosynthetic pathway, the removal of the N-acetyl group of UDP-3-O—(R-3-hydroxymyristoyl)-N-acetylglucosamine. LpxC is a $Zn^{2+}$-dependent enzyme that has no mammalian homologue, making it a good target for the development of novel antibiotics. Several inhibitors of LpxC with low nM affinity have been reported (Biochemistry 45: 7940-48, 2006).

SUMMARY OF THE INVENTION

A new class of LpxC inhibitors has been discovered. These compounds, or their pharmaceutically acceptable salts, can be represented by Formula I below:

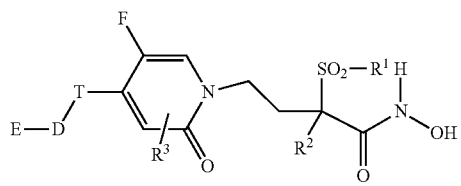

I in which:

$R^1$ is represented by $C_1$-$C_3$ alkyl;

$R^2$ is represented by hydrogen or $C_1$-$C_3$ alkyl;

$R^3$ is represented by hydrogen, halogen, hydroxy, cyano, $C_1$-$C_3$ alkyl, $C_1$-$C_3$ alkoxy, trifluoromethyl or trifluoromethoxy;

T is represented by ethynyl, optionally substituted ($C_6$-$C_{10}$) aryl or optionally substituted heteroaryl;

D is absent, or is represented by —$(CH_2)_r$—, —$(CH_2)_n$—O—$(CH_2)_p$—, or a bond;

r is represented by the integer 1, 2, or 3;

n and p are each independently represented by the integer 0, 1, or 2;

E is absent, or is represented by a substituent selected from the group consisting of:
  i) ($C_3$-$C_{10}$)cycloalkyl, optionally substituted;
  ii) ($C_6$-$C_{10}$)aryl optionally substituted;
  iii) heteroaryl, optionally substituted; and
  iv) heterocyclic, optionally substituted;
with the proviso that:
  1) if E is absent, then D is also absent;
  2) T is not represented by unsubstituted phenyl; when E and D both are absent, $R^3$ is hydrogen and $R^1$ and $R^2$ are each methyl.

The compounds of Formula I exhibit antibacterial activity, especially against Gram-negative organisms. They may be used to treat bacterial infections in mammals, especially humans. The compounds may also be used for veterinary applications, such as treating infections in livestock and companion animals.

The compounds of Formula I are useful for treating a variety of infections; especially Gram-negative infections including nosocomial pneumonia, urinary tract infections, systemic infections (bacteremia and sepsis), skin and soft tissue infections, surgical infections, intraabdominal infections, lung infections (including those in patients with cystic fibrosis), *Helicobacter pylori* (and relief of associated gastric complications such as peptic ulcer disease, gastric carcinogenesis, etc.), endocarditis, diabetic foot infections, osteomyelitis, and central nervous system infections.

In order to simplify administration, the compounds will typically be admixed with at least one excipient and formulated into a pharmaceutical dosage form. Examples of such dosage forms include tablets, capsules, solutions/suspensions for injection, aerosols for inhalation, cream/ointments for topical, otic or ophthalmic use, and solutions/suspensions for oral ingestion.

DETAILED DESCRIPTION OF THE INVENTION

The headings within this document are only being utilized to expedite its review by the reader. They should not be construed as limiting the invention or claims in any manner.

DEFINITIONS AND EXEMPLIFICATION

As used throughout this application, including the claims, the following terms have the meanings defined below, unless specifically indicated otherwise. The plural and singular should be treated as interchangeable, other than the indication of number:

a. "$C_1$-$C_3$ alkyl" refers to a branched or straight chained alkyl group containing from 1 to 3 carbon atoms, such as methyl, ethyl, n-propyl, or isopropyl, etc.

b. "$C_1$-$C_3$ alkoxy" refers to a straight or branched chain alkoxy group containing from 1 to 3 carbon atoms, such as methoxy, ethoxy, n-propoxy, isopropoxy, etc.

c. "halogen" refers to a chlorine, fluorine, iodine, or bromine atom.

d. "$C_1$-$C_6$ alkyl" refers to a branched or straight chained alkyl group containing from 1 to 6 carbon atoms, such as methyl, ethyl, n-propyl, isopropyl, n-butyl, isobutyl, pentyl, etc.

e. "$C_1$-$C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 3 hydrogen atoms are replaced by a substituent selected from the group consisting of halogen, cyano, sulfonamide, imino, —$OR^4$, —$SR^4$, and —$NR^4R^5$ in which $R^4$ and $R^5$ are each independently represented by hydrogen or $C_1$-$C_3$ alkyl.

f. "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc.

g. "$C_1$-$C_6$ alkoxy, optionally substituted" refers to a straight or branched chain alkoxy group containing from 1 to 6 carbon atoms, such as methoxy, ethoxy, n-propoxy, isopropoxy, n-butoxy, isobutoxy, pentoxy, etc. Such an alkoxy group may be optionally substituted, in which up to 3 hydrogen atoms are replaced by a substituent selected from the group consisting of halogen, cyano, sulfonamide, imino, —$OR^4$, —$SR^4$, and —$NR^4R^5$ in which $R^4$ and $R^5$ are each independently represented by hydrogen or $C_1$-$C_3$ alkyl.

h. "($C_6$-$C_{10}$)aryl" means a cyclic, aromatic hydrocarbon containing from 6 to 10 carbon atoms. Examples of such aryl groups include phenyl, naphthyl, etc.

i. "($C_6$-$C_{10}$)aryl optionally substituted" means a cyclic, aromatic hydrocarbon as defined above. Such an aryl moiety may be optionally substituted with up to 4 non-hydrogen substituents, each substituent is independently selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, phosphate, —$SO_2NR^4R^5$, —$(CH_2)_m$—$NR^5$—$C(O)$—$R^4$, —$(CH_2)_m$—$C(O)$—$N$—$R^4R^5$, —$C(O)$—$R^4$, —$C(O)$—$O$—$R^4$, —$SR^4$, —$SO_2R^4$ and —$NR^4R^5$, in which m, $R^4$ and $R^5$ are as defined above and each M independently represents an integer from 0-4. These substituents may be the same or different and may be located at any position of the ring, that is chemically permissible. "Phenyl optionally substituted" refers to a phenyl ring substituted as described above.

j. "heteroaryl" refers to an aromatic ring having one, or more, heteroatoms selected from oxygen, nitrogen and sulfur. More specifically, it refers to a 5- or 6-membered ring containing 1, 2, 3, or 4 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. The 5-membered ring has 2 double bonds and the 6-membered ring has 3 double bonds ("hereinafter a "5- to 6-membered heteroaryl"). The term "heteroaryl" also includes bicyclic groups in which the heteroaryl ring is fused to a benzene ring, heterocyclic ring, a cycloalkyl ring, or another heteroaryl ring. Examples of such heteroaryl ring systems include, but are not limited to, pyrrolyl, furanyl, thienyl, imidazolyl, oxazolyl, indolyl, thiazolyl, pyrazolyl, pyridinyl, pyrimidinyl, purinyl, quinolinyl, benzofuran, tetrazole, isoquinolinyl, oxadiazolyl, thiadiazolyl, isothiazolyl, isoxazolyl, triazolyl, benzo[b]thienyl, 2-, 4-, 5-, 6-, or 7-benzoxazolyl, 7-benzimidazolyl, or benzothiazolyl.

k. "heteroaryl, optionally substituted," refers to a heteroaryl moiety as defined immediately above, in which up to 4 carbon atoms of the heteroaryl moiety may be substituted with a substituent, each substituent is independently selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, phosphate, —$SO_2NR^4R^5$, —$(CH_2)_m$—$N$—$C(O)$—$R^4$, —$(CH_2)_m$—$C(O)$—$N$—$R^4R^5$, —$C(O)$—$R^4$, —$C(O)$—$O$—$R^4$, —$SR^4$, —$SO_2R^4$ and —$NR^4R^5$, in which m, $R^4$ and $R^5$ are as defined above. These substituents may be the same or different and may be located at any position of the ring, that is chemically permissible.

Any reference to an "optionally substituted 5- to 6-membered heteroaryl" refers to 5- to 6-membered heteroaryl ring as described in definition j, having the substitution pattern described immediately above.

l. "($C_3$-$C_{10}$) cycloalkyl" refers to a saturated or partially saturated monocyclic, bicyclic, bridged bicyclic or tricyclic alkyl radical wherein each cyclic moiety has 3 to 10 carbon atoms. Examples of such cycloalkyl radicals include cyclopropyl, cyclobutyl, cyclopentyl, cyclohexyl, cyclooctyl, and the like.

m. "($C_3$-$C_{10}$) cycloalkyl" optionally substituted refers to a ($C_3$-$C_{10}$) cycloalkyl moiety as described above. Such a cycloalkyl group may be optionally substituted, in which up to 4 hydrogen atoms are replaced by a substituent selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, phosphate, oxo, —$SO_2NR^4R^5$, —$(CH_2)_m$—$NR^5$—$C(O)$—$R^4$, —$(CH_2)_m$—$C(O)$—$N$—$R^4R^5$, —$C(O)$—$R^4$, —$C(O)$—$O$—$R^4$, —$SR^4$, —$SO_2R^4$ and —$NR^4R^5$, in which M, $R^4$ and $R^5$ are as defined above. These substituents may be the same or different and may be located at any position of the ring, that is chemically permissible.

n. "($C_3$-$C_6$) cycloalkyl" refers to a cyclopropyl, cyclobutyl, cyclopentyl or cyclohexyl moiety, any of which may be optionally substituted as described above, if chemically permissible.

o. "heterocycle" or "heterocyclic ring" refers to any 3- or 4-membered ring containing a heteroatom selected from oxygen, nitrogen and sulfur; or a 5-, 6-, 7-, 8-, 9-, or 10-membered ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, the 6- and 7-membered rings have 0 to 2 double bonds, and the 8, 9, or 10 membered rings may have 0, 1, 2, or 3 double bonds. The term "heterocyclic" also includes bicyclic groups in which any of the above heterocyclic rings is fused to a benzene ring, a cyclohexane or cyclopentane ring or another heterocyclic ring (for example, indolyl, quinolyl, isoquinolyl, tetrahydroquinolyl, benzofuryl, dihydrobenzofuryl or benzothienyl and the like). Heterocyclics include: pyrrolidinyl, tetrahydrofuranyl, tetrahydrothiophenyl, piperidinyl, piperazinyl, azepane, azocane, morpholinyl, isochromyl, quinolinyl, tetrahydrotriazine, tetrahydropyrazole, dihydro-oxathiol-4-yl, dihydro-1H-isoindole, tetrahydro-oxazolyl, tetrahydro-oxazinyl, thiomorpholinyl, tetrahydropyrimidinyl, dioxolinyl, octahydrobenzofuranyl, octahydrobenzimidazolyl, and octahydrobenzothiazolyl.

p. "heterocyclic, optionally substituted" refers to a heterocyclic moiety as defined immediately above, in which up to 4 carbon atoms of the heterocycle moiety may be substituted with a substituent, each substituent is independently selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, pentafluoro sulfonyl, phosphate, oxo, $SO_2NR^4R^5$, —$(CH_2)_m$—N═C(O)—$R^4$, —$(CH_2)_m$—C(O)—N—$R^4R^5$, —C(O)—$R^4$, —C(O)—O—$R^4$, —$SR^4$, —$SO_2R^4$ and —$NR^4R^5$, in which m, $R^4$ and $R^5$ are as defined above. These substituents may be the same or different and may be located at any position of the ring that is chemically permissible. Any nitrogen atom within such a heterocyclic ring may optionally be substituted with ($C_1$-$C_6$) alkyl, or any other substituent listed above, if such a substitution is chemically permissible. Any sulfur atom in the ring may be further substituted with 1 or 2 oxygen atoms (if such a substitution is chemically permissible).

q. "therapeutically effective amount" refers to an amount of a compound of Formula I that, when administered to a patient, provides the desired effect; i.e., lessening in the severity of the symptoms associated with a bacterial infection, decreasing the number of bacteria in the affected tissue, and/or preventing bacteria in the affected tissue from increasing in number (localized or systemic).

r. "patient" refers to warm blooded animals such as for example, livestock, guinea pigs, mice, rats, gerbils, cats, rabbits, dogs, monkeys, chimpanzees, and humans.

s. "treat" refers to the ability of the compounds to relieve, alleviate or slow the progression of the patient's bacterial infection (or condition) or any tissue damage associated with the disease.

t. "pharmaceutically acceptable" indicates that the substance or composition must be compatible chemically and/or toxicologically, with the other ingredients comprising a formulation, and/or the mammal being treated therewith.

u. "isomer" means "stereoisomer" and "geometric isomer" as defined below.

v. "stereoisomer" means compounds that possess one or more chiral centers and each center may exist in the R or S configuration. Stereoisomers include all diastereomeric, enantiomeric and epimeric forms as well as racemates and mixtures thereof.

w. "geometric isomer" means compounds that may exist in cis, trans, anti, entgegen (E), and zusammen (Z) forms as well as mixtures thereof.

x. Compounds of "Formula I", "formula I", "formula (I)" and "compounds of the invention" are being used interchangeably throughout the application and should be treated as synonyms.

y. The terms "pyridone" and "pyridinone" have been used interchangeably within this application. No difference or distinction is meant, unless otherwise noted. One skilled in the art will readily understand this.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

The invention also relates to base addition salts of the compounds of the invention. The chemical bases that may be used as reagents to prepare these pharmaceutically acceptable base salts are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002). Methods for making pharmaceutically acceptable salts of compounds of the invention are known to one of skill in the art.

Certain of the compounds of the formula (I) may exist as geometric isomers. The compounds of the formula (I) may possess one or more asymmetric centers, thus existing as two or more stereoisomeric forms. The present invention includes all the individual stereoisomers and geometric isomers of the compounds of formula (I) and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of this invention and prodrugs thereof can generally be prepared by carrying out the procedures disclosed in the Schemes and/or in the Examples below, by substituting a readily available isotopically-labeled reagent for a non-isotopically-labeled reagent.

All of the compounds of Formula I contain a sulfonyl moiety as depicted below:

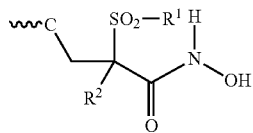

This sulfonyl moiety will always be substituted with a lower alkyl moiety. Typically it will be methyl. The carbon atom adjacent to the sulfonyl may optionally be substituted, as represented by $R^2$. Typically both $R^1$ and $R^2$ will be methyl.

As is readily apparent to one skilled in the art, the carbon adjacent to the sulfonyl moiety is a chiral center. Therefore, the compounds can exist as the racemate, as the S-enantiomer, or as the R-enantiomer. In a further embodiment, the compounds may be prepared and administered as the R-enantiomer, as depicted below:

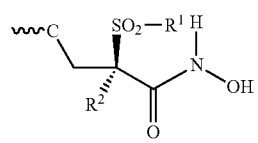

As is readily apparent to one skilled in the art, the compounds as synthesized will rarely be present exclusively as a single enantiomer. The opposite enantiomer (i.e the S-enantiomer) may be present in minor amounts (i.e. "substantially pure"). This minor amount can be up to 10 w/w %, more typically no greater than 5 w/w %, in a further embodiment no greater than 1 w/w %, or more specifically, no greater than 0.5 w/w %.

All of the compounds of Formula I contain a pyridinone moiety as depicted below:

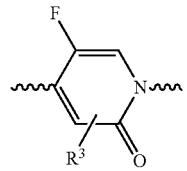

This pyridinone ring will be connected to the rest of the molecule via the 1- and 4-positions as depicted above. Position 3 will always be substituted with a fluoro moiety as depicted above. The pyridinone moiety may be optionally substituted, as depicted by the $R^3$ moiety. $R^3$ may represent one non-hydrogen substituent, as defined above. This non-hydrogen substituent may be located at either position 2 or 5 of the pyridinone ring. Typically $R^3$ will represent hydrogen.

T will always be present in the molecule. It will be represented by ethynyl, aryl or heteroaryl (either ring system may be substituted as defined above.) Typically, T will be represented by phenyl, which may be optionally substituted. When T is heteroaryl, it will be linked to the pyridinone via a carbon-carbon bond (i.e. the heteroatom(s) will not be bonded to the pyridinone). If E is present, and D represents a bond, then it may represent any chemically permissible bond, i.e carbon-carbon, carbon-nitrogen, etc.

The presence of D and E are optional. If present, D will typically be a bond and E will be represented by either a 5- to 6-membered heteroaryl or a ($C_3$-$C_6$) cycloalkyl, either of which may be optionally substituted as defined above.

More specific embodiments of the invention include compounds of Formula I in which:
a) $R^1$ is methyl;
b) $R^2$ is methyl;
c) $R^3$ is hydrogen;
d) the compound is present as the R-enantiomer (i.e. substantially pure);
e) T is phenyl, which may be optionally substituted and D and E are both absent; and
f) T is phenyl, D is a bond and E is either $C_3$-$C_6$ cycloalkyl or a 5- to 6-membered heteroaryl, either of which may be optionally substituted.

A further embodiment of the invention is directed to compounds of Formula I, substantially pure in which:
a) $R^1$ and $R^2$ are each methyl, $R^3$ is hydrogen, and T, D and E are as defined;
b) $R^1$ and $R^2$ are each methyl, $R^3$ is hydrogen, T is optionally substituted phenyl and both E and D are absent;

c) R¹ and R² are each methyl, R³ is hydrogen, T is optionally substituted phenyl, D is a bond and E is a 5- to 6-membered heteroaryl, which may be optionally substituted; and d) R¹ and R² are each methyl, R³ is hydrogen, T is optionally substituted phenyl, D is a bond and E is $C_3$-$C_6$ cycloalkyl, which may be optionally substituted.

In a further embodiment, the invention is directed to a subgenus represented by formula Ia below, in which the molecule is present as the R-enantiomer (i.e. the S-enantiomer may optionally be present in minor amounts). As depicted below, R¹ and R² are methyl, R³ is hydrogen, both E and D are absent and T is substituted phenyl. More specifically $R^a$ is represented by one or more substituents selected from the group consisting of $C_1$-$C_3$ alkyl, $C_1$-$C_3$ alkoxy, fluorine, chlorine, hydroxy, trifluoromethyl and trifluoromethoxy.

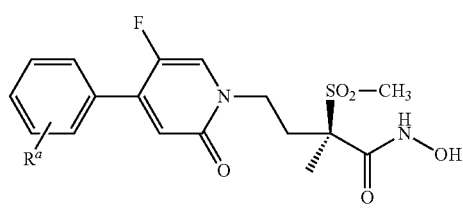

Ia

In a further embodiment, the invention is directed to a subgenus represented by formula Ib below, in which the molecule is present as the R-enantiomer (i.e. the S-enantiomer may optionally be present as a minor impurity). As depicted below, R¹ and R² are methyl, R³ is hydrogen, T is phenyl, D is a bond and E is a 5- to 6-membered heteroaryl, which may be optionally substituted.

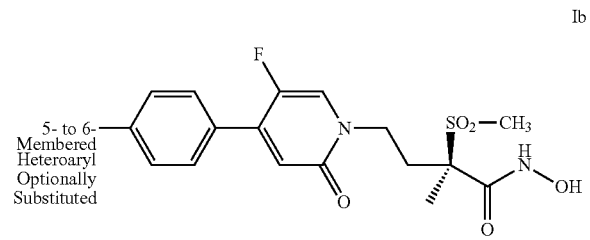

Ib

In a more specific embodiment of the invention, the LpxC inhibitor is the following compound, or its pharmaceutically acceptable salt:

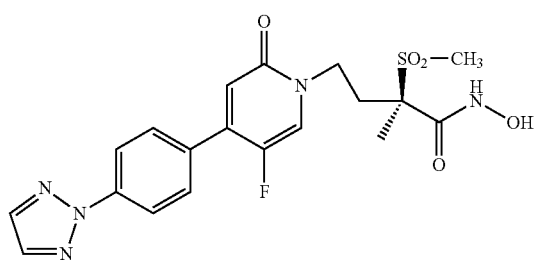

In a more specific embodiment of the invention, the LpxC inhibitor is the following compound, or its pharmaceutically acceptable salt:

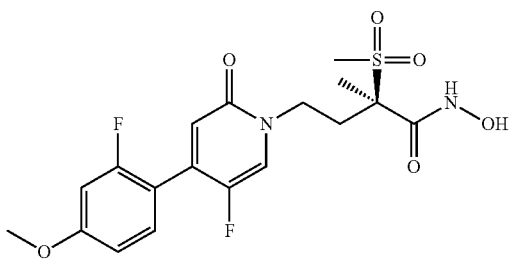 [SMILES: COc1ccc(-c2cc(=O)n(CC[C@](C)(C(=O)NO)S(C)(=O)=O)cc2F)c(F)c1]

Synthesis

The compounds of Formula I can be prepared by a variety of methods that are analogously known in the art. The reaction schemes presented below illustrate two alternative methods for preparing these compounds. Others, including modifications thereof, will be readily apparent to one skilled in the art.

The synthesis of the compounds of Formula I is depicted below in Scheme A. The first step is to carry out the N-alkylation depicted in Step A. The pyridinone of structure 1 is reacted with the sulfonyl derivative of structure 2 generating the intermediate of structure 3. Structure 3 can be further derivatized to generate the compounds of Formula I. Two alternative syntheses are depicted (Option A or B), but the reader will readily note they are variations of the same synthesis. The only difference is the order in which the steps are carried out.

Initially in Option A, the halide, depicted by X, at the 4-position of the pyridinone of structure 3 is displaced by the desired terminal moiety E-D-T-M¹, in which M¹ is a metal species, such as a boron derivative suitable for undergoing a typical cross-coupling such as a Suzuki-Miyaura reaction. Hydrolysis, or removal, of the ethyl protecting group (or other suitable protecting groups) in Step C affords the compound of structure 5. The terminal carboxylic acid of structure 5 is then converted to the protected hydroxamic acid derivative as depicted by structure 8. Deprotection of the protected hydroxamic acid derivative of structure 8, as depicted in Step H, affords the final product of Formula I. While these reactions are well known to one skilled in the art, they are discussed in greater detail below.

Initially, in Option B of Scheme A, the ethyl protecting group (or other conventional protecting groups) is removed from the pyridinone of structure 3 generating the compound of structure 6 as depicted in Step E. In Step F, the terminal carboxylic acid of structure 6 is converted to the protected hydroxamic acid derivative of structure 7 via amidation conditions. In Step G, the halide function at the 4-position on the pyridinone moiety is then directly displaced by the desired terminal moiety, E-D-T-M¹, via a coupling reaction to afford the protected hydroxamic acid derivatives of structure 8. As before, deprotection of the protected hydroxamic acid derivatives, as depicted in Step H, affords the compounds of Formula I.

SCHEME A
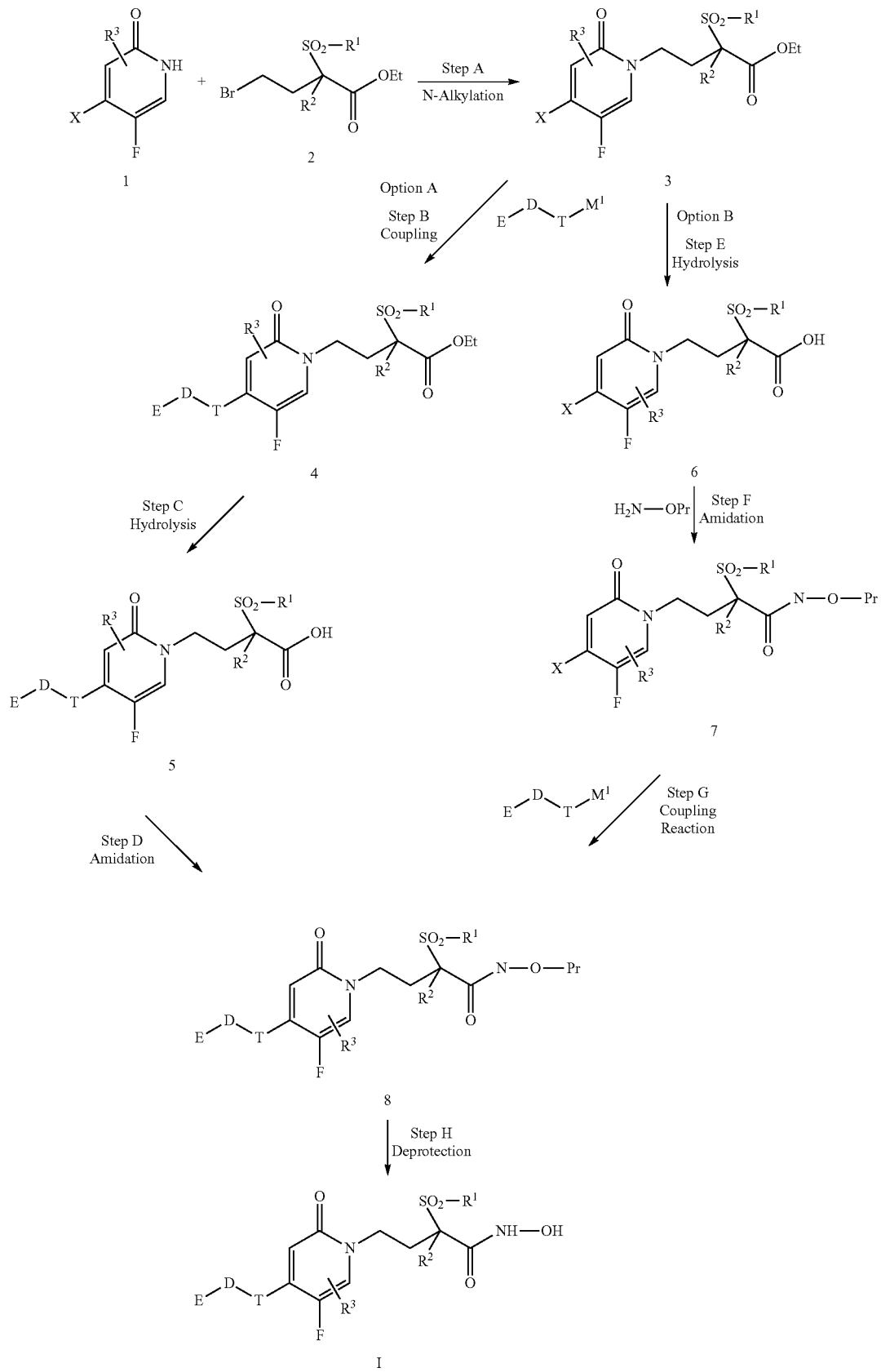

The N-alkylation depicted above in Step A can be carried out using techniques well known to one skilled in the art. One of the starting materials is the 2-pyridinone derivative of structure 1. In this pyridinone, X will represented by a halide and $R^3$ will be represented by the same moiety as is desired in the final product. Many of these pyridinone derivatives are known in the art and the remainder can be produced using synthetic techniques analogously known in the art. The reader's attention is directed to Tet. Lett. (2005) Vol 46, 7917, for a description of such techniques. Preparation 2 infra, also illustrates their preparation.

The other reactant in the N-alkylation depicted in Step A is the protected alkyl sulfonate of structure 2, in which $R^1$ and $R^2$ are represented by the same moiety as is desired in the final product. An ethyl protecting group is portrayed, but any standard protecting group may be substituted. These alkyl sulfonates are also known in the art. The reader's attention is directed to Journal of Organic Chemistry, (1980) Vol 45, 8, 1486-1489 for a description of their preparation. Preparation 1 infra, also illustrates their preparation The N-alkylation can be carried out as is known in the art. Typically, equivalent amounts of the compounds of structure 1 and 2 are contacted in a mixture of aprotic and protic solvents, such as tetrahydrofuran and t-butanol, in the presence of a base such as potassium carbonate, cesium carbonate, sodium carbonate, sodium hydride, etc. A transfer agent, such as tetrabutyl ammonium bromide, can be utilized, if desired. The reactants are typically heated and the reaction is allowed to proceed to completion. The desired product of structure 3 can be isolated by methods known in the art. If desired, the product of structure 3 can be purified, or alternatively the crude can be used in the next step of the reaction. Preparation 2 infra, illustrates such an N-alkylation.

Scheme A illustrates how to incorporate the hydroxamic acid moiety into the molecules. Initially, the protecting group is removed from the carboxylic acid, thereby generating the intermediate of structure 5 and 6, as depicted in Step C (Option A) and Step E (Option B) respectively. The manner in which this is accomplished will vary with the identity of the actual protecting group and is well known to those skilled in the art. The reader's attention is directed to McOmie or Greene supra, for a discussion of potential protecting groups and methods for their removal. Preparation 2 infra describes how to remove an ethyl moiety as depicted in Scheme A.

In Steps F and D, the hydroxamic acid moiety as depicted, is incorporated into the molecule. A protected hydroxylamine source may be used followed by a subsequent deprotection reaction (alternatively, hydroxylamine may be directly incorporated to eliminate the deprotection steps). In either case the hydroxamic acid is incorporated into the molecule using standard amidation reactions. For example, the compound of structure 5 (Option A) or 6 (Option B) may be contacted with an excess of oxalyl chloride, in an aprotic solvent such as dichloromethane for a sufficient period of time to allow the formation of the corresponding acid chloride, followed by the addition of an excess of either hydroxylamine or protected hydroxylamine. The reaction is then allowed to proceed to completion and the protected intermediates of structure 7 (Option B) or 8 (Option A) is isolated from the reaction medium and purified as is known in the art. As mentioned above, any deprotection may be carried out as is known in the art (See Greene or McOmie supra). Alternatively, the amide can be formed using the amide coupling reagent, 1,1'-carbonyldiimidazole (CDI), 2-chloro-4,6-dimethoxy-1,3,5-triazine (CDMT), or 1-ethyl-3-(3-dimethylaminopropyl)carbodiimide (EDCI), as is known in the art.

Scheme A also depicts how to incorporate the terminal moiety, E-D-T, into the molecule. Regardless of whether Option A or Option B is chosen, a coupling reaction is ultimately carried out to attach the terminal moiety, E-D-T, to the 4-position of the pyridinone intermediate. In Scheme A, the co-reactant is depicted as E-D-T-$M^1$, where E-D-T-$M^1$ represents the same moiety as desired in the final product, except that it will be substituted with a metal (or metalloid) such as magnesium, copper, boronic ester/acid, etc. at the desired point of attachment to the pyridinone intermediate of structure 3 or 7 (i.e. the other reactant). The terminal groups encompassed by Formula I, i.e E-D-T, are either known in the art or can be prepared by methods analogously known in the art.

The coupling reaction can be carried out by a variety of techniques. The Suzuki-Miyaura strategy can be used to form the carbon-carbon bond. In such a reaction $M^1$ will be represented by a boronic acid/ester. Equivalent molar amounts of the reactants will be contacted in a solvent such as tetrahydrofuran, 2-methyltetrahydrofuran, 1,4-dioxane, water, toluene, or a mixture thereof in the presence of a transition metal catalyst such as a free or resin bound palladium or nickel species, together with a base such as sodium carbonate, potassium carbonate, cesium fluoride, cesium carbonate, etc. The reaction mixture can be heated by microwave or by other conventional techniques until adequate conversion is achieved. Once complete, the desired product may be isolated and recovered from the reaction and further purified as is known in the art. Analogously, the Castro-Stevens or Sonogashira-Hagihara strategy can be employed; the T moiety will be a suitable terminal acetylene species reacted in the presence of copper salt such as copper iodide. In such a reaction $M^1$ can be represented by the in situ generated cuprate species. Equivalent molar amounts of the reactants will be contacted in a solvent such as tetrahydrofuran, 2-methyltetrahydrofuran, dimethylformamide or a mixture thereof in the presence of a transition metal catalyst such as free or resin bound palladium or nickel, together with an appropriate base such as a suitable organic base for example N,N-diisopropylethylamine. The reaction mixture can be heated by microwave or by other conventional techniques until adequate conversion is achieved. Once complete, the desired product may be isolated and recovered from the reaction and further purified as is known in the art.

The reaction schemes depicted above for producing the compound of Formula I, are merely illustrative. As is readily apparent to one skilled in the art, they may be modified depending upon the specific compound, availability of reagents, etc.

Medical and Veterinary Uses

The compounds may be used for the treatment or prevention of infectious disorders, especially those caused by susceptible and multi-drug resistant (MDR) Gram-negative bacteria. Examples of such Gram-negative bacteria include *Acinetobacter baumannii, Acinetobacter* spp., *Achromobacter* spp., *Aeromonas* spp., *Bacteroides fragilis, Bordetella* spp., *Borrelia* spp., *Brucella* spp., *Campylobacter* spp., *Citrobacter diversus* (kosen), *Citrobacter freundii, Enterobacter aerogenes, Enterobacter cloacae, Escherichia coli, Francisella tularensis, Fusobacterium* spp., *Haemophilus influenzae* (β-lactamase positive and negative), *Helicobacter pylori, Klebsiella oxytoca, Klebsiella pneumoniae* (including those encoding extended-spectrum β-lactamases (hereinafter "ESBLs"), *Legionella pneumophila, Moraxella catarrhalis* (β-lactamase positive and negative), *Morganella morganii,*

*Neisseria gonorrhoeae, Neisseria meningitidis, Proteus vulgaris, Porphyromonas* spp., *Prevotella* spp., *Mannheimia haemolyticus, Pasteurella* spp., *Proteus mirabilis, Providencia* spp., *Pseudomonas aeruginosa, Pseudomonas* spp., *Salmonella* spp., *Shigella* spp., *Serratia marcescens, Treponema* spp., *Burkholderia cepacia, Vibrio* spp., *Yersinia* spp., and *Stenotrophomonas mulophilia.* Examples of other gram negative organisms include members of the Enterobacteriaceae that express ESBLs; KPCs, CTX-M, metallo-β-lactamases (such as NDM-1, for example), and AmpC-type beta-lactamases that confer resistance to currently available cephalosporins, cephamycins, carbapenems, and beta-lactam/beta-lactamase inhibitor combinations.

In a more specific embodiment, the Gram-negative bacteria are selected from the group consisting of *Acinetobacter baumannii, Acinetobacter* spp., *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia, Pseudomonas aeruginosa* and members of the Enterobacteriaceae and *Pseudomonas* that express ESBLs, KPCs, CTX-M, metallo-β-lactamases, and AmpC-type beta-lactamases that confer resistance to currently available cephalosporins, cephamycins, carbapenems, and beta-lactam/beta-lactamase inhibitor combinations.

Examples of infections that may be treated with the compounds of Formula I include nosocomial pneumonia, urinary tract infections, systemic infections (bacteremia and sepsis), skin and soft tissue infections, surgical infections, intraabdominal infections, lung infections in patients with cystic fibrosis, patients suffering from lung infections, endocarditis, diabetic foot infections, osteomyelitis, and central nervous system infections.

In addition, the compounds can be used to treat *Helicobacter pylori* infections in the GI tract of humans (and other mammals). Elimination of these bacteria is associated with improved health outcomes including fewer dyspeptic symptoms, reduced peptic ulcer recurrence and rebleeding, reduced risk of gastric cancer, etc. A more detailed discussion of eradicating *H. pylori* and its impact on gastrointestinal illness may be found at: on the world-wide web at informahealthcare.com; and Expert Opin. Drug Saf. (2008) 7 (3).

In order to exhibit this anti-infective activity, the compounds need to be administered in a therapeutically effective amount. A "therapeutically effective amount" is meant to describe a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.1 mg/kg/day to about 5000 mg/kg/day in single or in divided doses. Typically, dosages for humans will range from about 10 mg to about 3000 mg per day, in a single or multiple doses.

Any route typically used to treat infectious illnesses, including oral, parenteral, topical, rectal, transmucosal, and intestinal, can be used to administer the compounds. Parenteral administrations include injections to generate a systemic effect or injections directly into to the afflicted area. Examples of parenteral administrations are subcutaneous, intravenous, intramuscular, intradermal, intrathecal, and intraocular, intranasal, intravetricular injections or infusions techniques. Topical administrations include the treatment of areas readily accessible by local application, such as, for example, eys, ears including external and middle ear infections, vaginal, open wound, skin including the surface skin and the underneath dermal structures, or lower intestinal tract. Transmucosal administration includes nasal aerosol or inhalation applications.

Formulations

Compounds of the invention can be formulated for administration in any way for use in human or veterinary medicine, by analogy with other bioactive agents such as antibiotics. Such methods are known in the art and are summarized below.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, ophthalmic ointments/drops and otic drops, impregnated dressings and aerosols, and may contain appropriate conventional additives such as preservatives, solvents to assist drug penetration and emollients, etc. Such topical formulations may also contain conventional carriers, such as cream or ointment bases and ethanol or oleyl alcohol for lotions. Such carriers may be present, for example, from about 1% up to about 98% of the formulation.

Tablets and capsules for oral administration may be in unit dose presentation form, and may contain conventional excipients such as binding agents, for example acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being typical. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, to about 100% by weight, of the active material, depending on the method of administration. Where the compositions comprise dosage units, each unit will contain, for example, from about 0.5-1000 mg of the active ingredient. The dosage as employed for adult human treatment will range, for example, from about 10 to 3000 mg per day, depending on the route and frequency of administration.

If desired, the compounds of the invention may be administered in combination with one or more additional antibacterial agents ("the additional active agent"). Such use of compounds of the invention in combination with an additional active agent may be for simultaneous, separate or sequential use.

The Examples and preparations provided below further illustrate and exemplify the compounds of the present invention and methods of preparing such compounds. It is to be understood that the scope of the present invention is not limited in any way by the scope of the following Examples and preparations. In the following Examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Experimental Procedures

Experiments were generally carried out under an inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LCMS) or atmospheric pressure chemical ionization (APCI). Chemical shifts for nuclear magnetic resonance (NMR) data are expressed in parts per million (ppm, δ) referenced to residual peaks from the deuterated solvents employed. Melting points are uncorrected. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20-25° C.

For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

In the discussion above and in the Examples below, the following abbreviations have the following meanings. If an abbreviation is not defined, it has its generally accepted meaning.

| | |
|---|---|
| Ac = | acetate |
| ACN = | acetonitrile |
| $Ac_2O$ = | acetic anhydride |
| APCI = | atmospheric pressure chemical ionization |
| Aq. = | aqueous |
| 9-BBN = | 9-Borabicyclo[3.3.1]nonane |
| bd = | broad doublet |
| bm = | broad multiplet |
| bs = | broad singlet |
| BOC = | tert-butoxycarbonyl |
| ° C. = | degrees celsius |
| CBZ = | benzyloxycarbonyl |
| CDI = | 1,1'-carbonyldiimidazole |
| CDMT = | 2-chloro-4,6-dimethoxy-1,3,5-triazine |
| cm = | centimeter |
| d = | doublet |
| DCC = | 1,3-dicyclohexylcarbodiimide |
| DCM = | dichloromethane |
| dd = | doublet of doublets |
| ddd = | doublet of doublets of doublets |
| DIAD = | diisopropyl azodicarboxylate |
| DME = | dimethyl ether |
| DMF = | dimethylformamide |
| DMA = | dimethylacetamide |
| DMAP = | 4-dimethylaminopyridine |
| DMSO = | dimethyl sulfoxide |
| dq = | doublet of quartets |
| dt = | doublet of triplets |
| EDCI = | 1-ethyl-3-(3-dimethylaminopropyl)carbodiimide |
| eq. = | equivalents |
| EtO = | ethoxy |
| $Et_2O$ = | diethyl ether |
| EtOAc = | ethyl acetate |
| g = | grams |
| GCMS = | gas chromatography mass spectromety |
| h = | hours |
| $^1H$ = | proton |
| HATU = | (2-(7-aza-1H-benzotriazole-1-yl)-1,1,3,3-tetramethyluronium hexafluorophosphate) |
| HCl = | hydrochloric acid |
| $H_2N$-OTHP = | O-tetrahydro-2H-pyran-2-yl-hydroxylamine |
| HOBT = | Hydroxybenzotriazole |
| HPLC = | high pressure liquid chromatography |
| Hz = | hertz |
| IPA = | isopropanol |
| J = | coupling constant |
| KOAc = | potassium acetate |
| $K_3PO_4$ = | potassium phosphate |
| L = | liter |
| LCMS = | liquid chromatography mass spectrometry |
| LDA = | lithium diisopropylamide |
| LG = | leaving group |
| LiHMDS = | lithium hexamethyldisilazide/lithium bis(trimethylsilyl)amide |
| m = | multiplet |
| M = | molar |
| M % = | mole percent |
| max = | maximum |
| mCPBA = | meta-chloroperbenzoic acid |
| MeOH = | methanol |

-continued

| | |
|---|---|
| meq = | milliequivalent |
| MeTHF = | 2-methyltetrahydrofuran |
| mg = | milligram |
| $MgSO_4$ = | magnesium sulfate |
| MHz = | megahertz |
| min = | minutes |
| mL = | milliliter |
| mm = | millimeter |
| mmol = | millimole |
| MS = | mass spectrometry |
| MTBE = | methyl tert-butyl ether |
| m/z = | mass to charge ratio |
| N = | normality |
| $NaHCO_3$ = | sodium bicarbonate |
| $Na_2SO_4$ = | sodium sulfate |
| $NH_4Cl$ = | ammonium chloride |
| NMM = | N-methylmorpholine |
| NMP = | 1-methyl-2-pyrrolidinone |
| NMR = | nuclear magnetic resonance |
| Pd = | palladium |
| Pd EnCat ™ = | palladium acetate and BINAP, microencapsulated in polyurea matrix 0.39 mmol/g Pd loading BINAP 0.25, Pd 1.0 |
| $Pd(dppf)Cl_2$ = | bis(diphenylphosphino)ferrocenepalladium(II) chloride $Pd(dppf)Cl_2$ dichloromethane complex |
| $Pd(PPh_3)_4$ = | tetrakis(triphenylphosphine)palladium(0) |
| ppt = | precipitate |
| p-TLC = | preparative thin layer chromatography |
| PyBop = | benzotriazole-1-yl-oxy-trispyrrolidinophosphonium hexafluorophosphate |
| q = | quartet |
| $R_f$ = | retention factor |
| rt = | room temperature |
| s = | singlet |
| sat. = | saturated |
| t or tr = | triplet |
| TBAB = | tetrabutylammonium bromide |
| TBS = | tert-butyldimethylsilyl |
| TFA = | trifluoroacetic acid |
| THF = | tetrahydrofuran |
| THP = | tetrahydropyranyl |
| TLC = | thin layer chromatography |
| TMS = | trimethylsilyl |
| TPP = | triphenylphosphine |
| TPPO = | triphenylphosphine oxide |
| μL = | microliter |

Preparation of Starting Materials

Preparation 1

Synthesis of Template 1 (T1): Ethyl 4-bromo-2-methyl-2-(methylsulfonyl)butanoate and individual enantiomers (R) and (S)

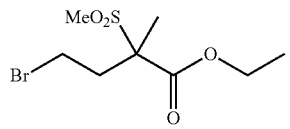

Step A) Ethyl 2-(methylsulfonyl)propanoate

Sodium methanesulfinate (103 g, 937 mmol) was combined with ethyl 2-chloropropionate (109 g, 892 mmol) in ethanol (350 mL) in a 500 mL one neck round bottom flask. The reaction was heated to 77° C. for 20 h, and then allowed to cool to room temperature. The solids were removed by filtration through celite, and the filter pad was washed with ethanol. The combined filtrates were concentrated in vacuo. The crude product was suspended in diethyl ether (250 mL), and solids were removed by filtration. The filtrate was concentrated in vacuo to afford the title compound as a pale yellow oil (51 g, 73%). $^1$H NMR (400 MHz, CHLOROFORM-d) δ ppm 1.32 (t, J=7.05 Hz, 3H) 1.67 (d, J=7.47 Hz, 3H) 3.05 (s, 3H) 3.83-3.92 (m, 1H) 4.18-4.37 (m, 2H).

Step B) Ethyl 4-bromo-2-methyl-2-(methylsulfonyl)butanoate

Sodium hydride (60% dispersion in mineral oil, 2.33 g, 58.3 mmol) was washed with hexanes (2×10 mL) in a 100 mL two neck round bottom flask under nitrogen then suspended in DMF (30 mL). The suspension was treated dropwise with ethyl 2-(methylsulfonyl)propanoate (10.0 g, 55.49 mmol) in DMF (10 mL). The mixture was stirred 30 min at RT, cooled to 0° C., and treated drop-wise with 1,2-dibromoethane (5.17 mL, 58.8). The mixture was allowed to warm to room temperature while stirring overnight. The mixture was quenched with saturated aq ammonium chloride (100 mL) and extracted with diethyl ether (4×50 mL). Combined organics were washed with 50% saturated sodium chloride (4×50 mL), dried ($MgSO_4$), and concentrated in vacuo. Crude material was purified via silica chromatography (350 g, 230-400 mesh) and an eluent of EtOAc in hexanes (10-20%) to afford the title compound as a pale yellow oil (7.9 g, 50%). $^1$H NMR (400 MHz, CHLOROFORM-d) δ ppm 1.33 (t, J=7.05 Hz, 3H) 1.64 (s, 3H) 2.49-2.59 (m, 1H) 2.78 (ddd, J=13.89, 10.16, 6.64 Hz, 1H) 3.05 (s, 3H) 3.33-3.41 (m, 1H) 3.46-3.54 (m, 1H) 4.22-4.37 (m, 2H).

Step C) Chiral separation of Ethyl 4-bromo-2-methyl-2-(methylsulfonyl)butanoate

Crude ethyl 4-bromo-2-methyl-2-(methylsulfonyl)butanoate (1.82 kg) was purified via flash chromatography using an LP-600 column and toluene as the eluent to afford pure ethyl 4-bromo-2-methyl-2-(methylsulfonyl)butanoate (1.63 kg). The purified material was dissolved in ethanol (75 g/L) and resolved via chiral column chromatography (conditions listed in Table 1) on MCC-2 to afford enantiomer #1 (738.4 g, rt=4.719 min, $[\alpha]_{589}^{20}$=+14.1° at 99% ee and enantiomer #2 (763.8 g, rt=4.040 min) at 95% ee. Purity of the enantiomers was determined via chiral HPLC, 4.6×250 mm Chiralpak AD, 10μ column, 215 nm wavelength, mobile phase: ethanol, isocratic elution at 1 mL/min at ambient temperature.

TABLE 1

| | |
|---|---|
| Stationary Phase | ChiralPak AD, 20μ |
| Column Dimension/Temp | 5 × 10 cm/30° C. |
| Mobile Phase | 100% ethanol |
| Feed Concentration | 75 g/L in mobile phase |
| Feed Rate | 4.0 mL/min |
| Eluent Rate | 90.5 mL/min |
| Raffinate Rate | 35.6 mL/min |
| Extract Rate | 58.9 mL/min |
| Recycling Rate | 262 mL/min |
| Period Time | 1.0 min |

Enantiomer #1 was determined to be ethyl (2R)-4-bromo-2-methyl-2-(methylsulfonyl)butanoate, Template 1 (T1).

Preparation 2

Scheme B illustrates the preparation of ethyl (2R)-4-(5-fluoro-4-iodo-2-oxopyridin-1(2H)-yl)-2-methyl-2-(methylsulfonyl)butanoate (T2) and (2R)-4-(5-fluoro-4-iodo-2-oxopyridin-1(2H)-yl)-2-methyl-2-(methylsulfonyl)-N-

(tetrahydro-2H-pyran-2-yloxy)butanamide (T3) and the corresponding racemic and diastereomeric mixtures ethyl 4-(5-fluoro-4-iodo-2-oxopyridin-1(2H)-yl)-2-methyl-2-(methylsulfonyl)butanoate (T4) and 4-(5-fluoro-4-iodo-2-oxopyridin-1(2H)-yl)-2-methyl-2-(methylsulfonyl)-N-(tetrahydro-2H-pyran-2-yloxy)butanamide (T5).

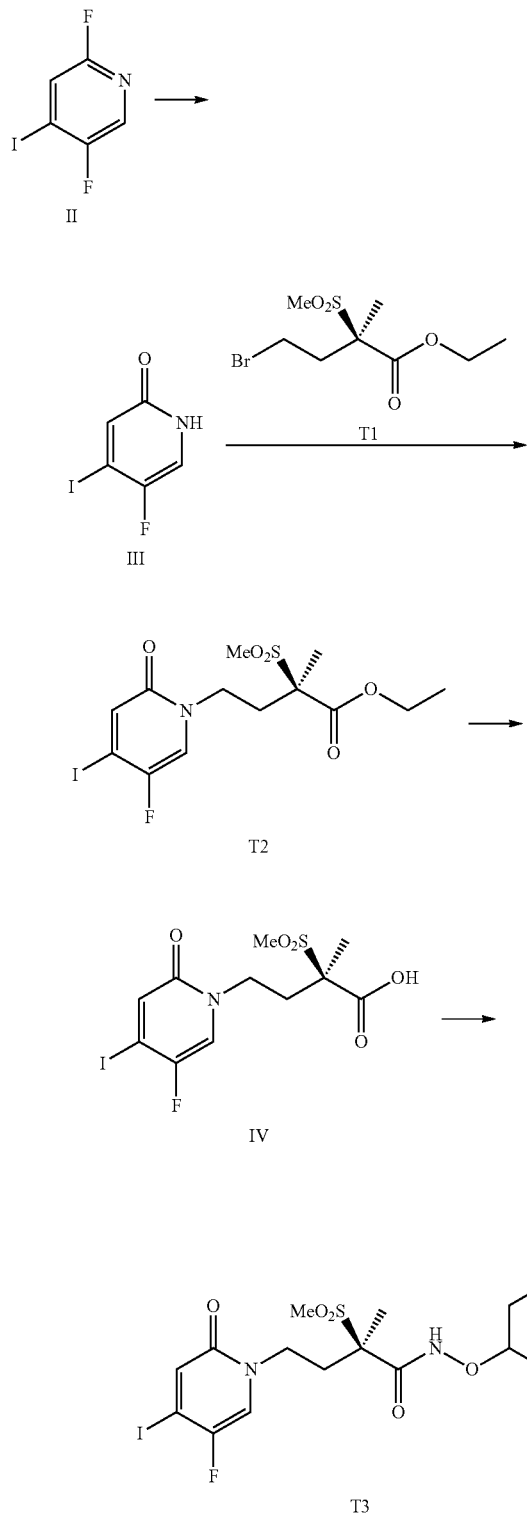

Synthesis of Template 3 (T3): (2R)-4-(5-Fluoro-4-iodo-2-oxopyridin-1(2H)-yl)-2-methyl-2-(methylsulfonyl)-N-(tetrahydro-2H-pyran-2-yloxy)butanamide

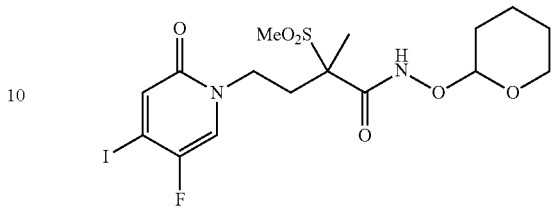

Step A) Compound III: 5-Fluoro-4-iodopyridin-2(1H)-one

Concentrated HCl (50 mL) was added to a mixture of 2,5-difluoro-4-iodopyridine (2.0 g, 8.3 mmol) in 1,4-dioxane (350 mL) and water (100 mL). The mixture was heated to reflux and stirred at this temperature overnight. The reaction was concentrated to dryness and the residue was triturated in water (20 mL). The solids were collected via filtration and washed with water (2×30 mL) and hexanes (3×30 mL). The solid was dried under vacuum to afford the title compound as a yellow solid (1.0 g, 50%). MS (LCMS) m/z 240.0 (M+1). $^1$H NMR (400 MHz, DMSO-$d_6$) δ ppm 7.02 (d, J=5.07 Hz, 1H) 7.68 (d, J=2.34 Hz, 1H) 11.50 (br. s., 1H).

Step B). Template 2 (T2): Ethyl (2R)-4-(5-fluoro-4-iodo-2-oxopyridin-1(2H)-yl)-2-methyl-2-(methylsulfonyl)butanoate Cesium carbonate (1.77 g, 5.44 mmol) was added to a suspension of 5-fluoro-4-iodopyridin-2(1H)-one (1.00 g, 4.2 mmol) and ethyl (2R)-4-bromo-2-methyl-2-(methylsulfonyl)butanoate (1.56 g, 5.44 mmol) in anhydrous THF (45 mL). The reaction was heated to 70° C. and stirred at this temperature overnight. The reaction was quenched with water (100 mL) and extracted with EtOAc (2×100 mL). The combined organics were washed with brine (100 mL), dried (MgSO$_4$), filtered, and concentrated. The crude product was purified via flash chromatography using a Varian SF15-24 g column and an eluent of EtOAc in n-heptane (30-80%) to afford the title compound as a yellow residue (691 mg, 37%). MS (LCMS) m/z 446.0 (M+1). $^1$H NMR (400 MHz, CHLOROFORM-d) δ ppm 1.36 (t, 3H) 1.75 (s, 3H) 2.37-2.57 (m, 2H) 3.10 (s, 3H) 3.83-4.02 (m, 1H) 4.16-4.37 (m, 3H) 7.15 (d, 1H) 7.20 (d, J=3.32 Hz, 1H).

Step C) Compound IV: (2R)-4-(5-Fluoro-4-iodo-2-oxopyridin-1(2H)-yl)-2-methyl-2-(methylsulfonyl) butanoic acid Potassium hydroxide (669 mg, 7.7 mmol) was added to a solution of ethyl (2R)-4-(5-fluoro-4-iodo-2-oxopyridin-1(2H)-yl)-2-methyl-2-(methylsulfonyl)butanoate (691 mg, 1.55 mmol) in 2-methyltetrahydrofuran:water (2:1 22.5 mL) and the solution was stirred at 70° C. for 2 h. The reaction was diluted with 1 N aq NaOH (50 mL). The organics were separated and the aqueous layer was washed with EtOAc (2×50 mL), and acidified to a pH of 3 using 3 M aqueous HCl. The aqueous layer was extracted with EtOAc (3×60 mL), dried (MgSO$_4$), filtered and concentrated to afford a yellow-white solid (290 mg, 44.8%). MS (LCMS) m/z 418.0. $^1$H NMR (400 MHz, DMSO-$d_6$) δ ppm 1.53 (s, 3H) 2.08-2.20 (m, 1H) 2.36-2.48 (m, 1H) 3.13 (s, 3H) 3.79-4.02 (m, 2H) 7.03 (d, J=6.05 Hz, 1H) 7.96 (d, J=4.29 Hz, 1H) 13.82 (br. s., 1H).

Step D) Template 3 (T3): (2R)-4-(5-Fluoro-4-iodo-2-oxopyridin-1(2H)-yl)-2-methyl-2-(methylsulfonyl)-N-(tetrahydro-2H-pyran-2-yloxy)butanamide N-Methylmorpholine (120 uL, 1.1 mmol) was added to a solution of CDMT (178 mg, 1.01 mmol) and (2R)-4-(5-fluoro-4-iodo-2-oxopyridin-1(2H)-yl)-2-methyl-2-(methylsulfonyl)butanoic acid (280 mg, 0.762 mmol) in 2-methyltetrahydrofuran (7.60 mL) and the reaction was stirred at rt for 1 h. THP-hydroxylamine (117 mg, 1.00 mmol) was added to the reaction and the reaction was stirred overnight at rt. The reaction was quenched with water (50 mL) and the aqueous layer was extracted with EtOAc (3×50 mL). The combined organics were washed with brine (50 mL), dried (MgSO$_4$), filtered, and concentrated to afford the title compound as an off-white solid (399.8 mg) MS (LCMS) 515.0 (M−1).

Example 1

(2R)-4-{5-Fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide

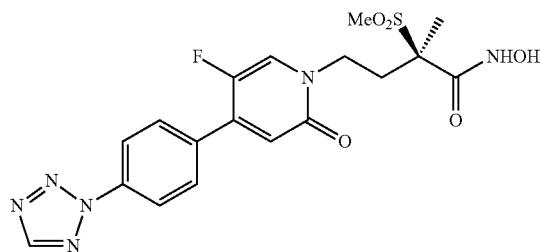

Step A) 2-[4-(4,4,5,5-Tetramethyl-1,3,2-dioxaborolan-2-yl)phenyl]-2H-tetrazole

Pd(dppf)Cl$_2$ (70.2 mg, 0.10 mmol) was added to a suspension of 4,4,4',4',5,5,5',5'-octamethyl-2,2'-bi-1,3,2-dioxaborolane (291 mg, 1.15 mmol), 2-(4-bromophenyl)-2H-tetrazole (215 mg, 0.96 mmol), and potassium acetate (191 mg, 1.91 mmol) in 1,4-dioxane (4.78 mL). The resulting suspension was heated to 80° C. and stirred at this temperature overnight. The reaction was allowed to cool, filtered through celite, and concentrated in vacuo. The crude product was purified via flash chromatography using a 40 g silica gel Redisep column and an eluent of EtOAc in n-heptane (0-50%) to afford the title compound as a light yellow solid (258 mg, 99%). MS (LCMS) m/z 273.2 (M+1). $^1$H NMR (400 MHz, CHLOROFORM-d) δ ppm 1.36 (s, 12H) 7.66-7.73 (m, 2H) 7.96-8.02 (m, 2H) 9.01 (s, 1H).

Step B) (2R)-4-{5-Fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide Pd EnCat™ (317 mg, 0.10 mmol) was added to a mixture of potassium carbonate (393 mg, 2.84 mmol), 2-[4-(4,4,5,5-tetramethyl-1,3,2-dioxaborolan-2-yl)phenyl]-2H-tetrazole (258.4 mg, 0.95 mmol), and (2R)-4-(5-fluoro-4-iodo-2-oxopyridin-1(2H)-yl)-2-methyl-2-(methylsulfonyl)-N-(tetrahydro-2H-pyran-2-yloxy)butanamide (490 mg, 0.95 mmol), T3, in 1,4-dioxane:water (4:1, 10 mL). The reaction was heated to 80° C. and stirred at this temperature overnight. The reaction was filtered through celite, and the filter pad was washed with methanol (250 mL). The combined filtrates were concentrated under reduced pressure, and the resulting crude material was purified via flash chromatography using an eluent of EtOAc in n-heptane (20-100%) and methanol in EtOAc (0-10%) to afford the title compound as a light tan solid (500 mg, 98%). MS (LCMS) m/z 534.4 (M−1). 0

Step C) (2R)-4-{5-Fluoro-2-oxo-4-[1-(2H-tetrazol-2-yl)phenyl]pyridin-1(2H)-yl}-N-hydroxy-2-methyl-2-(methylsulfonyl)butanamide Hydrochloric acid (4.0 M in 1,4-dioxane, 1.7 mL, 6.63 mmol) was added to a solution of (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide (500 mg, 0.94 mmol) in dichloromethane:methanol (5:1, 6 mL) at room temperature. The reaction was stirred for 1 h then was concentrated under reduced pressure affording a residue, which was triturated in diethyl ether:pentane (1:1) overnight. The solid was collected via filtration and dried under reduced pressure to afford the title compound as a solid (340 mg, 76%). MS (LCMS) m/z 451.0 (M+1). $^1$H NMR (400 MHz, DMSO-$d_6$) δ ppm 1.56 (s, 3H) 2.09-2.21 (m, 1H) 2.42-2.45 (m, 1H) 3.09 (s, 3H) 3.78 (m, J=11.80, 11.80, 5.20 Hz, 1H) 3.97-4.10 (m, 1H) 6.63 (d, J=7.61 Hz, 1H) 7.84 (dd, J=8.68, 1.66 Hz, 2H) 8.00-8.15 (m, 3H) 10.16 (s, 1H) 11.08 (br. s., 1H).

Example 2

2R)-4-[5-Fluoro-4-(2-fluoro-3-methylphenyl)-2-oxopyridin-1(2H)-yl]-N-hydroxy-2-methyl-2-(methylsulfonyl)butanamide

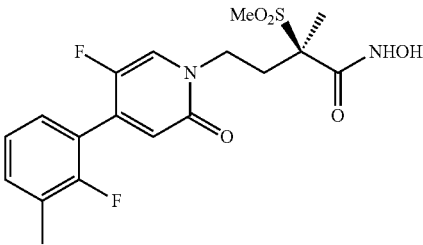

Step A) (2R)-4-[5-Fluoro-4-(2-fluoro-3-methylphenyl)-2-oxopyridin-1(2H)-yl]-2-methyl-2-(methylsulfonyl)-N-(tetrahydro-2H-pyran-2-yloxy)butanamide The title compound (470 mg, 48.7%) was obtained as a solid from (2-fluoro-3-methylphenyl)boronic acid (388 mg, 2.52 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, Example 1, Step B. MS (LCMS) m/z 499 (M+1). $^1$H NMR (400 MHz, METHANOL-$d_4$) δ ppm 1.49-1.57 (m, 3H) 1.59 (d, J=3.71 Hz, 3H) 1.64-1.74 (m, 3H) 2.16-2.26 (m, 1H) 2.27-2.31 (m, 3H) 3.10 (d, J=5.66 Hz, 3H) 3.31 (s, 1H) 3.47-3.55 (m, 1H) 3.72-3.88 (m, 1H) 3.90 (s, 1H) 3.99-4.15 (m, 2H) 4.94-4.99 (m, 1H) 6.47 (d, J=7.22 Hz, 1H) 7.20-7.26 (m, 1H) 7.26-7.32 (m, 1H) 7.40-7.47 (m, 1H) 8.01 (dd, J=11.90, 5.85 Hz, 1H) 11.52 (d, J=3.51 Hz, 1H).

Step B) (2R)-4-[5-Fluoro-4-(2-fluoro-3-methylphenyl)-2-oxopyridin-1(2H)-yl]-N-hydroxy-2-methyl-2-(methylsulfonyl)butanamide The title compound (185 mg, 46.6%) was obtained as a solid from (2R)-4-[5-fluoro-4-(2-fluoro-3-methylphenyl)-2-oxopyridin-1(2H)-yl]-2-methyl-2-(methylsulfonyl)-N-(tetrahydro-2H-pyran-2-yloxy)butanamide (477 mg, 0.957 mmol) using a procedure analogous to that described for (2R)-4-{5-fluoro-2-oxo-4-[4-(2H-tetrazol-2-yl)phenyl]pyridin-1(2H)-yl}-N-hydroxy-2-methyl-2-(methylsulfonyl)butanamide, Example 1, Step C. MS (LCMS) m/z 415 (M+1) $^1$H NMR (400 MHz, DMSO-$d_6$) δ ppm 1.54 (s, 3H) 2.13 (ddd, J=13.03, 11.07, 4.78 Hz, 1H) 2.40-2.45 (m, 1H) 3.08 (s, 3H) 3.76 (td, J=11.81, 5.07 Hz, 1H) 4.02 (td, J=11.85, 5.17 Hz, 1H) 6.53 (d, J=7.61 Hz, 1H) 7.45-7.64 (m, 4H) 8.02 (d, J=6.63 Hz, 1H) 9.11-9.26 (m, 1H) 11.00-11.13 (m, 1H).

Example 3

(2R)-4-[4-(4-Chlorophenyl)-5-fluoro-2-oxopyridin-1(2H)-yl]-N-hydroxy-2-methyl-2-(methylsulfonyl)butanamide

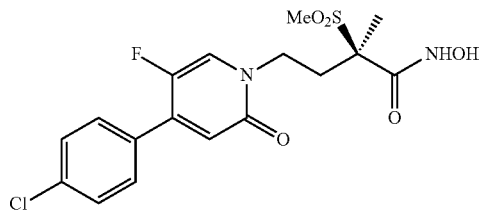

Step A) (2R)-4-[4-(4-Chlorophenyl)-5-fluoro-2-oxopyridin-1(2H)-yl]-2-methyl-2-(methylsulfonyl)-N-(tetrahydro-2H-pyran-2-yloxy)butanamide The title compound (870 mg, 59.8%) was obtained as a solid from (4-chlorophenyl)boronic acid (610 mg, 4.36 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, Example 1, Step B. MS (LCMS) m/z 502 (M+1). $^1$H NMR (400 MHz, DMSO-$d_6$) δ ppm 1.17-1.28 (m, 2H) 1.45-1.53 (m, 3H) 1.56 (d, J=3.71 Hz, 3H) 1.60-1.72 (m, 3H) 2.08-2.23 (m, 1H) 3.07 (d, J=6.44 Hz, 3H) 3.48 (d, J=11.12 Hz, 1H) 3.67-3.85 (m, 1H) 3.96-4.12 (m, 2H) 4.88-4.97 (m, 1H) 6.53 (d, J=7.61 Hz, 1H) 7.50-7.62 (m, 3H) 8.00 (dd, J=13.07, 6.63 Hz, 1H) 11.50 (s, 1H).

Step B) (2R)-4-[4-(4-Chlorophenyl)-5-fluoro-2-oxopyridin-1(2H)-yl]-N-hydroxy-2-methyl-2-(methylsulfonyl)butanamide The title compound (340 mg, 47.0%) was obtained as a solid from (2R)-4-[4-(4-chlorophenyl)-5-fluoro-2-oxopyridin-1(2H)-yl]-2-methyl-2-(methylsulfonyl)-N-(tetrahydro-2H-pyran-2-yloxy)butanamide (870 mg, 1.74 mmol) using a procedure analogous to that described for (2R)-4-{5-fluoro-2-oxo-4-[4-(2H-tetrazol-2-yl)phenyl]pyridin-1(2H)-yl}-N-hydroxy-2-methyl-2-(methylsulfonyl)butanamide, Example 1, Step C. MS (LCMS) m/z 417 (M+1). $^1$H NMR (400 MHz, DMSO-$d_6$) δ ppm 1.54 (s, 3H) 2.13 (ddd, J=13.12, 11.27, 5.07 Hz, 1H) 2.37-2.45 (m, 1H) 3.08 (s, 3H) 3.76 (td, J=11.90, 5.07 Hz, 1H) 3.93-4.12 (m, 1H) 6.53 (d, J=7.61 Hz, 1H) 7.49-7.66 (m, 4H) 8.02 (d, J=6.63 Hz, 1H) 9.21 (s, 1H) 10.95-11.17 (m, 1H).

Example 4

(2R)-4-[5-Fluoro-4-(2-fluorophenyl)-2-oxopyridin-1(2H)-yl]-N-hydroxy-2-methyl-2-(methylsulfonyl)butanamide

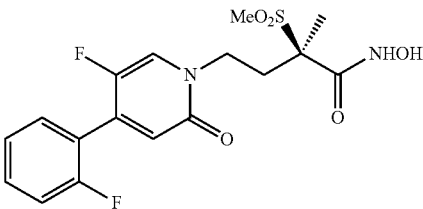

Step A) (2R)-4-[5-Fluoro-4-(2-fluorophenyl)-2-oxopyridin-1(2H)-yl]-2-methyl-2-(methylsulfonyl)-N-(tetrahydro-2H-pyran-2-yloxy)butanamide The title compound (230 mg, 81.7%) was obtained as a solid from (2-fluorophenyl)boronic acid (122 mg, 0.871 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, Example 1, Step B. MS (LCMS) m/z 485 (M+1). $^1$H NMR (400 MHz, DMSO-$d_6$) δ ppm 1.21-1.28 (m, 2H) 1.48-1.56 (m, 3H) 1.58 (d, J=3.71 Hz, 3H) 1.63-1.74 (m, 3H) 2.15-2.26 (m, 1H) 3.10 (d, J=5.66 Hz, 3H) 3.34 (br. s., 1H) 3.51 (d, J=10.73 Hz, 1H) 3.71-3.88 (m, 1H) 3.99-4.15 (m, 2H) 4.94-4.99 (m, 1H) 6.50 (d, J=7.02 Hz, 1H) 7.31-7.40 (m, 2H) 7.46-7.53 (m, 1H) 7.56 (m, J=7.76, 7.76, 5.56, 1.76 Hz, 1H) 8.01 (dd, J=11.90, 5.85 Hz, 1H) 11.51 (d, J=3.32 Hz, 1H).

Step B) (2R)-4-[5-Fluoro-4-(2-fluorophenyl)-2-oxopyridin-1(2H)-yl]-N-hydroxy-2-methyl-2-(methylsulfonyl)butanamide The title compound (68 mg, 36.0%) was obtained as a solid from (2R)-4-[5-fluoro-4-(2-fluorophenyl)-2-oxopyridin-1(2H)-yl]-2-methyl-2-(methylsulfonyl)-N-(tetrahydro-2H-pyran-2-yloxy)butanamide (230 mg, 0.475 mmol) using a procedure analogous to that described for (2R)-4-{5-fluoro-2-oxo-4-[4-(2H-tetrazol-2-yl)phenyl]pyridin-1(2H)-yl}-N-hydroxy-2-methyl-2-(methylsulfonyl)butanamide, -Example 1, Step C. MS (LCMS) m/z 401 (M+1). $^1$H NMR (400 MHz, DMSO-$d_6$) δ ppm 1.58 (s, 3H) 2.18 (td, J=12.15, 4.98 Hz, 1H) 2.47 (m, 1H) 3.12 (s, 3H) 3.79 (td, J=11.85, 5.17 Hz, 1H) 4.07 (td, J=11.81, 4.68 Hz, 1H) 6.50 (d, J=7.02 Hz, 1H)

7.30-7.44 (m, 2H) 7.46-7.64 (m, 2H) 8.04 (d, J=6.05 Hz, 1H) 9.20-9.32 (m, 1H) 10.99-11.17 (m, 1H).

Example 5

(2R)-4-[4-(2,3-Dihydro-1-benzofuran-5-yl)-5-fluoro-2-oxopyridin-1(2H)-yl]-N-hydroxy-2-methyl-2-(methylsulfonyl)butanamide

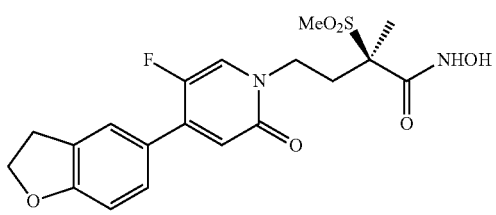

Step A) (2R)-4-[4-(2,3-Dihydro-1-benzofuran-5-yl)-5-fluoro-2-oxopyridin-1(2H)-yl]-2-methyl-2-(methylsulfonyl)-N-(tetrahydro-2H-pyran-2-yloxy)butanamide The title compound (198 mg, 61.0%) was obtained as a solid from 2,3-dihydro-1-benzofuran-5-ylboronic acid (153 mg, 0.871 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, -Example 1, Step B. MS (LCMS) m/z 509 (M+1). $^1$H NMR (400 MHz, DMSO-$d_6$) δ ppm 1.46-1.56 (m, 2H) 1.58 (d, J=4.10 Hz, 3H) 1.63-1.76 (m, 3H) 2.12-2.27 (m, 1H) 2.40-2.48 (m, 1H) 3.10 (d, J=6.05 Hz, 3H) 3.23 (t, J=8.78 Hz, 2H) 3.35 (br. s, 1H) 3.51 (d, J=12.10 Hz, 1H) 3.67-3.88 (m, 1H) 3.98-4.15 (m, 2H) 4.59 (t, J=8.78 Hz, 2H) 4.96 (d, J=2.73 Hz, 1H) 6.46 (d, J=7.81 Hz, 1H) 6.81-6.92 (m, 1H) 7.28-7.39 (m, 1H) 7.47 (s, 1H) 7.96 (dd, J=12.78, 6.73 Hz, 1H) 11.55 (s, 1H).

Step B) (2R)-4-[4-(2,3-Dihydro-1-benzofuran-5-yl)-5-fluoro-2-oxopyridin-1(2H)-yl]-N-hydroxy-2-methyl-2-(methylsulfonyl)butanamide The title compound (165 mg, 53.0%) was obtained as a solid from (2R)-4-[4-(2,3-dihydro-1-benzofuran-5-yl)-5-fluoro-2-oxopyridin-1(2H)-yl]-2-methyl-2-(methylsulfonyl)-N-(tetrahydro-2H-pyran-2-yloxy)butanamide (198 mg, 0.389 mmol) using a procedure analogous to that described for (2R)-4-{5-fluoro-2-oxo-4-[4-(2H-tetrazol-2-yl)phenyl]pyridin-1(2H)-yl}-N-hydroxy-2-methyl-2-(methylsulfonyl)butanamide, -Example 1, Step C. MS (LCMS) m/z 425 (M+1). $^1$H NMR (400 MHz, DMSO-$d_6$) δ ppm 1.57 (s, 3H) 2.16 (dd, J=5.56, 1.07 Hz, 1H) 2.36-2.49 (m, 1H) 3.11 (s, 3H) 3.23 (t, J=8.59 Hz, 2H) 3.66-3.86 (m, 1H) 4.04 (dd, J=6.15, 0.88 Hz, 1H) 4.59 (t, J=8.78 Hz, 2H) 6.45 (d, J=7.81 Hz, 1H) 6.87 (d, J=8.39 Hz, 1H) 7.34 (dd, J=8.20, 1.95 Hz, 1H) 7.46 (s, 1H) 7.98 (d, J=6.83 Hz, 1H) 9.15-9.31 (m, 1H) 11.01-11.19 (m, 1H).

Example 6

(2R)-4-[4-(3,4-Difluorophenyl)-5-fluoro-2-oxopyridin-1(2H)-yl]-N-hydroxy-2-methyl-2-(methylsulfonyl)butanamide

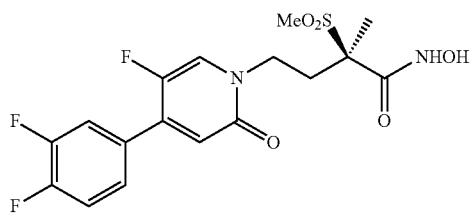

Step A) (2R)-4-[4-(3,4-Difluorophenyl)-5-fluoro-2-oxopyridin-1(2H)-yl]-2-methyl-2-(methylsulfonyl)-N-(tetrahydro-2H-pyran-2-yloxy)butanamide The title compound (760 mg, 52.1%) was obtained as a solid from (3,4-difluorophenyl)boronic acid (596 mg, 3.78 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, Example 1, Step B. MS (LCMS) m/z 503 (M+1).

Step B) (2R)-4-[4-(3,4-Difluorophenyl)-5-fluoro-2-oxopyridin-1(2H)-yl]-N-hydroxy-2-methyl-2-(methylsulfonyl)butanamide The title compound (350 mg, 55.0%) was obtained as a solid from (2R)-4-[4-(3,4-difluorophenyl)-5-fluoro-2-oxopyridin-1(2H)-yl]-2-methyl-2-(methylsulfonyl)-N-(tetrahydro-2H-pyran-2-yloxy)butanamide (760 mg, 1.51 mmol) using a procedure analogous to that described for (2R)-4-{5-fluoro-2-oxo-4-[4-(2H-tetrazol-2-yl)phenyl]pyridin-1(2H)-yl}-N-hydroxy-2-methyl-2-(methylsulfonyl)butanamide, Example 1, Step C. MS (LCMS) m/z 419 (M+1). $^1$H NMR (400 MHz, DMSO-$d_6$) δ ppm 1.57 (s, 3H) 2.06-2.25 (m, 1H) 2.38-2.48 (m, 1H) 3.11 (s, 3H) 3.68-3.87 (m, 1H) 3.96-4.18 (m, 1H) 6.60 (d, J=7.61 Hz, 1H) 7.37-7.52 (m, 1H)

7.52-7.65 (m, 1H) 7.65-7.84 (m, 1H) 8.06 (d, J=6.63 Hz, 1H) 9.13-9.39 (m, 1H) 11.08 (s, 1H).

Example 7

(2R)-4-{5-Fluoro-2-oxo-4-[4-(2,2,2-trifluoroethoxy)phenyl]pyridin-1(2H)-yl}-N-hydroxy-2-methyl-2-(methylsulfonyl)butanamide

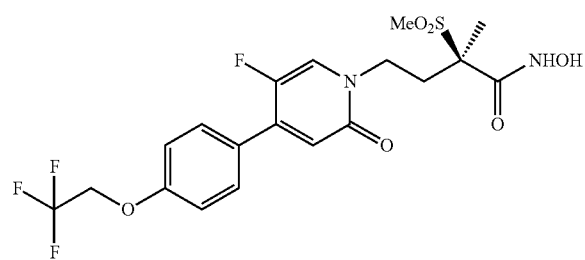

Step A) (2R)-4-{5-Fluoro-2-oxo-4-[4-(2,2,2-trifluoroethoxy)phenyl]pyridin-1(2H)-yl}-2-methyl-2-(methylsulfonyl)-N-(tetrahydro-2H-pyran-2-yloxy)butanamide The title compound (860 mg, 78.6%) was obtained as a solid from [4-(2,2,2-trifluoroethoxy)phenyl]boronic acid (554 mg, 2.52 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, Example 1, Step B. MS (LCMS) m/z 565 (M+1).

Step B) (2R)-4-{5-Fluoro-2-oxo-4-[4-(2,2,2-trifluoroethoxy)phenyl]pyridin-1(2H)-yl}-N-hydroxy-2-methyl-2-(methylsulfonyl)butanamide The title compound (310 mg, 42.3%) was obtained as a solid from (2R)-4-{5-fluoro-2-oxo-4-[4-(2,2,2-trifluoroethoxy)phenyl]pyridin-1(2H)-yl}-2-methyl-2-(methylsulfonyl)-N-(tetrahydro-2H-pyran-2-yloxy)butanamide (860 mg, 1.52 mmol) using a procedure analogous to that described for (2R)-4-{5-fluoro-2-oxo-4-[4-(2H-tetrazol-2-yl)phenyl]pyridin-1(2H)-yl}-N-hydroxy-2-methyl-2-(methylsulfonyl)butanamide, Example 1, Step C. MS (LCMS) m/z 419 (M+1). $^1$H NMR (400 MHz, DMSO-$d_6$) δ ppm 1.54 (s, 3H) 2.06-2.22 (m, 1H) 2.37-2.45 (m, 1H) 3.08 (s, 3H) 3.74 (td, J=11.76, 4.98 Hz, 1H) 3.93-4.10 (m, 1H) 4.81 (q, J=8.98 Hz, 2H) 6.49 (d, J=7.61 Hz, 1H) 7.16 (d, J=8.98 Hz, 2H) 7.49-7.62 (m, 2H) 7.98 (d, J=6.63 Hz, 1H) 9.21 (br. s., 1H) 11.07 (s).

Example 8

(2R)-4-[4-(3,4-Dihydro-2H-chromen-6-yl)-5-fluoro-2-oxopyridin-1(2H)-yl]-N-hydroxy-2-methyl-2-(methylsulfonyl)butanamide

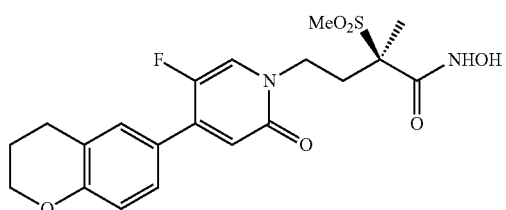

Step A) (2R)-4-[4-(3,4-Dihydro-2H-chromen-6-yl)-5-fluoro-2-oxopyridin-1(2H)-yl]-2-methyl-2-(methylsulfonyl)-N-(tetrahydro-2H-pyran-2-yloxy)butanamide The title compound (500 mg, 82.3%) was obtained as a solid from 3,4-dihydro-2H-chromen-6-ylboronic acid (228 mg, 1.28 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, Example 1, Step B. MS (LCMS) m/z 523 (M+1).

Step B) (2R)-4-[4-(3,4-Dihydro-2H-chromen-6-yl)-5-fluoro-2-oxopyridin-1(2H)-yl]-N-hydroxy-2-methyl-2-(methylsulfonyl)butanamide The title compound (240 mg, 57.1%) was obtained as a solid from (2R)-4-[4-(3,4-dihydro-2H-chromen-6-yl)-5-fluoro-2-oxopyridin-1(2H)-yl]-2-methyl-2-(methylsulfonyl)-N-(tetrahydro-2H-pyran-2-yloxy)butanamide (500 mg, 0.957 mmol) using a procedure analogous to that described for (2R)-4-{5-fluoro-2-oxo-4-[4-(2H-tetrazol-2-yl)phenyl]pyridin-1(2H)-yl}-N-hydroxy-2-methyl-2-(methylsulfonyl)butanamide, Example 1, Step C. MS (LCMS) m/z 439 (M+1). $^1$H NMR (400 MHz, DMSO-$d_6$) δ ppm 1.52 (s, 3H) 1.83-1.97 (m, 2H) 2.12 (ddd, J=13.03, 11.27, 5.17 Hz, 1H) 2.34-2.44 (m, 1H) 2.75 (t, J=6.34 Hz, 2H) 3.07 (s, 3H) 3.71 (td, J=11.76, 5.17 Hz, 1H) 3.92-4.07 (m, 1H) 4.08-4.20 (m, 2H) 6.42 (d, J=7.61 Hz, 1H) 6.79 (d, J=8.39 Hz, 1H) 7.20-7.32 (m, 2H) 7.94 (d, J=6.83 Hz, 1H) 9.20 (br. s., 1H) 11.07 (s, 1H).

Example 9

(2R)-4-{5-Fluoro-4-[4-(methylthio)phenyl]-2-oxopyridin-1(2H)-yl}-N-hydroxy-2-methyl-2-(methylsulfonyl)butanamide

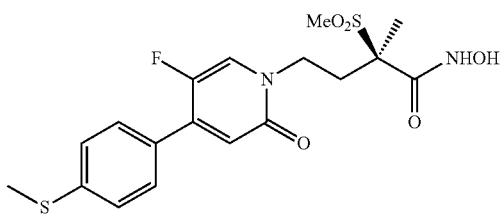

Step A) Ethyl (2R)-4-{5-fluoro-4-[4-(methylthio)phenyl]-2-oxopyridin-1(2H)-yl}-2-methyl-2-(methylsulfonyl)butanoate 1,4-Dioxane (10 ml) and 3 M aq $K_3PO_4$ (1.12 mL, 3.3 mmol) was added to a flask containing [4-(methylthio)phenyl]boronic acid (0.283 g, 1.68 mmol), Pd(dppf)Cl$_2$ (82 mg, 0.112 mmol) and ethyl (2R)-4-(5-fluoro-4-iodo-2-oxopyridin-1(2H)-yl)-2-methyl-2-(methylsulfonyl)butanoate, T2, (500 mg, 1.12 mmol) that was previously flushed with nitrogen. The mixture was heated to 60° C. and stirred at this temperature for 1 h. The reaction mixture was diluted with EtOAc and washed with water. The organics were dried (MgSO$_4$), filtered, and concentrated. The crude product was purified via flash chromatography on a 40 g silica column and an eluent of EtOAc in n-heptane (0-100%) to afford the title compound as a gum (492 mg, 99%). MS (LCMS) m/z 442.1 (M+1). $^1$H NMR (400 MHz, CHLOROFORM-d) δ ppm 1.17-1.27 (m, 3H) 1.74 (s, 3H) 2.38-2.61 (m, 5H) 3.09 (s, 3H) 3.88-4.02 (m, 1H) 4.17-4.32 (m, 3H) 6.57 (d, J=7.61 Hz, 1H) 7.21-7.34 (m, 3H) 7.37-7.48 (m, 2H).

Step B) (2R)-4-{5-Fluoro-4-[4-(methylthio)phenyl]-2-oxopyridin-1(2H)-yl}-2-methyl-2-(methylsulfonyl)butanoic acid Lithium hydroxide monohydrate (165 mg, 6.68 mmol) was added to a solution of ethyl (2R)-4-{5-fluoro-4-[4-(methylthio)phenyl]-2-oxopyridin-1(2H)-yl}-2-methyl-2-(methylsulfonyl)butanoate (0.492 g, 1.12 mmol) in THF:water (1:1, 14 mL) and the reaction was allowed to stir at rt for 18 h. The reaction mixture was acidified using 4 M aq HCl to afford a precipitate. The solid was collected via filtration and dried under vacuum to afford the title compound as a solid (339 mg, 73%). MS (LCMS) m/z 414.1 (M+1). $^1$H NMR (400 MHz, DMSO-d$_6$) δ ppm 1.54 (s, 3H) 2.17 (ddd, J=13.42, 10.00, 5.07 Hz, 1H) 2.41-2.45 (m, 1H) 2.49 (s, 3H), 3.14 (s, 3H) 3.78-4.15 (m, 2H) 6.46 (d, J=7.81 Hz, 1H) 7.28-7.39 (m, 2H) 7.43-7.55 (m, 2H) 8.01 (d, J=6.83 Hz, 1H).

Step C) (2R)-4-{5-Fluoro-4-[4-(methylthio)phenyl]-2-oxopyridin-1(2H)-yl}-2-methyl-2-(methylsulfonyl)-N-(tetrahydro-2H-pyran-2-yloxy)butanamide N,N-Diisopropylethylamine (450 uL, 2.45 mmol), O-(tetrahydro-2H-pyran-2-yl)hydroxylamine (192 mg, 1.64 mmol) and HATU (447 mg, 1.23 mmol) were added to a solution of (2R)-4-{5-fluoro-4-[4-(methylthio)phenyl]-2-oxopyridin-1(2H)-yl}-2-methyl-2-(methylsulfonyl)butanoic acid (339 mg, 0.82 mmol) in DMF (10 mL). The reaction was allowed to stir at rt for 18 h. The reaction mixture was diluted with EtOAc and washed with brine. The organics were dried (MgSO$_4$), filtered and concentrated. The crude residue was purified via flash chromatography using a 40 g silica column and an eluent of EtOAc in n-heptane (0-100%) to afford the title compound (420 mg, 100%). MS (LCMS) m/z 511.4 (M−1).

Step D) (2R)-4-{5-Fluoro-4-[4-(methylthio)phenyl]-2-oxopyridin-1(2H)-yl}-N-hydroxy-2-methyl-2-(methylsulfonyl)butanamide Aqueous HCl (4 M, 3 mL) was added to a solution of 2R)-4-{5-fluoro-4-[4-(methylthio)phenyl]-2-oxopyridin-1(2H)-yl}-2-methyl-2-(methylsulfonyl)-N-(tetrahydro-2H-pyran-2-yloxy)butanamide (437 mg, 0.852 mmol) in THF (10 mL) and the reaction was allowed to stir at it for 3 h. The reaction mixture was concentrated and then azeotroped with EtOAc and n-heptane several times to give the title compound as an off-white solid (233 mg, 64%). MS (LCMS) m/z 429.1 (M+1). $^1$H NMR (400 MHz, METHANOL-d$_4$) δ ppm 1.69 (s, 3H) 2.37 (ddd, J=13.51, 10.59, 5.17 Hz, 1H) 2.51 (s, 3H) 2.57-2.74 (m, 1H) 2.82 (s, 3H) 3.09 (s, 3H) 3.97 (ddd, J=13.12, 10.59, 5.56 Hz, 1H) 4.27 (ddd, J=13.03, 10.49, 5.17 Hz, 1H) 6.68 (d, J=7.22 Hz, 1H) 7.25-7.40 (m, 2H) 7.47-7.59 (m, 2H) 7.90 (d, J=6.05 Hz, 1H).

Example 10

(2R)-4-[4-(4-Ethoxyphenyl)-5-fluoro-2-oxopyridin-1(2H)-yl]-N-hydroxy-2-methyl-2-(methylsulfonyl)butanamide

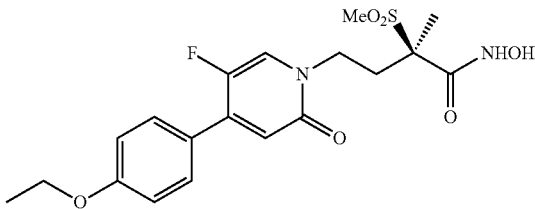

Step A) Ethyl (2R)-4-[4-(4-ethoxyphenyl)-5-fluoro-2-oxopyridin-1(2H)-yl]-2-methyl-2-(methylsulfonyl)butanoate The title compound (320 mg, 64%) was obtained as a gum from (4-ethoxyphenyl)boronic acid (280 mg, 1.68 mmol) using a procedure analogous to that described for ethyl (2R)-4-{5-fluoro-4-[4-(methylthio)phenyl]-2-oxopyridin-1(2H)-yl}-2-methyl-2-(methylsulfonyl)butanoate, Example 9, Step A. MS (LCMS) m/z 440.3 (M+1). $^1$H NMR (400 MHz, CHLOROFORM-d) δ ppm 1.22 (t, J=7.12 Hz, 3H) 1.40 (t, J=7.02 Hz, 3H) 1.73 (s, 3H) 2.36-2.61 (m, 2H) 3.09 (s, 3H) 3.85-3.98 (m, 1H) 4.07 (dd, J=14.93, 7.12 Hz, 2H) 4.25 (m, 3H) 6.51-6.58 (m, 1H) 6.93 (d, J=8.98 Hz, 3H) 7.22-7.31 (m, 1H) 7.44 (d, J=7.02 Hz, 1H).

Step B) (2R)-4-[4-(4-Ethoxyphenyl)-5-fluoro-2-oxopyridin-1(2H)-yl]-2-methyl-2-(methylsulfonyl)butanoic acid Lithium hydroxide (108 mg, 4.37 mmol) was added to a solution of ethyl (2R)-4-[4-(4-ethoxyphenyl)-5-fluoro-2-oxopyridin-1(2H)-yl]-2-methyl-2-(methylsulfonyl)butanoate (320 mg, 0.728 mmol) in tetrahydrofuran:water (1:1, 20 mL) and the reaction was allowed to stir at rt until complete. The reaction mixture was acidified with 4 M aq HCl and extracted with EtOAc. The combined organic layers were dried (MgSO$_4$), filtered and concentrated to afford the title compound as a solid (220 mg, 73%). MS (LCMS) m/z 412.2 (M+1). $^1$H NMR (400 MHz, DMSO-d$_6$) δ ppm 1.26-1.40 (m, 3H) 1.54 (s, 3H) 2.07-2.26 (m, 1H) 2.43 (d, J=6.24 Hz, 1H) 3.14 (s, 3H) 3.83-4.15 (m, 4H) 6.42 (d, J=7.81 Hz, 1H) 6.93-7.07 (m, 2H) 7.50 (dd, J=8.68, 1.85 Hz, 2H) 7.97 (d, J=6.83 Hz, 1H).

Step C) (2R)-4-[4-(4-Ethoxyphenyl)-5-fluoro-2-oxopyridin-1(2H)-yl]-2-methyl-2-(methylsulfonyl)-N-(tetrahydro-2H-pyran-2-yloxy)butanamide The title compound (273 mg, 100%) was obtained from (2R)-4-[4-(4-ethoxyphenyl)-5-fluoro-2-oxopyridin-1(2H)-yl]-2-methyl-2-(methylsulfonyl)butanoic acid (220 mg, 0.535 mmol) using a procedure analogous to that described for (2R)-4-{5-fluoro-4-[4-(methylthio)phenyl]-2-oxopyridin-1(2H)-yl}-2-methyl-2-(methylsulfonyl)-N-(tetrahydro-2H-pyran-2-yloxy)butanamide, Example 9, Step C. MS (LCMS) m/z 509.4 (M+1).

Step D) (2R)-4-[4-(4-Ethoxyphenyl)-5-fluoro-2-oxopyridin-1(2H)-yl]-N-hydroxy-2-methyl-2-(methylsulfonyl)butanamide The title compound (205 mg, 83%) was obtained as a solid from (2R)-4-[4-(4-ethoxyphenyl)-5-fluoro-2-oxopyridin-1(2H)-yl]-2-methyl-2-(methylsulfonyl)-N-(tetrahydro-2H-pyran-2-yloxy)butanamide (297 mg, 0.582 mmol) using a procedure analogous to that described for (2R)-4-{5-fluoro-4-[4-(methylthio)phenyl]-2-oxopyridin-1(2H)-yl}-N-hydroxy-2-methyl-2-(methylsulfonyl)butanamide, Example 9, Step D. MS (LCMS) m/z 427.2 (M+1). $^1$H NMR (400 MHz, METHANOL-d$_4$) δ ppm 1.40 (t, J=6.93 Hz, 3H) 1.69 (s, 3H) 2.28-2.42 (m, 1H) 2.54-2.69 (m, 1H) 3.09 (s, 3H) 3.86-3.99 (m, 1H) 4.09 (q, J=7.02 Hz, 2H) 4.18-4.32 (m, 1H) 6.60 (d, J=7.42 Hz, 1H) 7.01 (d, J=8.98 Hz, 2H) 7.54 (dd, J=8.78, 1.56 Hz, 2H) 7.82 (d, J=6.24 Hz, 1H).

Example 11

(2R)-4-[5-Fluoro-2-oxo-4-(4-propylphenyl)pyridin-1(2H)-yl]-N-hydroxy-2-methyl-2-(methylsulfonyl)butanamide

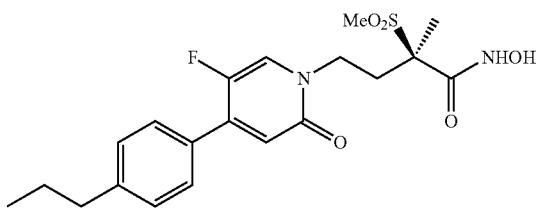

Step A) (2R)-4-[5-Fluoro-2-oxo-4-(4-propylphenyl)pyridin-1(2H)-yl]-2-methyl-2-(methylsulfonyl)-N-(tetrahydro-2H-pyran-2-yloxy)butanamide The title compound (75.5 mg, 21%) was obtained as a solid from (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (360 mg, 0.697 mmol) and (4-propylphenyl)boronic acid (171 mg, 1.04 mmol) using a procedure analogous to that described for ethyl (2R)-4-{5-fluoro-4-[4-(methylthio)phenyl]-2-oxopyridin-1(2H)-yl}-2-methyl-2-(methylsulfonyl)butanoate, Example 9, Step A. MS (LCMS) m/z 507.4 (M−1).

Step B) (2R)-4-[5-Fluoro-2-oxo-4-(4-propylphenyl)pyridin-1(2H)-yl]-N-hydroxy-2-methyl-2-(methylsulfonyl)butanamide The title compound (58 mg, 94%) was obtained as a solid from (2R)-4-[5-fluoro-2-oxo-4-(4-propylphenyl)pyridin-1(2H)-yl]-2-methyl-2-(methylsulfonyl)-N-(tetrahydro-2H-pyran-2-yloxy)butanamide (75 mg, 0.15 mmol) using a procedure analogous to that described for (2R)-4-{5-fluoro-4-[4-(methylthio)phenyl]-2-oxopyridin-1(2H)-yl}-N-hydroxy-2-methyl-2-(methylsulfonyl)butanamide, Example 9, Step D. MS (LCMS) m/z 425.2 (M+1). $^1$H NMR (400 MHz, METHANOL-d$_4$) δ ppm 0.89-1.00 (m, 3H) 1.57-1.76 (m, 5H) 2.29-2.45 (m, 1H) 2.55-2.69 (m, 3H) 3.09 (s, 3H) 3.86-4.04 (m, 1H) 4.17-4.34 (m, 1H) 6.63 (d, J=7.02 Hz, 1H) 7.31 (d, J=8.00 Hz, 2H) 7.44-7.55 (m, 2H) 7.85 (d, J=5.85 Hz, 1H).

Example 12

(2R)-4-{5-Fluoro-2-oxo-4-[4-(pentafluoro-6λ-sulfanyl)phenyl]pyridin-1(2H)-yl}-N-hydroxy-2-methyl-2-(methylsulfonyl)butanamide

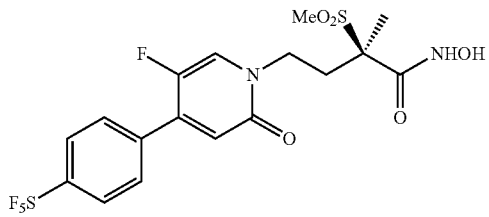

Step A) (2R)-4-{5-Fluoro-2-oxo-4-[4-(pentafluoro-6λ-sulfanyl)phenyl]pyridin-1(2H)-yl}-2-methyl-2-(methylsulfonyl)-N-(tetrahydro-2H-pyran-2-yloxy)butanamide 1,4-Dioxane was added to 1-bromo-4-(pentafluoro-6λ-sulfanyl)benzene (500 mg, 1.77 mmol), 4,4,4',4',5,5,5',5'-octamethyl-2,2'-bi-1,3,2-dioxaborolane (628 mg, 2.47 mmol), potassium acetate (347 mg, 3.53 mmol) and Pd(dppf)Cl$_2$ (130 mg, 0.177 mmol). The mixture was heated to 80° C. and stirred at this temperature for 3 h. (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (456 mg, 0.883 mmol) and aq Na$_2$CO$_3$ (2.0 N, 1.77 mL, 3.53 mmol) were added and the reaction was stirred at 80° C. overnight. The mixture was diluted with EtOAc and washed with brine. The organics were dried (MgSO$_4$), filtered, and concentrated. The crude residue was purified via flash chromatography using a 40 g silica column and an eluent of EtOAc in n-heptane (0-100%) to afford the title compound (205 mg, 39.2%). MS (LCMS) m/z 591.4 (M−1).

Step B) (2R)-4-{5-Fluoro-2-oxo-4-[4-(pentafluoro-6λ-sulfanyl)phenyl]pyridin-1(2H)-yl}-N-hydroxy-2-methyl-2-(methylsulfonyl)butanamide Aqueous HCl (1.0 M) was added to a solution of (2R)-4-{5-fluoro-2-oxo-4-[4-(pentafluoro-6λ-sulfanyl)phenyl]pyridin-1(2H)-yl}-2-methyl-2-(methylsulfonyl)-N-(tetrahydro-2H-pyran-2-yloxy)butanamide (81 mg, 0.14 mmol) and the reaction was stirred at rt overnight. The reaction was concentrated in vacuo to afford the title compound as a solid (70 mg, 100%). MS (LCMS) m/z 509.1 (M+1). $^1$H NMR (400 MHz, DMSO-d$_6$) δ ppm 1.58 (s, 3H) 2.06-2.26 (m, 1H) 3.11 (s, 3H) 3.70-3.89 (m, 1H) 3.97-4.14 (m, 1H) 6.64 (d, J=7.41 Hz, 1H) 7.81 (d, 2H) 8.04 (d, J=8.78 Hz, 2H) 8.11 (d, J=6.44 Hz, 1H).

Example 13

(2R)-4-[5-Fluoro-4-(3-methylphenyl)-2-oxopyridin-1(2H)-yl]-N-hydroxy-2-methyl-2-(methylsulfonyl)butanamide

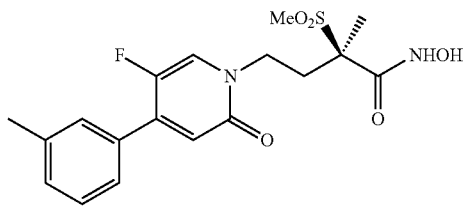

Step A) (2R)-4-[5-Fluoro-4-(3-methylphenyl)-2-oxopyridin-1(2H)-yl]-2-methyl-2-(methylsulfonyl)-N-(tetrahydro-2H-pyran-2-yloxy)butanamide The title compound (510 mg, 55%) was obtained as a gum from (3-methylphenyl)boronic acid (384 mg, 2.82 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, Example 1, Step B. MS (LCMS) m/z 479.4 (M−1).

Step B) (2R)-4-[5-Fluoro-4-(3-methylphenyl)-2-oxopyridin-1(2H)-yl]-N-hydroxy-2-methyl-2-(methylsulfonyl)butanamide The title compound (255 mg, 61%) was obtained as a solid from (2R)-4-[5-fluoro-4-(3-methylphenyl)-2-oxopyridin-1(2H)-yl]-2-methyl-2-(methylsulfonyl)-N-(tetrahydro-2H-pyran-2-yloxy)butanamide (510 mg, 1.06 mmol) using a procedure analogous to that described for (2R)-4-{5-fluoro-4-[4-(methylthio)phenyl]-2-oxopyridin-1(2H)-yl}-N-hydroxy-2-methyl-2-(methylsulfonyl)butanamide, Example 9, Step D. MS (LCMS) m/z 397.1 (M+1). $^1$H NMR (400 MHz, METHANOL-d$_4$) δ ppm 1.70 (s, 3H) 2.28-2.44 (m, 4H) 2.62 (dd, J=10.44, 5.37 Hz, 1H) 3.09 (s, 3H) 3.96 (ddd, J=12.98, 10.63, 5.46 Hz, 1H) 4.19-4.35 (m, 1H) 6.64 (d, J=7.22 Hz, 1H) 7.27-7.45 (m, 4H) 7.88 (d, J=5.85 Hz, 1H).

Example 14

(2R)-4-[5-Fluoro-4-(4-fluoro-3-methylphenyl)-2-oxopyridin-1(2H)-yl]-N-hydroxy-2-methyl-2-(methylsulfonyl)butanamide

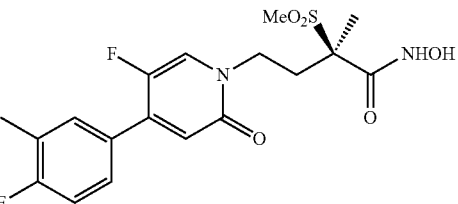

Step A) (2R)-4-[5-Fluoro-4-(4-fluoro-3-methylphenyl)-2-oxopyridin-1(2H)-yl]-2-methyl-2-(methylsulfonyl)-N-(tetrahydro-2H-pyran-2-yloxy)butanamide The title compound (360 mg, 38%) was obtained as a gum from (4-fluoro-3-methylphenyl)boronic acid (434 mg, 2.82 mmol) using a procedure analogous to that described for (2R)-4-{5-fluoro-2-oxo-4-[4-(2H-tetrazol-2-yl)phenyl]pyridin-1(2H)-yl}-2-methyl-2-(methylsulfonyl)-N-(tetrahydro-2H-pyran-2-yloxy)butanamide, Example 1, Step B. MS (LCMS) m/z 497.0 (M−1).

Step B) (2R)-4-[5-Fluoro-4-(4-fluoro-3-methylphenyl)-2-oxopyridin-1(2H)-yl]-N-hydroxy-2-methyl-2-(methylsulfonyl)butanamide The title compound (271 mg, 91%) was obtained as a white solid from (2R)-4-[5-fluoro-4-(4-fluoro-3-methylphenyl)-2-oxopyridin-1(2H)-yl]-2-methyl-2-(methylsulfonyl)-N-(tetrahydro-2H-pyran-2-yloxy)butanamide (360 mg, 0.722 mmol) using a procedure analogous to that described for (2R)-4-{5-fluoro-4-[4-(methylthio)phenyl]-2-oxopyridin-1(2H)-yl}-N-hydroxy-2-methyl-2-(methylsulfonyl)butanamide, Example 9, Step D. MS (LCMS) m/z 415.1 (M+1). $^1$H NMR (400 MHz, DMSO-d$_6$) δ ppm 1.54 (s, 3H) 2.13 (ddd, J=13.12, 11.17, 4.98 Hz, 1H) 2.26 (s, 3H) 2.40-2.45 (m, 1H) 3.08 (s, 3H) 3.75 (td, J=11.85, 5.17 Hz, 1H) 4.02 (td, J=11.85, 4.98 Hz, 1H) 6.49 (d, J=7.61 Hz, 1H) 7.20-7.28 (m, 1H) 7.38-7.45 (m, 1H) 7.50 (d, J=7.41 Hz, 1H) 8.01 (d, J=6.63 Hz, 1H).

Example 15

5-Fluoro-1-[(3R)-3-(hydroxyamino)-3-(methylsulfonyl)butyl]-4-[4-(oxetan-3-yloxy)phenyl]pyridin-2(1H)-one

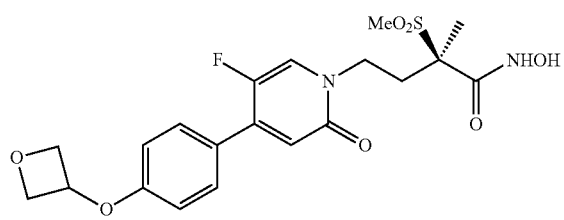

Step A) 3-(4-Bromophenoxy)oxetane

4-Bromophenol (2.5 g, 14.5 mmol) and K₂CO₃ (5.45 g, 39.4 mmol) were added to a solution of oxetan-3-yl 4-methylbenzenesulfonate (3.00 g, 13.1 mmol) in DMF (10 mL) in a sealed tube. The reaction was heated to 100° C. and stirred at this temperature for 24 h. The reaction was diluted with EtOAc and washed with water. The organic layer was dried (MgSO₄), filtered and concentrated to afford the title compound. MS (GCMS) m/z 228. This material was used in subsequent steps without further purification.

Step B) 4,4,5,5-Tetramethyl-2-[4-(oxetan-3-yloxy)phenyl]-1,3,2-dioxaborolane The title compound (3.11 g, 86%) was obtained from 3-(4-bromophenoxy)oxetane (3.00 g, 13.1 mmol) using a procedure analogous to that described for 2-[4-(4,4,5,5-tetramethyl-1,3,2-dioxaborolan-2-yl)phenyl]-2H-tetrazole, Example 1, Step A. MS (GCMS) m/z 276. $^1$H NMR (400 MHz, CHLOROFORM-d) δ ppm 1.31 (s, 12H) 4.70-4.79 (m, 2H) 4.91-5.00 (m, 2H) 5.18-5.27 (m, 1H) 6.67 (d, J=8.78 Hz, 2H) 7.73 (d, J=8.78 Hz, 2H).

Step C) 5-Fluoro-1-{(3R)-3-(methylsulfonyl)-3-[(tetrahydro-2H-pyran-2-yloxy)amino]butyl}-4-[4-(oxetan-3-yloxy)phenyl]pyridin-2(1H)-one 1,4-Dioxane (20 mL) and water (5 mL) were added to a flask containing (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3 (287 mg, 0.56 mmol), 4,4,5,5-tetramethyl-2-[4-(oxetan-3-yloxy)phenyl]-1,3,2-dioxaborolane (301 mg, 1.09 mmol), Pd(PPh₃)₄ (65 mg, 0.06 mmol), and potassium carbonate (230 mg, 1.67 mmol), which was previously flushed with N₂. The mixture was heated to 80° C. and stirred at that temperature overnight. The reaction was concentrated and purified via flash chromatography using two 12 g silica gel columns. The first column was eluted with methanol in dichloromethane (0-20%). The second column was eluted with EtOAc in n-heptane (0-100%) followed by methanol in dichloromethane (0-20%) to afford the title compound as a solid (164 mg, 54%). MS (LCMS) m/z 537.4 (M−1).

Step D) 5-Fluoro-1-[(3R)-3-(hydroxyamino)-3-(methylsulfonyl)butyl]-4-[4-(oxetan-3-yloxy)phenyl]pyridin-2(1H)-one Trifluoroacetic acid (1 mL) was added to a solution of 5-fluoro-1-{(3R)-3-(methylsulfonyl)-3-[(tetrahydro-2H-pyran-2-yloxy)amino]butyl}-4-[4-(oxetan-3-yloxy)phenyl]pyridin-2(1H)-one (164 mg, 0.304 mmol) in DCM (10 mL). The reaction was allowed to stir at rt overnight and then concentrated under vacuum. The residue was re-dissolved in dichloromethane and n-heptane and concentrated again to afford the title compound as a solid. (113 mg, 82%). MS (LCMS) m/z 455.1 (M+1). $^1$H NMR (400 MHz, METHANOL-d₄) δ ppm 1.69 (s, 3H) 2.35 (ddd, J=13.66, 10.63, 5.17 Hz, 1H) 2.53-2.67 (m, 1H) 3.09 (s, 3H) 3.91 (ddd, J=12.98, 10.63, 5.27 Hz, 1H) 4.16-4.30 (m, 1H) 4.69 (dd, J=7.51, 4.78 Hz, 2H) 5.02 (t, J=6.73 Hz, 2H) 5.33 (t, J=5.46 Hz, 1H) 6.58 (d, J=7.42 Hz, 1H) 6.85-6.91 (m, 2H) 7.55 (dd, J=8.68, 1.85 Hz, 2H) 7.80 (d, J=6.24 Hz, 1H).

Example 16

(2R)-4-[4-(4-Chloro-2-fluorophenyl)-5-fluoro-2-oxopyridin-1(2H)-yl]-N-hydroxy-2-methyl-2-(methylsulfonyl)butanamide

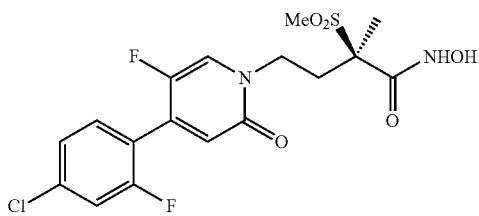

Step A) (2R)-4-[4-(4-Chloro-2-fluorophenyl)-5-fluoro-2-oxopyridin-1(2H)-yl]-2-methyl-2-(methylsulfonyl)butanoic acid To a 3 L flask with mechanical stirring was added ethyl (2R)-4-(5-fluoro-4-iodo-2-oxopyridin-1(2H)-yl)-2-methyl-2-(methylsulfonyl)butanoate, T2 (100 g, 225 mmol), (4-chloro-2-fluorophenyl)boronic acid (25.5 g, 146 mmol) and Pd(dppf)₂Cl₂ (4.93 g, 6.74 mmol). The flask was purged with N₂, then degassed 2-methyltetrahydrofuran (1 L) and 3 M aq K₃PO₄ (225 mL, 674 mmol) were added. The reaction mixture was heated to 75° C. and stirred at this temperature for 30 min. Additional (4-chloro-2-fluorophenyl)boronic acid (25.5 g, 146 mmol) was added and the reaction was allowed to heat for 1.5 h. The mixture was allowed to cool to rt and the aqueous layer was separated. The organic layer was passed through a celite pad and placed back in the reaction vessel. Lithium hydroxide (28 g, 667 mmol) in water (700 mL) was added and the mixture was heated to 50° C. and stirred at this temperature for 1 h. The mixture was allowed to cool and the aqueous layer separated. Celite was added to the aqueous layer and the mixture was filtered through a plug of celite. The filtrate was placed in a flask with overhead stirrer and carefully acidified with 4 M aq HCl and heated to 50° C. with stirring until a precipitate formed. The solid was collected via filtration and dried under vacuum to afford the title compound as a tan solid (68.7 g, 74%). MS (LCMS) m/z 420.6 (M+1). $^1$H NMR (400 MHz, DMSO-d₆) δ ppm 1.54 (s, 3H) 2.18 (ddd, J=13.17, 10.24, 5.07 Hz, 1H) 2.41-2.45 (m, 1H) 3.10-3.19 (s, 3H) 3.87-4.08 (m, 2H) 6.47 (d, J=7.02 Hz, 1H) 7.42 (dd, J=8.39, 1.95 Hz, 1H) 7.48-7.56 (m, 1H) 7.60 (dd, J=9.95, 1.95 Hz, 1H) 8.06 (d, J=6.05 Hz, 1H).

Step B) (2R)-4-[4-(4-Chloro-2-fluorophenyl)-5-fluoro-2-oxopyridin-1(2H)-yl]-2-methyl-2-(methylsulfonyl)-N-(tetrahydro-2H-pyran-2-yloxy)butanamide N-Methylmorpholine (54 mL, 491 mmol) and 2-chloro-4,6-dimethoxy-1,3,5-triazine (43.1 g, 245 mmol) were added to a solution of (2R)-4-[4-(4-chloro-2-fluorophenyl)-5-fluoro-2-oxopyridin-1(2H)-yl]-2-methyl-2-(methylsulfonyl)butanoic acid (68.7 g, 164 mmol) in 2-methyltetrahydrofuran (1 L) and the reaction was stirred at rt for 2 h. O-(Tetrahydro-2H-pyran-2-yl)hydroxylamine (28.8 g, 245 mmol) was added and the reaction was allowed to stir at rt for 1 h. The mixture was filtered and the filtrate was concentrated. The crude residue was purified via column chromatography using silica gel and eluting with 40% EtOAc in n-heptane (4 L) and EtOAc (6 L). The desired fractions were combined and concentrated to afford the title compound as a white gummy solid. (74.82 g, 88%). MS (LCMS) m/z 517.9 (M−1).

Step C) (2R)-4-[4-(4-Chloro-2-fluorophenyl)-5-fluoro-2-oxopyridin-1(2H)-yl]-N-hydroxy-2-methyl-2-(methylsulfonyl)butanamide Water (312 mL) and 1 N aq HCl (23.9 mL, 23.9 mmol) were added to a solution of (2R)-4-[4-(4-chloro-2-fluorophenyl)-5-fluoro-2-oxopyridin-1(2H)-yl]-2-methyl-2-(methylsulfonyl)-N-(tetrahydro-2H-pyran-2-yloxy)butanamide (74.7 g, 144.1 mmol) in ethanol (126 mL). The reaction was heated to 70° C. and stirred at this temperature overnight. The reaction was allowed to cool and the solid was collected via filtration and washed with water until the filtrate had a pH of ~5. The solid was dried under vacuum to afford the title compound as a white solid (46.48 g, 74%). MS (LCMS) m/z 435.6 (M+1). $^1$H NMR (400 MHz, DMSO-$d_6$) δ ppm 1.56 (s, 3H) 2.09-2.21 (m, 1H) 2.44 (d, J=5.27 Hz, 1H) 3.10 (s, 3H) 3.77 (td, J=11.90, 5.07 Hz, 1H) 4.04 (td, J=11.95, 4.98 Hz, 1H) 6.51 (d, J=7.02 Hz, 1H) 7.44 (dd, J=8.29, 2.05 Hz, 1H) 7.50-7.56 (m, 1H) 7.62 (dd, J=9.95, 1.95 Hz, 1H) 8.04 (d, J=5.85 Hz, 1H) 9.22 (s, 1H) 11.05 (s, 1H).

Example 17

(2R)-4-[5-fluoro-4-(2-fluoro-3-methoxyphenyl)-2-oxopyridin-1(2H)-yl]-N-hydroxy-2-methyl-2-(methylsulfonyl)butanamide

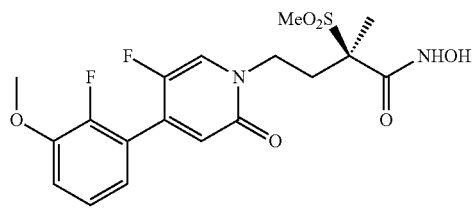

Step A) (2R)-4-[5-Fluoro-4-(2-fluoro-3-methoxyphenyl)-2-oxopyridin-1(2H)-yl]-2-methyl-2-(methylsulfonyl)butanoic acid 1,1'-Bis(diphenylphosphino)ferrocene-palladium(II) dichloride dichloromethane complex (5.90 g, 7.22 mmol) was added to a mixture of ethyl (2R)-4-(5-fluoro-4-iodo-2-oxopyridin-1(2H)-yl)-2-methyl-2-(methylsulfonyl)butanoate, T2 (29.63 g, 66.55 mmol), (2-fluoro-3-methoxyphenyl)boronic acid (18.50 g, 108.9 mmol) and potassium phosphate tribasic (54.5 g, 205 mmol) in 2-methyltetrahydrofuran (450 mL) and 113 deionized water (225 mL). The mixture was heated to 60° C. and stirred at this temperature overnight. The reaction was allowed to cool to rt. The aqueous layer was separated from the organics and the organics were washed with water (200 mL) and brine (200 mL), dried (MgSO$_4$), and filtered. Darco® G-60-100 mesh, powder was added to the filtrate and was stirred for 1 h. Solids were removed via filtration over celite and the filtered pad was washed with EtOAc (~300 mL). The combined filtrates were concentrated to afford a red oil (30.62 g). The oil was dissolved in 2-methyltetrahydrofuran (450 mL) and deionized water (225 mL). Potassium hydroxide (26.1 g, 465 mmol) was added to the mixture and the reaction was heated to 50° C. and stirred at this temperature overnight. The reaction was allowed to cool to rt. The aqueous layer was separated and washed with diethyl ether (2×200 mL). The aqueous layer was slowly acidified while stirring using concentrated HCl to a pH of 1 and the suspension was stirred for 1 h. The suspension was filtered and the solids were washed with water (3×100 mL) and hexanes (3×300 mL). The solids were dried in vacuo to afford the title compound as a tan solid (26.49 g, 94.54%). MS (LCMS) m/z 416.0 (M+1). $^1$H NMR (400 MHz, DMSO-$d_6$) δ ppm 1.57 (s, 3H) 2.14-2.28 (m, 0H) 2.42-2.54 (m, 1H) 3.18 (s, 3H) 3.88 (s, 3H) 3.90-4.09 (m, 2H) 6.44 (d, J=7.03 Hz, 1H) 6.92-7.04 (m, 1H) 7.20-7.36 (m, 2H) 8.06 (d, J=5.95 Hz, 1H) 13.90 (br. s., 1H).

Step B) (2R)-4-[5-Fluoro-4-(2-fluoro-3-methoxyphenyl)-2-oxopyridin-1(2H)-yl]-2-methyl-2-(methylsulfonyl)-N-(tetrahydro-2H-pyran-2-yloxy)butanamide N-Methylmorpholine (11 mL, 96.2 mmol) was added to a solution of CDMT (13.5 g, 116 mmol) and (2R)-4-[5-fluoro-4-(2-fluoro-3-methoxyphenyl)-2-oxopyridin-1(2H)-yl]-2-methyl-2-(methylsulfonyl)butanoic acid (26.49 g, 63.77 mmol) in 2-methyltetrahydrofuran (640 mL) and the reaction was stirred for 2 h. THP-hydroxylamine (13.5 g, 116 mmol) was added to the reaction and the reaction was stirred overnight at rt. The reaction was quenched with saturated aqueous sodium bicarbonate (500 mL). The organic layer was separated and washed with water (300 mL) and brine (300 mL), then dried (MgSO$_4$), and filtered. Darco G-60, -100 mesh, powder was added to the filtrate and the suspension was stirred for 1 h. The charcoal was removed via filtration through a celite pad and the filter pad was washed with EtOAc (1 L). The filtrate was concentrated to afford the title compound as a yellowish-white solid (30.49, 92.93%). MS (LCMS) m/z 513.9 (M−1).

Step C) (2R)-4-[5-Fluoro-4-(2-fluoro-3-methoxyphenyl)-2-oxopyridin-1(2H)-yl]-N-hydroxy-2-methyl-2-(methylsulfonyl)butanamide Pyridinium p-toluenesulfonate (190 mg, 0.76 mmol) was added to a solution of (2R)-4-[5-fluoro-4-(2-fluoro-3-methoxyphenyl)-2-oxopyridin-1(2H)-yl]-2-methyl-2-(methylsulfonyl)-N-(tetrahydro-2H-pyran-2-yloxy)butanamide (777 mg, 1.51 mmol) in ethanol (15 mL). The reaction was heated to 50° C. and stirred at this temperature overnight. Additional pyridinium p-toluenesulfonate (118 mg, 0.47 mmol) was added to the solution and the reaction was heated at 60° C. for 3 h. The reaction was allowed to cool to rt and the precipitate was collected via filtration. The solid was washed with ethanol (15 mL) and hexanes (15 mL) and dried in vacuo to afford the title compound as a white solid (413 mg, 63.5%). MS (LCMS) m/z 431.0 (M+1). $^1$H NMR (400 MHz, DMSO-d$_6$) δ ppm 1.57 (s, 1H) 2.08-2.25 (m, 0H) 2.41-2.56 (m, 1H) 3.02-3.19 (m, 3H) 3.71-3.85 (m, 1H) 3.88 (s, 3H) 3.98-4.13 (m, 1H) 6.47 (d, J=7.02 Hz, 1H) 6.93-7.08 (m, 1H) 7.19-7.36 (m, 2H) 8.04 (d, J=5.66 Hz, 1H) 9.24 (d, J=1.56 Hz, 1H) 11.07 (d; J=1.56 Hz, 1H).

Example 18

(2R)-4-[5-Fluoro-4-{4-[(trans-4-hydroxycyclohexyl)methoxy]phenyl}-2-oxopyridin-1(2H)-yl]-N-hydroxy-2-methyl-2-(methylsulfonyl)butanamide

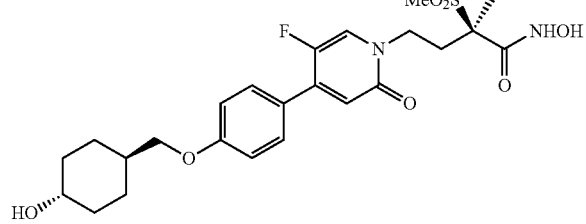

Step A) Ethyl 4-(tetrahydro-2H-pyran-2-yloxy)cyclohexanecarboxylate

Pyridinium-4-toluenesulfonate (2.57 g, 10.2 mmol) was added to a solution of ethyl 4-hydroxycyclohexanecarboxylate (8.8 g, 51.10 mmol) and 3,4-dihydro-2H-pyran (8.60 g, 102 mmol) in DCM (200 mL) and the reaction was stirred at rt for 16 h. The reaction was quenched with saturated aq NaHCO$_3$. The layers were separated and the organic layer was washed with water. The organic layer was dried (Na$_2$SO$_4$), filtered, and concentrated. Purification via flash chromatography on a 200 g silica column using an eluent of EtOAc in hexanes (5-10%) afforded the title compound as a clear oil (11.1 g, 85%).

Step B) [cis-4-(Tetrahydro-2H-pyran-2-yloxy)cyclohexyl]methanol and (+/−)-[trans-4-(tetrahydro-2H-pyran-2-yloxy)cyclohexyl]methanol Sodium borohydride (3.69 g, 97.5 mmol) was added to a solution of ethyl 4-(tetrahydro-2H-pyran-2-yloxy)cyclohexanecarboxylate (2.50 g, 9.75 mmol) in ethanol (100 mL) at 0° C. The reaction was allowed to warm to rt as the ice bath expired. After 2 days the reaction was cooled to 0° C. and quenched by the addition of 1 N aq HCl until the effervescence ceased, pH 5-6. The reaction was concentrated and the resulting residue was partitioned between EtOAc and water. The layers were separated, and the aqueous layer was extracted with EtOAc. The organic layers were combined, dried (MgSO$_4$), filtered, and concentrated. Purification on a silica gel 100 g column and an eluent of EtOAc in hexanes (10-40%) afforded the two sets of enantiomers as clear oils.

(+/−)-[cis-4-(tetrahydro-2H-pyran-2-yloxy)cyclohexyl]methanol (387 mg, 18%)

$^1$H NMR (400 MHz, CHLOROFORM-d) δ ppm 1.30-1.65 (m, 12H) 1.64-1.76 (m, 1H) 1.76-1.94 (m, 3H) 3.33-3.64 (m, 3H) 3.80-4.01 (m, 2H) 4.59-4.75 (m, 1H).

(+/−)-[trans-4-(tetrahydro-2H-pyran-2-yloxy)cyclohexyl]methanol (824, 39.4%)

$^1$H NMR (400 MHz, CHLOROFORM-d) δ ppm 0.86-1.11 (m, 2H) 1.16-1.31 (m, 1H) 1.31-1.64 (m, 7H) 1.64-1.77 (m, 1H) 1.78-1.93 (m, 3H) 1.99-2.14 (m, 2H) 3.35-3.67 (m, 4H) 3.80-4.04 (m, 1H) 4.63-4.79 (m, 1H).

Step C) 2-[(trans-4-{[4-(4,4,5,5-Tetramethyl-1,3,2-dioxaborolan-2-yl)phenoxy]methyl}cyclohexyl)oxy]tetrahydro-2H-pyran Diisopropyl azodicarboxylate (2.1 mL, 10.5 mmol) was added to a solution of [trans-4-(tetrahydro-2H-pyran-2-yloxy)cyclohexyl]methanol (2.05 g, 9.57 mmol), 4-(4,4,5,5-tetramethyl-1,3,2-dioxaborolan-2-yl)phenol (2.3 g, 10.7 mmol), triphenylphosphine (2.76 g, 10.5 mmol), and triethylamine (1.5 mL, 10.5 mmol) in THF (150 mL) at 0° C. The reaction was allowed to warm to it and stirred overnight. Water (200 mL) was added and the reaction was extracted with EtOAc (600 mL). The organics were washed with 1 M aq NaOH (4×100 mL), brine, then dried (Na$_2$SO$_4$), filtered and concentrated under reduced pressure. The crude residue was purified via flash chromatography using an eluent of 20% EtOAc in hexanes to afford the title compound as a white solid (1.9 g, 48%). MS (APCI) m/z 417.3 (M+1).

Step D) Ethyl (2R)-4-[5-fluoro-2-oxo-4-(4-{[trans-4-(tetrahydro-2H-pyran-2-yloxy)cyclohexyl]methoxy}phenyl)pyridin-1(2H)-yl]-2-methyl-2-(methylsulfonyl)butanoate Pd(dppf)Cl$_2$ (350 mg, 0.431 mmol) was added to a solution of ethyl (2R)-4-(5-fluoro-4-iodo-2-oxopyridin-1(2H)-yl)-2-methyl-2-(methylsulfonyl)butanoate (1.6 g, 3.6 mmol), 2-[(trans-4-{[4-(4,4,5,5-tetramethyl-1,3,2-dioxaborolan-2-yl)phenoxy]methyl}cyclohexyl)oxy]tetrahydro-2H-pyran (1.9 g, 4.49 mmol), and potassium phosphate tribasic (2.9 g, 10.8 mmol) in 2-methyl tetrahydrofuran/water (5:1, 240 mL). The reaction mixture was heated to 80° C. and stirred at this temperature for 16 h. The reaction was allowed to cool to rt, and water (50 mL) was added. The mixture was extracted with EtOAc (3×150 mL). The combined organic phases were dried (Na$_2$SO$_4$), filtered, and concentrated under reduced pressure to afford the title compound as a light tan solid (1.4 g, 64%). MS (LCMS) m/z 608.2 (M+1).

Step E) (2R)-4-[5-Fluoro-2-oxo-4-(4-{[trans-4-(tetrahydro-2H-pyran-2-yloxy)cyclohexyl]methoxy}phenyl)pyridin-1(2H)-yl]-2-methyl-2-(methylsulfonyl)butanoic acid Aqueous lithium hydroxide (2.0 M, 5.8 mL, 2.3 mmol) was added to a solution of ethyl (2R)-4-[5-fluoro-2-oxo-4-(4-{[trans-4-(tetrahydro-2H-pyran-2-yloxy)cyclohexyl]methoxy}-phenyl)pyridin-1(2H)-yl]-2-methyl-2-(methylsulfonyl)butanoate (1.4 g, 2.3 mmol) in ethanol (40 mL). The reaction was heated to 50° C. for 3 h. The reaction was allowed to cool to ambient temperature and then acidified to a pH of ~3 with 1.0 N aq. HCl. The mixture was extracted with EtOAc (3×150 mL). The combined organic phases were dried (Na$_2$SO$_4$), filtered, and concentrated under reduced pressure to afford the title compound as a white solid (1.28 g, 98%). MS (LCMS) m/z 580.3 (M+1).

Step F) (2R)-4-[5-Fluoro-2-oxo-4-(4-{[trans-4-(tetrahydro-2H-pyran-2-yloxy)cyclohexyl]methoxy}phenyl)pyridin-1(2H)-yl]-2-methyl-2-(methylsulfonyl)-N-(tetrahydro-2H-pyran-2-yloxy)butanamide N-Methyl morpholine (340 uL, 3.09 mmol) was added to a suspension of (2R)-4-[5-fluoro-2-oxo-4-(4-{[trans-4-(tetrahydro-2H-pyran-2-yloxy)cyclohexyl]methoxy}-phenyl)pyridin-1(2H)-yl]-2-methyl-2-(methylsulfonyl)butanoic acid (1.28 g, 2.21 mmol), 2-chloro-4,6-dimethoxy-1,3,5-triazine (510 mg, 2.87 mmol) in 2-methyltetrahydrofuran (30 mL) and the reaction was stirred for 1 h at rt. O-(Tetrahydro-2H-pyran-2-yl)hydroxylamine (61 mg, 0.52 mmol) was added, and the reaction was stirred overnight at rt. Water (50 mL) was added, and the mixture was extracted with EtOAc (3×150 mL). The combined organic phases were dried ($Na_2SO_4$), filtered, and concentrated under reduced pressure. The crude material was purified via flash chromatography using an eluent of EtOAc in n-heptane (75-100%) to afford the title compound as a light brown residue (700 mg, 46%). MS (LCMS) m/z 677.4 (M+1).

Step G) (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide Hydrochloric acid (4.0 M in 1,4-dioxane, 1.7 mL, 6.63 mmol) was added to a solution of (2R)-4-[5-fluoro-2-oxo-4-(4-{[trans-4-(tetrahydro-2H-pyran-2-yloxy)cyclohexyl]methoxy}phenyl)-pyridin-1(2H)-yl]-2-methyl-2-(methylsulfonyl)-N-(tetrahydro-2H-pyran-2-yloxy)butanamide (450 mg, 0.66 mmol) in 1,4-dioxane:DCM:water (2:2:1, 5 mL) at room temperature. After 1 h, the reaction was concentrated under reduced pressure. The crude residue was triturated in ethanol (10 mL) overnight. The solid was collected via filtration, washed with ethanol (5 mL), and dried under reduced pressure to afford the title compound as a white solid (110 mg, 33%). MS (LCMS) m/z 511.1 (M+1). $^1$H NMR (400 MHz, DMSO-$d_6$) δ ppm 0.97-1.19 (m, 4H) 1.54 (s, 3H) 1.58-1.72 (m, 1H) 1.72-1.89 (m, 4H) 2.04-2.23 (m, 1H) 2.41 (m, 1H) 3.08 (s, 3H) 3.18-3.40 (m, 1H) 3.65-3.84 (m, 3H) 4.01 (td, J=11.61, 4.88 Hz, 1H) 4.49 (br. s., 1H) 6.45 (d, J=7.81 Hz, 1H) 6.94-7.06 (m, 2H) 7.36-7.54 (m, 2H) 7.96 (d, J=6.83 Hz, 1H) 9.21 (s, 1H) 11.07 (s, 1H) 11.12 (s, 1H).

Example 19

(2R)-4-[5-Fluoro-4-(3-fluoro-4-methoxyphenyl)-2-oxopyridin-1(2H)-yl]-N-hydroxy-2-methyl-2-(methylsulfonyl)butanamide

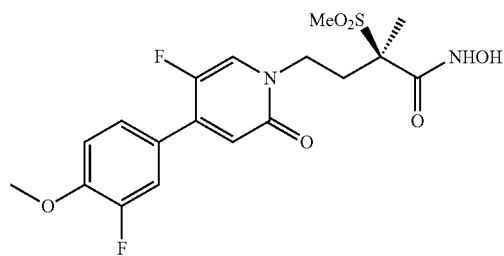

Step A) (2R)-4-[5-Fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide Pd Encat™ (580 mg, 0.17 mmol) was added to a mixture of potassium carbonate (723 mg, 5.2 mmol), (3-fluoro-4-methoxyphenyl)boronic acid (318 mg, 2.1 mmol), and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (900 mg, 1.7 mmol) in 1,4-dioxane:water (5:1, 24 mL). The reaction was heated to 80° C. and allowed to stir at this temperature overnight. The reaction was filtered through a pad of celite, which was washed with methanol (250 mL). The filtrate was concentrated under reduced pressure, and the resulting crude material was purified via flash chromatography using an eluent of EtOAc in heptanes (20-100%), then 10% methanol in EtOAc to provide the title compound as a light tan residue (800 mg, 99%). MS (LCMS) m/z 495.1 (M−1).

Step B) (2R)-4-[5-Fluoro-4-(3-fluoro-4-methoxyphenyl)-2-oxopyridin-1(2H)-yl]-N-hydroxy-2-methyl-2-(methylsulfonyl)butanamide The title compound (400 mg, 58%) was obtained as a solid from (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide (800 mg, 1.65 mmol) using a procedure analogous to that described for the preparation of (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide, Example 18, Step G. MS (LCMS) m/z 413.1 (M+1). $^1$H NMR (400 MHz, DMSO-$d_6$) δ ppm 1.54 (s, 3H) 2.06-2.18 (m, 1H) 2.38-2.47 (m, 1H) 3.08 (s, 3H) 3.74 (td, J=12.00, 4.88 Hz, 1H) 3.87 (s, 3H) 4.02 (td, J=11.85, 4.98 Hz, 1H) 6.52 (d, J=7.81 Hz, 1H) 7.21-7.31 (m, 1H) 7.34-7.51 (m, 2H) 7.99 (d, J=6.83 Hz, 1H) 9.20 (s, 1H) 11.06 (br. s, 1H).

Example 20

(2R)-4-[5-Fluoro-2-oxo-4-(4-pyrimidin-2-ylphenyl)pyridin-1(2H)-yl]-N-hydroxy-2-methyl-2-(methylsulfonyl)butanamide

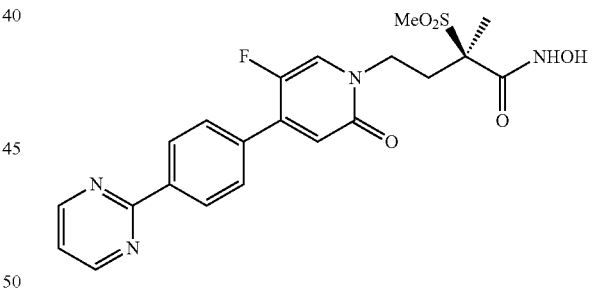

Step A) 2-[4-(4,4,5,5-Tetramethyl-1,3,2-dioxaborolan-2-yl)phenyl]pyrimidine

A degassed solution of 2-bromopyrimidine (1.5 g, 9.4 mmol), 2,2'-(1,4-phenylene)bis(4,4,5,5-tetramethyl-1,3,2-dioxaborolane) (5.1 g, 16.0 mmol), 1.0 M aq $K_3PO_4$ (28.3 mL, 28.3 mmol), and Pd(PPh$_3$)$_4$ (330 mg, 0.31 mmol) in DMF (140 mL) was heated to 80° C. and stirred at this temperature for 16 h. Water (100 mL) was added to the reaction mixture and was extracted with EtOAc (3×200 mL). The combined organic phases were dried ($Na_2SO_4$), filtered, and concentrated under reduced pressure. The crude material was purified via flash chromatography using an eluent of 17% EtOAc in n-heptane to afford the title compound as a white solid (0.7 g, 28%). MS (LCMS) m/z 283.1 (M+1). $^1$H NMR (400 MHz, CHLOROFORM-d) δ ppm 1.36 (s, 12H) 7.19 (t, J=4.68 Hz, 1H) 7.93 (d, J=8.00 Hz, 2H) 8.43 (d, J=7.81 Hz, 2H) 8.81 (d, J=4.68 Hz, 2H).

Step B) Ethyl (2R)-4-[5-Fluoro-2-oxo-4-(4-pyrimidin-2-ylphenyl)pyridin-1(2H)-yl]-2-methyl-2-(methylsulfonyl)butanoate The title compound (278 mg, 87%) was obtained as a light tan solid from 2-[4-(4,4,5,5-tetramethyl-1,3,2-dioxaborolan-2-yl)phenyl]pyrimidine (270 mg, 0.94 mmol) and ethyl (2R)-4-(5-fluoro-4-iodo-2-oxopyridin-1(2H)-yl)-2-methyl-2-(methylsulfonyl)butanoate, T2, (300 mg, 0.67 mmol) using a procedure analogous to that described for the preparation of ethyl (2R)-4-[5-fluoro-2-oxo-4-(4-{[trans-4-(tetrahydro-2H-pyran-2-yloxy)cyclohexyl]methoxy}phenyl)pyridin-1(2H)-yl]-2-methyl-2-(methylsulfonyl)butanoate, Example 18, Step D. MS (LCMS) m/z 474.2 (M+1).

Step C) (2R)-4-[5-Fluoro-2-oxo-4-(4-pyrimidin-2-ylphenyl)pyridin-1(2H)-yl]-2-methyl-2-(methylsulfonyl)butanoic acid The title compound (250 mg, 98%) was obtained as a light brown gum from ethyl (2R)-4-[5-fluoro-2-oxo-4-(4-pyrimidin-2-ylphenyl)pyridin-1(2H)-yl]-2-methyl-2-(methylsulfonyl)butanoate (270 mg, 0.57 mmol) using a procedure analogous to that described for the preparation of (2R)-4-[5-fluoro-2-oxo-4-(4-{[trans-4-(tetrahydro-2H-pyran-2-yloxy)cyclohexyl]methoxy}-phenyl)pyridin-1(2H)-yl]-2-methyl-2-(methylsulfonyl)butanoic acid, Example 18, Step E. MS (LCMS) m/z 446.1 (M+1). $^1$H NMR (400 MHz, METHANOL-$d_4$) δ ppm 1.73 (s, 3H) 2.39-2.51 (m, 1H) 2.62-2.75 (m, 1H) 3.17 (s, 3H) 4.20-4.46 (m, 2H) 6.86 (d, J=7.02 Hz, 1H) 7.65 (t, J=5.07 Hz, 1H) 7.83 (d, J=7.02 Hz, 2H) 8.09 (d, J=5.85 Hz, 1H) 8.53 (d, J=8.39 Hz, 2H) 9.06 (d, J=4.88 Hz, 2H).

Step D) (2R)-4-[5-Fluoro-2-oxo-4-(4-pyrimidin-2-ylphenyl)pyridin-1(2H)-yl]-2-methyl-2-(methylsulfonyl)-N-(tetrahydro-2H-pyran-2-yloxy)butanamide The title compound (290 mg, 94%) was obtained as a light brown gum from (2R)-4-[5-fluoro-2-oxo-4-(4-pyrimidin-2-ylphenyl)pyridin-1(2H)-yl]-2-methyl-2-(methylsulfonyl)butanoic acid (250 mg, 0.56 mmol) and O-(tetrahydro-2H-pyran-2-yl)hydroxylamine (87 mg, 0.74 mmol) using a procedure analogous to that described for the preparation of (2R)-4-[5-fluoro-2-oxo-4-(4-{[trans-4-(tetrahydro-2H-pyran-2-yloxy)cyclohexyl]methoxy}-phenyl)pyridin-1(2H)-yl]-2-methyl-2-(methylsulfonyl)-N-(tetrahydro-2H-pyran-2-yloxy)butanamide, Example 18, Step F. MS (LCMS) m/z 543.0 (M+1).

Step E) (2R)-4-[5-Fluoro-2-oxo-4-(4-pyrimidin-2-ylphenyl)pyridin-1(2H)-yl]-N-hydroxy-2-methyl-2-(methylsulfonyl)butanamide The title compound (80 mg, 30%) was obtained as a tan solid from (2R)-4-[5-fluoro-2-oxo-4-(4-pyrimidin-2-ylphenyl)pyridin-1(2H)-yl]-2-methyl-2-(methylsulfonyl)-N-(tetrahydro-2H-pyran-2-yloxy)butanamide (312 mg, 0.57 mmol) using a procedure analogous to that described for the preparation of (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide, Example 18, Step G. MS (LCMS) m/z 461.1 (M+1). $^1$H NMR (400 MHz, METHANOL-$d_4$) δ ppm 1.70 (s, 3H) 2.31-2.45 (m, 1H) 2.56-2.71 (m, 1H) 3.10 (s, 3H) 3.87-4.01 (m, 1H) 4.19-4.33 (m, 1H) 6.70 (d, J=7.42 Hz, 1H) 7.38 (t, J=4.88 Hz, 1H) 7.73 (dd, J=8.59, 1.76 Hz, 2H) 7.87 (d, J=6.05 Hz, 1H) 8.53 (d, J=8.59 Hz, 2H) 8.87 (d, J=4.88 Hz, 2H).

Example 21

(2R)-4-{5-Fluoro-4-[4-(5-methoxypyrimidin-2-yl)phenyl]-2-oxopyridin-1(2H)-yl}-N-hydroxy-2-methyl-2-(methylsulfonyl)butanamide

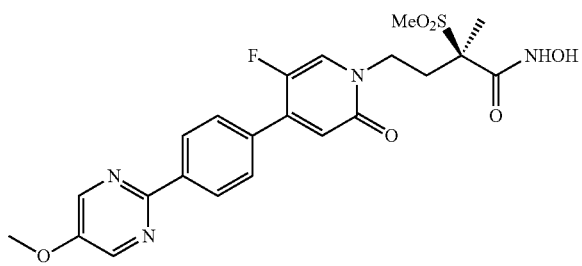

Step A) 5-Methoxy-2-[4-(4,4,5,5-tetramethyl-1,3,2-dioxaborolan-2-yl)phenyl]pyrimidine The title compound (700 mg, 17%) was obtained as a white solid from 2-chloro-5-methoxypyrimidine (1.85 g, 12.8 mmol) and 2,2'-(1,4-phenylene)bis(4,4,5,5-tetramethyl-1,3,2-dioxaborolane) (6.9 g, 21.0 mmol) using a procedure analogous to that described for the preparation of 2-[4-(4,4,5,5-tetramethyl-1,3,2-dioxaborolan-2-yl)phenyl]pyrimidine, Example 20, Step A. MS (LCMS) m/z 313.1 (M+1). $^1$H NMR (400 MHz, CHLOROFORM-d) δ ppm 1.33 (s, 12H) 3.93 (s, 3H) 7.83-7.90 (m, 2H) 8.28-8.34 (m, 2H) 8.45 (s, 2H).

Step B) (2R)-4-[5-Fluoro-4-[4-(5-methoxypyrimidin-2-yl)phenyl]-2-oxopyridin-1(2H)-yl]-2-methyl-2-(methylsulfonyl)-N-(tetrahydro-2H-pyran-2-yloxy)butanamide The title compound (900 mg, 95%) was obtained as a tan solid from 5-methoxy-2-[4-(4,4,5,5-tetramethyl-1,3,2-dioxaborolan-2-yl)phenyl]pyrimidine (719 mg, 2.3 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (850 mg, 1.65 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19 Step A. MS (LCMS) m/z 573.2 (M+1).

Step C) (2R)-4-{5-Fluoro-4-[4-(5-methoxypyrimidin-2-yl)phenyl]-2-oxopyridin-1(2H)-yl}-N-hydroxy-2-methyl-2-(methylsulfonyl)butanamide The title compound (50 mg, 6%) was obtained as a light brown solid from (2R)-4-{5-fluoro-4-[4-(5-methoxypyrimidin-2-yl)phenyl]-2-oxopyridin-1(2H)-yl}-2-methyl-2-(methylsulfonyl)-N-(tetrahydro-2H-pyran-2-yloxy)butanamide (900 mg, 1.57 mmol) using a procedure analogous to that described for the preparation of (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide, Example 18, Step G. MS (LCMS) m/z 491.1 (M+1). $^1$H NMR (400 MHz, DMSO-$d_6$) δ ppm 1.53 (s, 3H) 2.08-2.19 (m, 1H) 2.39-2.48 (m, 1H) 3.07 (s, 3H) 3.69-3.78 (m, 1H) 3.92 (s, 3H) 3.96-4.08 (m, 1H) 6.56 (d, J=7.71 Hz, 1H) 7.67 (m, J=8.70, 2.00 Hz, 2H) 8.01 (d, J=6.54 Hz, 1H) 8.34-8.38 (m, 2H) 8.64 (s, 2H) 9.19 (br. d, J=1.80 Hz, 1H) 11.04 (br. d, J=1.90 Hz, 1H).

Example 22

(2R)-4-{5-Fluoro-4-[4-(4-methoxy-2H-1,2,3-triazol-2-yl)phenyl]-2-oxopyridin-1(2H)-yl}-N-hydroxy-2-methyl-2-(methylsulfonyl)butanamide

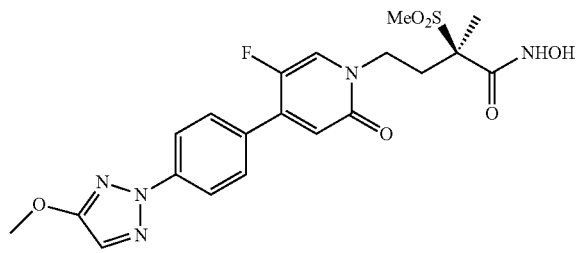

Step A)
2-(4-Bromophenyl)-4-methoxy-2H-1,2,3-triazole

Cesium carbonate (4.5 g, 13.7 mmol) was added to a solution of 2-(4-bromophenyl)-2H-1,2,3-triazol-4-ol (1.1 g, 4.6 mmol) and methyl iodide (0.36 mL, 5.7 mmol) in THF (50 mL). The reaction was heated to 60° C. and stirred at this temperature for 16 h. Water (20 mL) was added to the reaction, and the resulting mixture was extracted with EtOAc (2×150 mL). The combined organic phases were dried over potassium carbonate, filtered, and concentrated under reduced pressure to afford the title compound as a tan solid (1.1 g, 95%). $^1$H NMR (400 MHz, METHANOL-$d_4$) δ ppm 3.98 (s, 3H) 7.39 (s, 1H) 7.55-7.62 (m, 2H) 7.79-7.86 (m, 2H).

Step B) 4-Methoxy-2-[4-(4,4,5,5-tetramethyl-1,3,2-dioxaborolan-2-yl)phenyl]-2H-1,2,3-triazole Pd(dppf)Cl$_2$ (0.71 g, 0.87 mmol) was added to a mixture of 2-(4-bromophenyl)-4-methoxy-2H-1,2,3-triazole (1.1 g, 2.6 mmol), 4,4,4',4',5,5,5',5'-octamethyl-2,2'-bi-1,3,2-dioxaborolane (1.3 g, 5.2 mmol), potassium acetate (1.3 g, 13.0 mmol), in 2-methyl tetrahydrofuran:water (5:1, 60 mL). The reaction was heated to 80° C. and stirred at this temperature for 16 h. The reaction was allowed to cool to rt, and water (50 mL) was added. The reaction was filtered through celite, which was washed with EtOAc (150 mL). The filtrate was concentrated under reduced pressure, and the resulting crude material was purified by flash chromatography using an eluent of EtOAc in n-heptane (10-60%) to afford the title compound as a light tan solid (1.2 g, 92%). MS (LCMS) m/z 302.3 (M+1). $^1$H NMR (400 MHz, METHANOL-$d_4$) δ ppm 1.33 (s, 12H) 4.01 (s, 3H) 7.40 (s, 1H) 7.78-7.84 (m, 2H) 7.88-7.95 (m, 2H).

Step C) (2R)-4-{5-Fluoro-4-[4-(4-methoxy-2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide The title compound (1.15 mg, 88%) was obtained as tan solid from 4-methoxy-2-[4-(4,4,5,5-tetramethyl-1,3,2-dioxaborolan-2-yl)phenyl]-2H-1,2,3-triazole (0.98 g, 1.4 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (1.2 g, 2.3 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19 Step A. MS (LCMS) m/z 562.0 (M+1).

Step D) (2R)-4-{5-Fluoro-4-[4-(4-methoxy-2H-1,2,3-triazol-2-yl)phenyl]-2-oxopyridin-1(2H)-yl}-N-hydroxy-2-methyl-2-(methylsulfonyl)butanamide The title compound (700 mg, 70%) was obtained as a light tan solid from (2R)-4-{5-fluoro-4-[4-(4-methoxy-2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide (1.15 g, 2.04 mmol) using a procedure analogous to that described for the preparation of (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide, Example 18, Step G. MS (LCMS) m/z 480.2 (M+1). $^1$H NMR (400 MHz, DMSO-$d_6$) δ ppm 1.53 (s, 3H) 2.07-2.18 (m, 1H) 2.39-2.48 (m, 1H) 3.06 (s, 3H) 3.69-3.77 (m, 1H) 3.95 (s, 3H) 3.97-4.08 (m, 1H) 6.54 (d, J=7.62 Hz, 1H) 7.65-7.73 (m, 2H) 7.75 (s, 1H) 7.90-7.98 (m, 2H) 8.03 (d, J=6.64 Hz, 1H) 11.06 (br. s., 1H).

Example 23

(2R)-4-{5-Fluoro-4-[4-(4-methyl-2H-1,2,3-triazol-2-yl)phenyl]-2-oxopyridin-1(2H)-yl}-N-hydroxy-2-methyl-2-(methylsulfonyl)butanamide

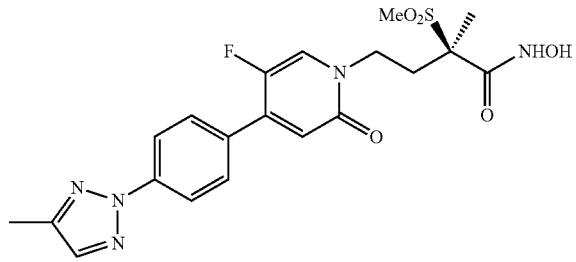

Step A) 4-Methyl-2-(4-(4,4,5,5-tetramethyl-1,3,2-dioxaborolan-2-yl)phenyl)-2H-1,2,3-triazole Pd(dppf)Cl$_2$ (592 mg, 0.718 mmol) was added to a solution of potassium acetate (705 mg, 7.18 mmol), 2-(4-bromophenyl)-4-methyl-2H-1,2,3-triazole (600 mg, 2.52 mmol), and 4,4,4',4',5,5,5',5'-octamethyl-2,2'-bi-1,3,2-dioxaborolane (729 mg, 2.87 mmol) in 1,4-dioxane (20 mL). The reaction was heated to 80° C. and stirred at this temperature for 16 h. The reaction was filtered through celite, and the filter pad was washed with EtOAc (150 mL). The combined filtrates were concentrated under reduced pressure, and the crude material was purified via flash chromatography using EtOAc in n-heptane (10-60%) to afford the title compound as a light tan solid (720 mg, 98%). MS (LCMS) m/z 286.2 (M+1). $^1$H NMR (400 MHz, METHANOL-$d_4$) δ ppm 1.32 (s, 12H) 2.36 (s, 3H) 7.66 (s, 1H) 7.77-7.84 (m, 2H) 7.92-8.00 (m, 2H).

Step B) (2R)-4-{5-Fluoro-4-[4-(4-methyl-2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide The title compound (0.99 g, 98%) was obtained as a tan gum from 4-methyl-2-(4-(4,4,5,5-tetramethyl-1,3,2-dioxaborolan-2-yl)phenyl)-2H-1,2,3-triazole (0.70 g, 2.4 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (0.90 g, 2.0 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 546.5 (M+1).

Step C) (2R)-4-{5-Fluoro-4-[4-(4-methyl-2H-1,2,3-triazol-2-yl)phenyl]-2-oxopyridin-1(2H)-yl}-N-hydroxy-2-methyl-2-(methylsulfonyl)butanamide The title compound (450 mg, 53%) was obtained as a tan solid from (2R)-4-{5-fluoro-4-[4-(4-methyl-2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide (0.99 g, 1.81 mmol) using a procedure analogous to that described for the preparation of (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide, Example 18, Step G. MS (LCMS) m/z 464.2 (M+1). $^1$H NMR (400 MHz, DMSO-$d_6$) δ ppm 1.53 (s, 3H) 2.06-2.20 (m, 1H) 2.33 (br. s, 3H) 2.38-2.49 (m, 1H) 3.06 (s, 3H) 3.68-3.80 (m, 1H) 3.90-4.11 (m, 1H) 6.55 (d, J=7.61 Hz, 1H) 7.65-7.76 (m, 2H) 7.90 (br. s, 1H) 7.96-8.10 (m, 2H) 11.05 (br. s., 1H).

Example 24

(2R)-4-(5-Fluoro-2-oxo-4-quinoxalin-6-ylpyridin-1(2H)-yl)-N-hydroxy-2-methyl-2-(methylsulfonyl)butanamide

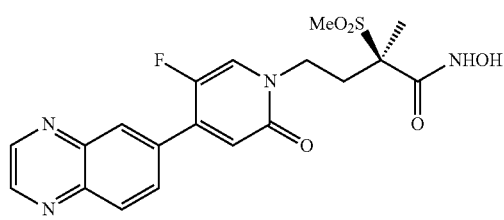

Step A) (2R)-4-(5-Fluoro-2-oxo-4-quinoxalin-6-ylpyridin-1(2H)-yl)-2-methyl-2-(methylsulfonyl)-N-(tetrahydro-2H-pyran-2-yloxy)butanamide The title compound (480 mg, 95%) was obtained as a light brown gum from 6-(4,4,5,5-tetramethyl-1,3,2-dioxaborolan-2-yl)quinoxaline (347 mg, 1.36 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (500 mg, 0.97 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19 Step A. MS (LCMS) m/z 517.1 (M+1).

Step B) (2R)-4-(5-Fluoro-2-oxo-4-quinoxalin-6-ylpyridin-1(2H)-yl)-N-hydroxy-2-methyl-2-(methylsulfonyl)butanamide The title compound (110 mg, 28%) was obtained as a light tan solid from (2R)-4-(5-fluoro-2-oxo-4-quinoxalin-6-ylpyridin-1(2H)-yl)-2-methyl-2-(methylsulfonyl)-N-(tetrahydro-2H-pyran-2-yloxy)butanamide (0.48 g, 0.93 mmol) using a procedure analogous to that described for the preparation of (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide, Example 18, Step G. MS (LCMS) m/z 433.2 (M+1). $^1$H NMR (400 MHz, DMSO-$d_6$) δ ppm 1.54 (s, 3H) 2.09-2.19 (m, 1H) 2.44-2.52 (m, 1H) 3.07 (s, 3H) 3.73-3.84 (m, 1H) 4.04 (m, 1H) 6.71 (d, J=7.61 Hz, 1H) 7.99 (dt, J=8.76, 1.96 Hz, 1H) 8.06-8.10 (m, 1H) 8.17 (d, J=8.78 Hz, 1H) 8.26 (t, J=1.71 Hz, 1H) 8.89-9.05 (m, 2H) 9.20 (br. s., 1H) 11.03 (br. s., 1H).

Example 25

(2R)-4-[5-Fluoro-4-(3-methoxyphenyl)-2-oxopyridin-1(2H)-yl]-N-hydroxy-2-methyl-2-(methylsulfonyl)butanamide

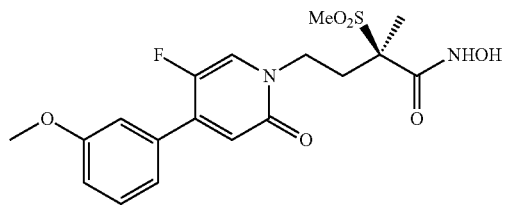

Step A) (2R)-4-[5-Fluoro-4-(3-methoxyphenyl)-2-oxopyridin-1(2H)-yl]-2-methyl-2-(methylsulfonyl)-N-(tetrahydro-2H-pyran-2-yloxy)butanamide The title compound (800 mg, 99%) was obtained as a light tan gum from (3-methoxyphenyl)boronic acid (318 mg, 2.09 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (900 mg, 1.74 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 495.1 (M+1).

Step B) (2R)-4-[5-Fluoro-4-(3-methoxyphenyl)-2-oxopyridin-1(2H)-yl]-N-hydroxy-2-methyl-2-(methylsulfonyl)butanamide The title compound (400 mg, 58%) was obtained as a tan solid from (2R)-4-[5-fluoro-4-(3-methoxyphenyl)-2-oxopyridin-1(2H)-yl]-2-methyl-2-(methylsulfonyl)-N-(tetrahydro-2H-pyran-2-yloxy)butanamide (0.82 g, 1.65 mmol) using a procedure analogous to that described for the preparation of (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide, Example 18, Step G. MS (LCMS) m/z 413.1 (M+1). ¹H NMR (400 MHz, DMSO-d₆) δ ppm 1.52 (s, 3H) 2.05-2.18 (m, 1H) 2.36-2.50 (m, 1H) 3.06 (s, 3H) 3.66-3.78 (m, 4H) 3.95-4.08 (m, 1H) 6.50 (d, J=7.61 Hz, 1H) 6.98-7.11 (m, 3H) 7.32-7.40 (m, 1H) 7.913 (d, J=6.54 Hz, 1H) 9.18 (br. s., 1H) 11.04 (s, 1H).

Example 26

(2R)-4-{5-Fluoro-2-oxo-4-[4-(2H-1,2,3-triazol-2-yl)phenyl]pyridin-1(2H)-yl}-N-hydroxy-2-methyl-2-(methylsulfonyl)butanamide

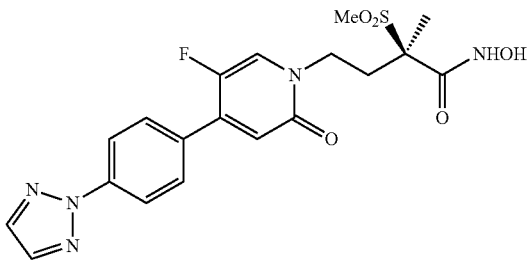

Step A) 2-[4-(4,4,5,5-Tetramethyl-1,3,2-dioxaborolan-2-yl)phenyl]-2H-1,2,3-triazole Pd(dppf)Cl₂ (280 mg, 0.343 mmol) was added to a mixture of 2-(4-bromophenyl)-2H-1,2,3-triazole (255 mg, 1.14 mmol), 4,4,4',4',5,5,5',5'-octamethyl-2,2'-bi-1,3,2-dioxaborolane (350 mg, 1.38 mmol), and potassium acetate (340 mg, 3.46 mmol) in 1,4-dioxane (10 mL). The reaction was heated to 80° C. and stirred at this temperature overnight. The reaction was allowed to cool to rt and was diluted with EtOAc (30 mL) and brine (30 mL). The mixture was filtered through celite, and the organic layer was separated from the filtrate. The aqueous layer was extracted with EtOAc (2×30 mL) and the organics were combined, dried (MgSO₄), filtered and concentrated. The crude material was purified via flash chromatography using an Analogix SF15-12 g column and an eluent of EtOAc in n-heptane (0-10%) to afford the title compound as an orange solid (240.6 mg, 78.0%). MS (LCMS) m/z 272.4 (M+1). ¹H NMR (400 MHz, CHLOROFORM-d) δ ppm 1.37 (s, 12H) 7.83 (s, 2H) 7.94 (d, 2H) 8.10 (d, J=8.59 Hz, 2H).

Step B) Ethyl (2R)-4-{5-fluoro-2-oxo-4-[4-(2H-1,2,3-triazol-2-yl)phenyl]pyridin-1(2H)-yl}-2-methyl-2-(methylsulfonyl)butanoate Pd(dppf)Cl₂ (484 mg, 0.59 mmol) was added to a mixture of ethyl (2R)-4-(5-fluoro-4-iodo-2-oxopyridin-1(2H)-yl)-2-methyl-2-(methylsulfonyl)butanoate, T2, (2.20 g, 4.94 mmol), 2-[4-(4,4,5,5-tetramethyl-1,3,2-dioxaborolan-2-yl)phenyl]-2H-1,2,3-triazole (2.01 g, 7.41 mmol), and potassium phosphate (3.95 g, 14.8 mmol) in 2-methyltetrahydrofuran (200 mL) and deionized water (40 mL). The reaction was heated to 60° C. and was vigorously stirred at this temperature overnight. The reaction was diluted with EtOAc (100 mL) and water (100 mL) and was filtered through a celite pad (~1 inch). The filter pad was washed with EtOAc (100 mL) and the filtrates were combined. The aqueous layer was separated and was extracted with EtOAc (2×100 mL). The combined organics were washed with brine (100 mL), dried (MgSO₄), filtered and concentrated. The crude material was purified via flash chromatography using a Varian SF25-40 g column and an eluent of EtOAc in hexanes (30-100%) to afford the title compound as a yellow solid (1.54 g, 67.4%). MS (LCMS) m/z 463.0 (M+1). ¹H NMR (400 MHz, DMSO-d₆) δ ppm 1.23 (t, 3H) 1.62 (s, 3H) 2.18-2.32 (m, 1H) 2.52-2.66 (m, 1H) 3.16 (s, 3H) 3.92-4.07 (m, 2H) 4.08-4.24 (m, 2H) 6.59 (d, J=7.81 Hz, 1H) 7.72-7.84 (m, 2H) 8.10 (d, J=6.63 Hz, 1H) 8.12-8.17 (m, 2H) 8.18 (s, 2H).

Step C) (2R)-4-{5-Fluoro-2-oxo-4-[4-(2H-1,2,3-triazol-2-yl)phenyl]pyridin-1(2H)-yl}-2-methyl-2-(methylsulfonyl)butanoic acid Potassium hydroxide (1.30 g, 23.2 mmol) was added to a solution of ethyl (2R)-4-{5-fluoro-2-oxo-4-[4-(2H-1,2,3-triazol-2-yl)phenyl]pyridin-1(2H)-yl}-2-methyl-2-(methylsulfonyl)butanoate (1.54 g, 3.33 mmol) in 2-methyltetrahydrofuran:water (2:1 42.5 mL) and the solution was stirred at rt overnight. Methanol (5 mL) was added and the reaction was heated to 60° C. The reaction mixture was stirred at this temperature for 2 h. The reaction was concentrated and triturated in 3 M aq HCl. The solid was collected via filtration and washed with water (20 mL) and hexanes (20 mL). The solid was dried under vacuum to afford the title compound as a white solid (1.39 g, 96.1%). MS (LCMS) m/z 435.0 (M+1). ¹H NMR (400 MHz, DMSO-d₆) δ ppm 1.58 (s, 3H) 2.13-2.30 (m, 0H) 2.41-2.61 (m, 1H) 3.17 (s, 3H) 3.89-4.13 (m, 2H) 6.59 (d, J=7.81 Hz, 1H) 6.56-6.63 (m, 1H) 7.79 (dd, J=8.78, 1.76 Hz, 3H) 8.09 (d, J=6.83 Hz, 1H) 8.12-8.17 (m, 2H) 8.19 (s, 2H).

Step D) (2R)-4-{5-Fluoro-2-oxo-4-[4-(2H-1,2,3-triazol-2-yl)phenyl]pyridin-1(2H)-yl}-2-methyl-2-(methylsulfonyl)-N-(tetrahydro-2H-pyran-2-yloxy)butanamide N-Methylmorpholine (540 μL, 4.9 mmol) was added to a solution of CDMT (750 mg, 4.27 mmol) and (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanoic acid (1.39 g, 3.20 mmol) in 2-methyltetrahydrofuran (30 mL) and the reaction was stirred for 1 h at rt. O-(Tetrahydro-2H-pyran-2-yl)hydroxylamine (670 mg, 5.72 mmol) was added to the reaction and the reaction was stirred overnight at rt. The reaction was quenched with saturated aq NaHCO₃ (100 mL) and the aqueous layer was extracted with EtOAc (3×100 mL). The combined organics were washed with brine (100 mL), dried (MgSO₄), filtered and concentrated. The crude product was purified via flash chromatography using a Varian SF25-40 g column and eluent of EtOAc in hexanes (30-100%) to afford the title compound as a white solid (1.53 g, 89.6%). MS (LCMS) m/z 532.2 (M−1).

Step E) (2R)-4-{5-Fluoro-2-oxo-4-[4-(2H-1,2,3-triazol-2-yl)phenyl]pyridin-1(2H)-yl}-N-hydroxy-2-methyl-2-(methylsulfonyl)butanamide Pyridinium p-toluenesulfonate (360 mg, 0.50 mmol) was added to a solution of (2R)-4-{5-fluoro-2-oxo-4-[4-(2H-1,2,3-triazol-2-yl)phenyl]pyridin-1(2H)-yl}-2-methyl-2-(methylsulfonyl)-N-(tetrahydro-2H-pyran-2-yloxy)butanamide (1.53 g, 2.87 mmol) in ethanol (60 mL). The solution was heated to 70° C. and was stirred at this temperature for 3 h. The reaction was allowed to cool and was stirred at rt for three days. The solid was collected via filtration, washed with ethanol (20 mL) and hexanes (20 mL). The solid was dried under vacuum to afford the title compound as a white solid (1.05 g, 81.5%). MS (LCMS) m/z 450.0 (M+1), $^1$H NMR (400 MHz, DMSO-d$_6$) δ ppm 1.58 (s, 3H) 2.08-2.27 (m, 0H) 2.38-2.59 (m, 1H) 3.12 (s, 3H) 3.72-3.90 (m, 1H) 4.00-4.17 (m, 1H) 6.62 (d, J=7.61 Hz, 1H) 7.70-7.88 (m, 2H) 8.08 (d, J=6.63 Hz, 1H) 8.12-8.18 (m, 2H) 8.19 (s, 2H) 9.25 (d, J=1.95 Hz, 1H) 11.09 (d, J=1.76 Hz, 1H).

Example 27

(2R)-4-[5-Fluoro-4-(2-fluoro-4-methoxyphenyl)-2-oxopyridin-1(2H)-yl]-N-hydroxy-2-methyl-2-(methylsulfonyl)butanamide

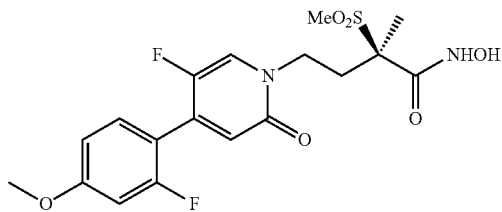

Step A) (2R)-4-[5-Fluoro-4-(2-fluoro-4-methoxyphenyl)-2-oxopyridin-1(2H)-yl]-2-methyl-2-(methylsulfonyl)-N-(tetrahydro-2H-pyran-2-yloxy)butanamide The title compound (1.5 g, 94%) was obtained from (2-fluoro-4-methoxyphenyl)boronic acid (737 mg, 4.34 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (1.6 g, 3.1 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 513.3 (M+1).

Step B) (2R)-4-[5-Fluoro-4-(2-fluoro-4-methoxyphenyl)-2-oxopyridin-1(2H)-yl]-N-hydroxy-2-methyl-2-(methylsulfonyl)butanamide A solution of HCl (4 M in 1,4-dioxane, 4.4 mL, 17.5 mmol) was added to a solution of (2R)-4-[5-fluoro-4-(2-fluoro-4-methoxyphenyl)-2-oxopyridin-1(2H)-yl]-2-methyl-2-(methylsulfonyl)-N-(tetrahydro-2H-pyran-2-yloxy)butanamide (1.5 g, 2.9 mmol) in 1,4-dioxane (20 mL), DCM (20 mL), and water (5 mL) and the reaction was stirred for 20 min at rt. The reaction was concentrated under reduced pressure, isopropyl alcohol (10 mL) was added to the residue and the mixture was concentrated. Isopropyl alcohol (30 mL) was added to the residue and the solution was stirred overnight at it to afford a precipitate. The precipitate was collected via filtration, washed with isopropyl alcohol, and dried under vacuum to afford the title compound as a light brown solid (725 mg, 58%) MS (LCMS) m/z 431.0 (M+1). $^1$H NMR (400 MHz, DMSO-d$_6$) δ ppm 1.57 (s, 3H) 2.07-2.25 (m, 1H) 2.42-2.48 (m, 1H) 3.11 (s, 3H) 3.71-3.81 (m, 1H) 3.83 (s, 3H) 4.00-4.11 (m, 1H) 6.44 (d, J=7.02 Hz, 1H) 6.92 (dd, J=8.59, 2.54 Hz, 1H) 7.00 (dd, J=12.39, 2.44 Hz, 1H) 7.42 (t, J=8.49 Hz, 1H) 8.03 (d, J=5.85 Hz, 1H) 9.25 (br. s., 1H) 11.10 (s, 1H).

Example 28

(2R)-4-[5-Fluoro-4-(4-methoxyphenyl)-2-oxopyridin-1(2H)-yl]-N-hydroxy-2-methyl-2-(methylsulfonyl)butanamide

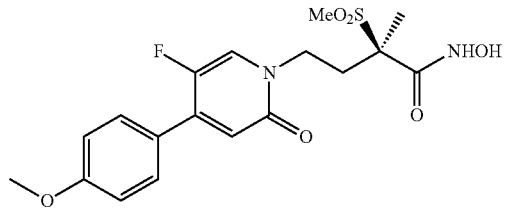

Step A) (2R)-4-[5-Fluoro-4-(4-methoxyphenyl)-2-oxopyridin-1(2H)-yl]-2-methyl-2-(methylsulfonyl)-N-(tetrahydro-2H-pyran-2-yloxy)butanamide The title compound (1.90 g, 98.8%) was obtained as a yellow solid from (4-methoxyphenyl)boronic acid (902 mg, 5.94 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (2.0 g, 3.87 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 495.4 (M−1).

Step B) (2R)-4-[5-Fluoro-4-(4-methoxyphenyl)-2-oxopyridin-1(2H)-yl]-N-hydroxy-2-methyl-2-(methylsulfonyl)butanamide The title compound (651 mg, 41.3%) was obtained as a white solid from (2R)-4-[5-fluoro-4-(4-methoxyphenyl)-2-oxopyridin-1(2H)-yl]-2-methyl-2-(methylsulfonyl)-N-(tetrahydro-2H-pyran-2-yloxy)butanamide (1.90 g, 3.83 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide Example 26, Step E. MS (LCMS) m/z 413.0 (M+1). $^1$H NMR (400 MHz, DMSO-d$_6$) δ ppm 1.57 (s, 3H) 2.08-2.23 (m, 1H) 2.41-2.48 (m, 1H) 3.11 (s, 3H) 3.72-3.80 (m, 1H) 3.81 (s, 3H) 3.97-4.13 (m, 1H) 6.49 (d, J=7.81 Hz, 1H) 6.95-7.15 (m, 2H) 7.46-7.67 (m, 2H) 7.99 (d, J=6.63 Hz, 1H) 9.24 (s, 1H) 11.11 (s, 1H).

Example 29

(2R)-4-[5-Fluoro-4-(4-methylphenyl)-2-oxopyridin-1(2H)-yl]-N-hydroxy-2-methyl-2-(methylsulfonyl)butanamide

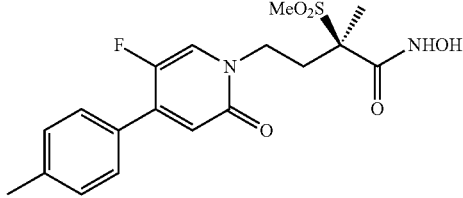

Step A) Ethyl (2R)-4-[5-fluoro-4-(4-methylphenyl)-2-oxopyridin-1(2H)-yl]-2-methyl-2-(methylsulfonyl)butanoate The title compound (484 mg) was obtained as a brown gum from (4-methylphenyl)boronic acid (229 mg, 1.68 mmol) and ethyl (2R)-4-(5-fluoro-4-iodo-2-oxopyridin-1(2H)-yl)-2-methyl-2-(methylsulfonyl)butanoate, T2, (500 mg, 1.12 mmol) using a procedure analogous to that described for the preparation of ethyl (2R)-4-{5-fluoro-2-oxo-4-[4-(2H-1,2,3-triazol-2-yl)phenyl]pyridin-1(2H)-yl}-2-methyl-2-(methylsulfonyl)butanoate, Example 27, Step B. MS (LCMS) m/z 410.1 (M+1).

Step B) (2R)-4-[5-Fluoro-4-(4-methylphenyl)-2-oxopyridin-1(2H)-yl]-2-methyl-2-(methylsulfonyl)butanoic acid The title compound (294 mg, 65.2%) was obtained as a white solid from ethyl (2R)-4-[5-fluoro-4-(4-methylphenyl)-2-oxopyridin-1(2H)-yl]-2-methyl-2-(methylsulfonyl)butanoate (484 mg, 1.18 mmol) using a procedure analogous to that described for the preparation of (2R)-4-{5-fluoro-2-oxo-4-[4-(2H-1,2,3-triazol-2-yl)phenyl]pyridin-1(2H)-yl}-2-methyl-2-(methylsulfonyl)butanoic acid, Example 26, Step C. MS (LCMS) m/z 382.0 (M+1). $^1$H NMR (400 MHz, DMSO-$d_6$) δ ppm 1.57 (s, 3H) 2.14-2.25 (m, 0H) 2.36 (s, 3H) 2.43-2.54 (m, 1H) 3.17 (s, 3H) 3.89-4.07 (m, 2H) 6.46 (d, J=7.81 Hz, 1H) 7.31 (d, J=8.00 Hz, 2H) 7.42-7.52 (m, 2H) 8.03 (d, J=6.83 Hz, 1H).

Step C) (2R)-4-[5-Fluoro-4-(4-methylphenyl)-2-oxopyridin-1(2H)-yl]-2-methyl-2-(methylsulfonyl)-N-(tetrahydro-2H-pyran-2-yloxy)butanamide The title compound (331 mg, 89.3%) was obtained as a white solid from (2R)-4-[5-fluoro-4-(4-methylphenyl)-2-oxopyridin-1(2H)-yl]-2-methyl-2-(methylsulfonyl)butanoic acid (294 mg, 0.77 mmol) using a procedure analogous to that described for the preparation of 2R)-4-{5-fluoro-2-oxo-4-[4-(2H-1,2,3-triazol-2-yl)phenyl]pyridin-1(2H)-yl}-2-methyl-2-(methylsulfonyl)-N-(tetrahydro-2H-pyran-2-yloxy)butanamide, Example 26, Step D. MS (LCMS) m/z 479.3 (M−1).

Step D) (2R)-4-[5-Fluoro-4-(4-methylphenyl)-2-oxopyridin-1(2H)-yl]-N-hydroxy-2-methyl-2-(methylsulfonyl)butanamide The title compound (96 mg, 34%) was obtained as a white solid from (2R)-4-[5-fluoro-4-(4-methylphenyl)-2-oxopyridin-1(2H)-yl]-2-methyl-2-(methylsulfonyl)-N-(tetrahydro-2H-pyran-2-yloxy)butanamide (331 mg, 0.69 mmol) using a procedure analogous to that described for the preparation of 2R)-4-{5-fluoro-2-oxo-4-[4-(2H-1,2,3-triazol-2-yl)phenyl]pyridin-1(2H)-yl}-2-methyl-2-(methylsulfonyl)butanamide, Example 26, Step E. MS (LCMS) m/z 397.0 (M+1). $^1$H NMR (400 MHz, DMSO-$d_6$) δ ppm 1.58 (s, 3H) 2.10-2.25 (m, 1H) 2.37 (s, 3H) 2.42-2.49 (m, 1H) 3.12 (s, 3H) 3.71-3.84 (m, 1H) 4.00-4.12 (m, 1H) 6.51 (d, J=7.81 Hz, 1H) 7.32 (d, J=7.81 Hz, 2H) 7.48 (dd, J=8.20, 1.76 Hz, 2H) 8.02 (d, J=6.83 Hz, 1H) 9.24 (d, J=1.76 Hz, 1H) 11.11 (d, J=1.95 Hz, 1H).

Example 30

(2R)-4-{5-Fluoro-2-oxo-4-[4-(trifluoromethoxy)phenyl]pyridin-1(2H)-yl}-N-hydroxy-2-methyl-2-(methylsulfonyl)butanamide

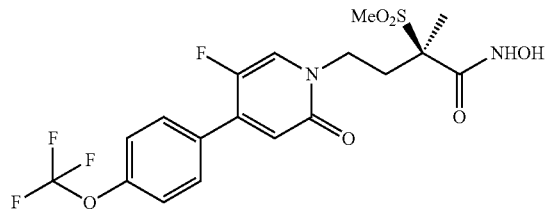

Step A) (2R)-4-{5-Fluoro-2-oxo-4-[4-(trifluoromethoxy)phenyl]pyridin-1(2H)-yl}-2-methyl-2-(methylsulfonyl)-N-(tetrahydro-2H-pyran-2-yloxy)butanamide The title compound (69.7 mg, 49.1%) was obtained as a yellow-white solid from [4-(trifluoromethoxy)phenyl]boronic acid (82.3 mg, 0.47 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (133 mg, 0.26 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 20, Step A. MS (LCMS) m/z 551.1 (M−1).

Step B) (2R)-4-{5-Fluoro-2-oxo-4-[4-(trifluoromethoxy)phenyl]pyridin-1(2H)-yl}-N-hydroxy-2-methyl-2-(methylsulfonyl)butanamide The title compound (12.2 mg, 20.9%) was obtained as a white solid from (2R)-4-{5-fluoro-2-oxo-4-[4-(trifluoromethoxy)phenyl]pyridin-1(2H)-yl}-2-methyl-2-(methylsulfonyl)-N-(tetrahydro-2H-pyran-2-yloxy)butanamide (68.9 mg, 0.13 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 467.0 (M+1). $^1$H NMR (400 MHz, DMSO-$d_6$) δ ppm 1.57 (s, 3H) 2.07-2.25 (m, 0H) 2.39-2.55 (m, 1H) 3.11 (s, 3H) 3.72-3.86 (m, 1H) 3.97-4.13 (m, 1H) 6.58 (d, 1H) 7.50 (d, J=8.00 Hz, 2H) 7.65-7.77 (m, 2H) 8.06 (d, J=6.44 Hz, 1H) 9.23 (d, J=1.17 Hz, 1H) 11.08 (s, 1H).

Example 31

(2R)-4-[5-Fluoro-4-(4-fluorophenyl)-2-oxopyridin-1(2H)-yl]-N-hydroxy-2-methyl-2-(methylsulfonyl)butanamide

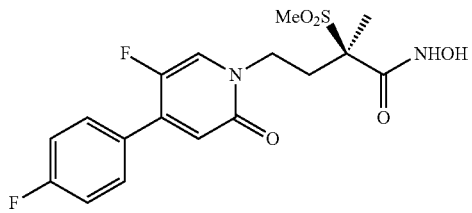

Step A) (2R)-4-[5-Fluoro-4-(4-fluorophenyl)-2-oxopyridin-1(2H)-yl]-2-methyl-2-(methylsulfonyl)-N-(tetrahydro-2H-pyran-2-yloxy)butanamide The title compound (67 mg, 54%) was obtained as a white solid from (4-fluorophenyl)boronic acid (66.2 mg, 0.47 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (133 mg, 0.26 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 483.1 (M−1).

Step B) (2R)-4-[5-Fluoro-4-(4-fluorophenyl)-2-oxopyridin-1(2H)-yl]-N-hydroxy-2-methyl-2-(methylsulfonyl)butanamide The title compound (7.9 mg, 14%) was obtained as a white solid from (2R)-4-[5-fluoro-4-(4-fluorophenyl)-2-oxopyridin-1(2H)-yl]-2-methyl-2-(methylsulfonyl)-N-(tetrahydro-2H-pyran-2-yloxy)butanamide (67 mg, 0.14 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 401.0 (M+1). $^1$H NMR (400 MHz, DMSO-d$_6$) δ ppm 1.58 (s, 3H) 2.10-2.24 (m, 1H) 2.42-2.50 (m, 1H) 3.12 (s, 3H) 3.71-3.88 (m, 1H) 3.99-4.14 (m, 1H) 6.55 (d, J=7.61 Hz, 1H) 7.25-7.45 (m, 2H) 7.58-7.72 (m, 2H) 8.05 (d, J=6.83 Hz, 1H) 9.24 (s, 1H) 11.10 (s, 1H).

Example 32

(2R)-4-{5-Fluoro-4-[4-(6-methoxypyridin-3-yl)phenyl]-2-oxopyridin-1(2H)-yl}-N-hydroxy-2-methyl-2-(methylsulfonyl)butanamide

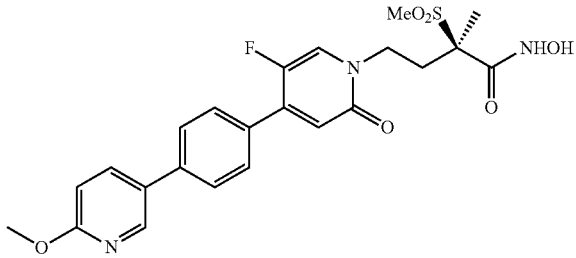

Step A) 2-Methoxy-5-[4-(4,4,5,5-tetramethyl-1,3,2-dioxaborolan-2-yl)phenyl]pyridine The title compound (1.40 g) was obtained as a white solid from 5-(4-bromophenyl)-2-methoxypyridine (1.0 g, 3.8 mmol) using a procedure analogous to that described for the preparation of 2-[4-(4,4,5,5-tetramethyl-1,3,2-dioxaborolan-2-yl)phenyl]-2H-1,2,3-triazole, Example 26, Step A. MS (LCMS) m/z 312.1 (M+1).

Step B) (2R)-4-{5-Fluoro-4-[4-(6-methoxypyridin-3-yl)phenyl]-2-oxopyridin-1(2H)-yl}-2-methyl-2-(methylsulfonyl)-N-(tetrahydro-2H-pyran-2-yloxy)butanamide The title compound (273 mg, 61.4%) was obtained as a yellow solid from 2-methoxy-5-[4-(4,4,5,5-tetramethyl-1,3,2-dioxaborolan-2-yl)phenyl]pyridine (362 mg, 1.16 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (400 mg, 0.78 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 574.0 (M+1).

Step C) (2R)-4-{5-Fluoro-4-[4-(6-methoxypyridin-3-yl)phenyl]-2-oxopyridin-1(2H)-yl}-N-hydroxy-2-methyl-2-(methylsulfonyl)butanamide The title compound (156 mg, 67%) was obtained as a white solid from (2R)-4-{5-fluoro-4-[4-(6-methoxypyridin-3-yl)phenyl]-2-oxopyridin-1(2H)-yl}-2-methyl-2-(methylsulfonyl) N-(tetrahydro-2H-pyran-2-yloxy)butanamide (273 mg, 0.48 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 490.0 (M+1). $^1$H NMR (400 MHz, DMSO-d$_6$) δ ppm 1.58 (s, 3H) 2.09-2.27 (m, 0H) 2.43-2.57 (m, 1H) 3.12 (s, 3H) 3.73-3.86 (m, 1H) 3.91 (s, 3H) 4.00-4.14 (m, 1H) 6.59 (d, J=7.61 Hz, 1H) 6.94 (d, J=8.59 Hz, 1H) 7.60-7.73 (m, 2H) 7.75-7.86 (m, 2H) 7.98-8.19 (m, 2H) 8.57 (d, J=2.54 Hz, 1H) 9.25 (br. S., 1H) 11.10 (s, 1H).

Example 33

(2R)-4-{4-[4-(Difluoromethoxy)phenyl]-5-fluoro-2-oxopyridin-1(2H)-yl}-N-hydroxy-2-methyl-2-(methylsulfonyl)butanamide

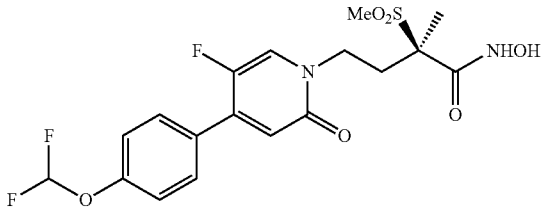

Step A) (2R)-4-{4-[4-(Difluoromethoxy)phenyl]-5-fluoro-2-oxopyridin-1(2H)-yl}-2-methyl-2-(methylsulfonyl)-N-(tetrahydro-2H-pyran-2-yloxy)butanamide The title compound (69.7 mg, 49.1%) was obtained as a yellow solid from 2-[4-(difluoromethoxy)phenyl]-4,4,5,5- tetramethyl-1,3,2-dioxaborolane (82.3 mg, 0.47 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (133 mg, 0.26 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 531.2 (M−1).

Step B) (2R)-4-{4-[4-(Difluoromethoxy)phenyl]-5-fluoro-2-oxopyridin-1(2H)-yl}-N-hydroxy-2-methyl-2-(methylsulfonyl)butanamide The title compound (9.0 mg, 18%) was obtained as a white solid from (2R)-4-{4-[4-(difluoromethoxy)phenyl]-5-fluoro-2-oxopyridin-1(2H)-yl}-2-methyl-2-(methylsulfonyl)-N-(tetrahydro-2H-pyran-2-yloxy)butanamide (58.0 mg, 0.11 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 449.0 (M+1). $^1$H NMR (400 MHz, DMSO-$d_6$) δ ppm 1.58 (s, 3H) 2.09-2.26 (m, 1H) 2.40-2.48 (m, 1H) 3.12 (s, 3H) 3.71-3.86 (m, 1H) 3.98-4.14 (m, 1H) 6.55 (d, 1H) 7.13-7.57 (m, 3H) 7.61-7.80 (m, 2H) 8.05 (d, J=6.63 Hz, 1H) 9.24 (d, J=1.76 Hz, 1H) 11.10 (d, J=1.56 Hz, 1H).

Example 34

(2R)-4-[5-Fluoro-4-(4-methoxy-3-methylphenyl)-2-oxopyridin-1(2H)-yl]-N-hydroxy-2-methyl-2-(methylsulfonyl)butanamide

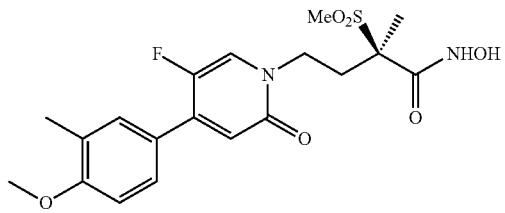

Step A) (2R)-4-[5-Fluoro-4-(4-methoxy-3-methylphenyl)-2-oxopyridin-1(2H)-yl]-2-methyl-2-(methylsulfonyl)-N-(tetrahydro-2H-pyran-2-yloxy)butanamide The title compound (332.1 mg, 65.2%) was obtained as a yellow solid from (4-methoxy-3-methylphenyl)boronic acid (280 mg, 1.69 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (500 mg, 0.97 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 511.0 (M+1).

Step B) (2R)-4-[5-Fluoro-4-(4-methoxy-3-methylphenyl)-2-oxopyridin-1(2H)-yl]-N-hydroxy-2-methyl-2-(methylsulfonyl)butanamide The title compound (46 mg, 17%) was obtained as a white solid from (2R)-4-[5-fluoro-4-(4-methoxy-3-methylphenyl)-2-oxopyridin-1(2H)-yl]-2-methyl-2-(methylsulfonyl)-N-(tetrahydro-2H-pyran-2-yloxy)butanamide (322 mg, 0.63 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 427.0 (M+1). $^1$H NMR (400 MHz, DMSO-$d_6$) δ ppm 1.57 (s, 3H) 2.08-2.25 (m, 4H) 2.38-2.49 (m, 1H) 3.11 (s, 3H) 3.70-3.81 (m, 1H) 3.84 (s, 3H) 3.97-4.11 (m, 1H) 6.48 (d, 1H) 7.05 (d, J=8.39 Hz, 1H) 7.28-7.50 (m, 2H) 7.98 (d, J=6.63 Hz, 1H) 9.24 (br. S., 1H) 11.11 (s, 1H).

Example 35

(2R)-4-{4-[4-(difluoromethoxy)-3-fluorophenyl]-5-fluoro-2-oxopyridin-1(2H)-yl}-N-hydroxy-2-methyl-2-(methylsulfonyl)butanamide

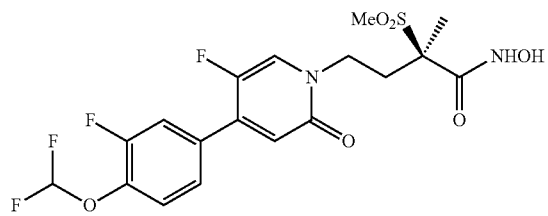

Step A) (2R)-4-{4-[4-(Difluoromethoxy)-3-fluorophenyl]-5-fluoro-2-oxopyridin-1(2H)-yl}-2-methyl-2-(methylsulfonyl)-N-(tetrahydro-2H-pyran-2-yloxy)butanamide The title compound (227 mg, 42.6%) was obtained as a yellow-white solid from 2-[4-(difluoromethoxy)-3-fluorophenyl]-4,4,5,5-tetramethyl-1,3,2-dioxaborolane (630 mg, 2.19 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (500 mg, 0.97 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 549.3 (M−1).

Step B) (2R)-4-{4-[4-(Difluoromethoxy)-3-fluorophenyl]-5-fluoro-2-oxopyridin-1(2H)-yl}-N-hydroxy-2-methyl-2-(methylsulfonyl)butanamide The title compound (92 mg, 62%) was obtained as a white solid from (2R)-4-{4-[4-(difluoromethoxy)-3-fluorophenyl]-5-fluoro-2-oxopyridin-1(2H)-yl}-2-methyl-2-(methylsulfonyl)-N-(tetrahydro-2H-pyran-2-yloxy)butanamide (227 mg, 0.41 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 467.0 (M+1). $^1$H NMR (400 MHz, DMSO-$d_6$) δ ppm 1.57 (s, 3H) 2.08-2.22 (m, 1H) 2.40-2.48 (m, 1H) 3.11 (s, 3H) 3.70-3.86 (m, 1H) 3.97-4.14

(m, 1H) 6.61 (d, 1H) 7.09-7.38 (m, 1H) 7.42-7.57 (m, 2H) 7.69 (d, J=11.12 Hz, 1H) 8.07 (d, J=6.63 Hz, 1H) 9:24 (br. S., 1H) 11.08 (s, 1H).

Example 36

(2R)-4-{5-Fluoro-4-[3-fluoro-4-(2H-1,2,3-triazol-2-yl)phenyl]-2-oxopyridin-1(2H)-yl}-N-hydroxy-2-methyl-2-(methylsulfonyl)butanamide

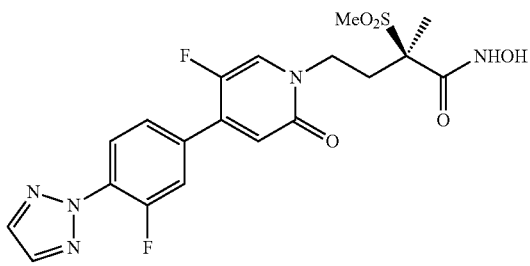

Step A) (1E,2E)-Ethanedial bis[(4-bromo-2-fluorophenyl)hydrazone]

(4-Bromo-3-fluorophenyl)hydrazine-hydrochloride (5.0 g, 24.3 mmol) was added to a mixture of EtOAc (60 mL) and 3 N aq NaOH (60 mL) and the mixture was stirred until all solids went into solution. The organic layer was separated and the aqueous layer was extracted with EtOAc (2×60 mL). The combined organics were washed with brine (60 mL), dried (MgSO$_4$), filtered and concentrated to afford an orange solid (3.27 g, 15.9 mmol). The solid was suspended in toluene (25 mL). Oxalaldehyde (40% aq solution, 912 uL, 7.92 mmol) was added dropwise to the solution and the reaction was stirred overnight at rt. The precipitate was collected via filtration and washed with toluene (25 mL) and hexanes (50 mL). The solid was dried under vacuum to afford the title compound as a yellow solid (2.61 g, 78.1%). MS (LCMS) m/z 431.1 (M−1).

Step B) 2-(4-Bromo-2-fluorophenyl)-2H-1,2,3-triazole

Copper (II) trifluoromethanesulfonate (218 mg, 0.60 mmol) was added to a slurry of (1E,2E)-ethanedial bis[(4-bromo-2-fluorophenyl)hydrazone] (2.61 g, 6.04 mmol) in toluene (25 mL). The reaction was heated to reflux and stirred at this temperature overnight. The reaction was allowed to cool and was filtered through celite, and the filter pad was washed with EtOAc (100 mL). The combined filtrates were washed with 1 N aq HCl (3×100 mL), water (100 mL), and brine (100 mL) and then dried (MgSO$_4$), filtered and concentrated. The crude product was purified via flash chromatography using a Varian SF25-40 g column and an eluent of EtOAc in hexanes (0-50%) to afford the title compound as a yellow solid (1.08 g, 73.9%). $^1$H NMR (400 MHz, CHLOROFORM-d) δ ppm 7.44 (ddd, 1H) 7.47-7.54 (m, 1H) 7.76 (t, 1H) 7.90 (s, 2H).

Step C) 2-[2-Fluoro-4-(4,4,5,5-tetramethyl-1,3,2-dioxaborolan-2-yl)phenyl]-2H-1,2,3-triazole The title compound (1.54 g) was obtained as a yellow solid from 2-(4-bromo-2-fluorophenyl)-2H-1,2,3-triazole (1.08 g, 4.82 mmol) using a procedure analogous to that described for the preparation of 2-[4-(4,4,5,5-tetramethyl-1,3,2-dioxaborolan-2-yl)phenyl]-2H-1,2,3-triazole, Example 26, Step A. MS (LCMS) m/z 290.1 (M+1).

Step D) (2R)-4-{5-Fluoro-4-[3-fluoro-4-(2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide The title compound (275 mg, 51.5%) was obtained as a yellow solid from 2-[2-fluoro-4-(4,4,5,5-tetramethyl-1,3,2-dioxaborolan-2-yl)phenyl]-2H-1,2,3-triazole (420 mg, 1.45 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (500 mg, 0.97 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 550.3 (M−1).

Step E) (2R)-4-{5-Fluoro-4-[3-fluoro-4-(2H-1,2,3-triazol-2-yl)phenyl]-2-oxopyridin-1(2H)-yl}-N-hydroxy-2-methyl-2-(methylsulfonyl)butanamide The title compound (133 mg, 57%) was obtained as a white solid from (2R)-4-{5-Fluoro-4-[3-fluoro-4-(2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide (275 mg, 0.50 mmol) through a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 468.0 (M+1). $^1$H NMR (400 MHz, DMSO-d$_6$) δ ppm 1.58 (s, 3H) 2.10-2.25 (m, 0H) 2.43-2.56 (m, 1H) 3.12 (s, 3H) 3.74-3.89 (m, 1H) 4.00-4.15 (m, 1H) 6.70 (d, J=7.61 Hz, 1H) 7.60-7.66 (m, 1H) 7.75-7.86 (m, 1H) 8.00 (t, J=8.20 Hz, 1H) 8.10 (d, J=6.63 Hz, 1H) 8.23 (s, 2H) 9.24 (br. S., 1H) 11.08 (s, 1H).

Example 37

(2R)-4-{5-Fluoro-4-[3-methyl-4-(2H-1,2,3-triazol-2-yl)phenyl]-2-oxopyridin-1(2H)-yl}-N-hydroxy-2-methyl-2-(methylsulfonyl)butanamide

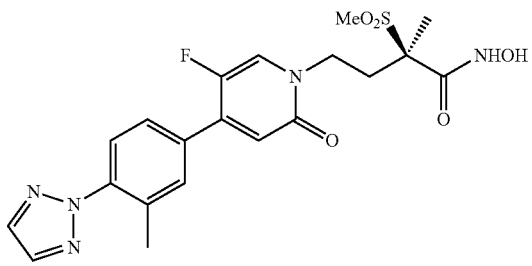

Step A) (1E,2E)-Ethanedial bis[(4-bromo-2-methylphenyl)hydrazone]

The title compound (1.45 g, 87.9%) was obtained as a yellow solid from (4-bromo-2-methylphenyl)hydrazine-hydrochloride (2.00 g, 8.42 mmol) and oxalaldehyde (40% aq solution, 450 uL, 3.9 mmol) through a procedure analogous to that described for the preparation of (1E,2E)-ethanedial bis[(4-bromo-2-fluorophenyl)hydrazone], Example 36, Step A. MS (LCMS) m/z 425.0 (M+1). $^1$H NMR (400 MHz, DMSO-$d_6$) δ ppm 2.20 (s, 6H) 7.09-7.33 (m, 6H) 7.95 (s, 2H) 9.73 (s, 2H).

Step B) 2-(4-Bromo-2-methylphenyl)-2H-1,2,3-triazole

The title compound (608 g, 59.0%) was obtained as a yellow solid from (1E,2E)-ethanedial bis[(4-bromo-2-methylphenyl)hydrazone (1.45 g, 3.42 mmol) through a procedure analogous to that described for the preparation of 2-(4-bromo-2-fluorophenyl)-2H-1,2,3-triazole, Example 36, Step B. $^1$H NMR (400 MHz, CHLOROFORM-d) δ ppm 2.38 (s, 3H) 7.44-7.48 (m, 2H) 7.50-7.53 (m, 1H) 7.85 (s, 2H).

Step C) 2-[2-Methyl-4-(4,4,5,5-tetramethyl-1,3,2-dioxaborolan-2-yl)phenyl]-2H-1,2,3-triazole The title compound (688 mg, 82.3%) was obtained as an orange solid from 2-(4-bromo-2-methylphenyl)-2H-1,2,3-triazole (698 mg, 2.93 mmol) through a procedure analogous to that described for the preparation of 2-[4-(4,4,5,5-tetramethyl-1,3,2-dioxaborolan-2-yl)phenyl]-2H-1,2,3-triazole, Example 26, Step A. $^1$H NMR (400 MHz, CHLOROFORM-d) δ ppm 1.36-1.41 (m, 12H) 2.42 (s, 3H) 7.61 (d, J=8.00 Hz, 1H) 7.76 (d, J=7.81 Hz, 1H) 7.80 (s, 1H) 7.85 (s, 2H).

Step D) (2R)-4-{5-Fluoro-4-[3-methyl-4-(2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide The title compound (630 mg, 71.5%) was obtained as a yellow solid from 2-[2-methyl-4-(4,4,5,5-tetramethyl-1,3,2-dioxaborolan-2-yl)phenyl]-2H-1,2,3-triazole (688 mg, 2.41 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (830 mg, 1.61 mmol) through a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 546.2 (M−1).

Step E) (2R)-4-{5-Fluoro-4-[3-methyl-4-(2H-1,2,3-triazol-2-yl)phenyl]-2-oxopyridin-1(2H)-yl}-N-hydroxy-2-methyl-2-(methylsulfonyl)butanamide The title compound (253 mg, 47.5%) was obtained as a white solid from (2R)-4-{5-fluoro-4-[3-methyl-4-(2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide (630 mg, 1.15 mmol) through a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 464.1 (M+1). $^1$H NMR (400 MHz, DMSO-$d_6$) δ ppm 1.58 (s, 3H) 2.11-2.26 (m, 1H) 2.39 (s, 3H) 3.11 (s, 3H) 3.74-3.87 (m, 1H) 3.99-4.16 (m, 1H) 6.64 (d, J=7.61 Hz, 1H) 7.60 (d, J=8.00 Hz, 1H) 7.63-7.77 (m, 2H) 8.08 (d, J=6.63 Hz, 1H) 8.16 (s, 2H) 9.24 (br. s., 1H) 11.09 (s, 1H).

Example 38

(2R)-4-(3,5-Difluoro-2-oxo-4-phenylpyridin-1(2H)-yl)-N-hydroxy-2-methyl-2-(methylsulfonyl)butanamide

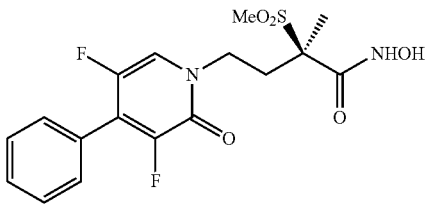

Step A) 3,5-Difluoro-4-iodopyridin-2(1H)-one 2,3,5-Trifluoro-4-iodopyridine (6.03 g, 23.3 mmol) was suspended in 6 M aq HCl (250 mL). The mixture was heated to reflux and was stirred at this temperature overnight. The reaction was concentrated to dryness to afford the title compound as an orange solid (4.14 g, 69.2%). MS (LCMS) m/z 257.9 (M+1).

Step B) Ethyl (2R)-4-(3,5-difluoro-4-iodo-2-oxopyridin-1(2H)-yl)-2-methyl-2-(methylsulfonyl)butanoate Cesium carbonate (1.90 g, 5.84 mmol) was added to a solution of the 3,5-difluoro-4-iodopyridin-2(1H)-one (1.0 g, 3.9 mmol) and ethyl (2R)-4-bromo-2-methyl-2-(methylsulfonyl)butanoate, T1, (1.45 g, 5.06 mmol) in tetrahydrofuran:t-butanol (1:1, 50 mL). The resulting suspension was heated to reflux and was stirred at this temperature for 72 h. The reaction was filtered through celite, and the filter pad was washed with EtOAc (3×50 mL). The combined filtrates were concentrated and the crude product was purified via flash chromatography on an Analogix SF15-24 g column using an eluent of EtOAc in hexanes (0-50%) to afford the title compound as a yellow solid (575.6 mg, 32%). MS (LCMS) m/z 463.9 (M+1). $^1$H NMR (400 MHz, DMSO-$d_6$) δ ppm 1.23 (s, 3H) 1.58 (s, 3H) 2.20 (dt, J=13.90, 7.00 Hz, 1H) 2.52-2.62 (m, 1H) 3.14 (s, 3H) 4.00 (t, J=7.61 Hz, 2H) 4.05-4.22 (m, 2H) 7.94 (dd, J=4.20, 2.05 Hz, 1H).

Step C) Ethyl (2R)-4-(3,5-difluoro-2-oxo-4-phenylpyridin-1(2H)-yl)-2-methyl-2-(methylsulfonyl)butanoate The title compound (110 mg, 63%) was obtained as a white solid from phenylboronic acid (98.8 mg, 0.81 mmol) and ethyl (2R)-4-(3,5-difluoro-4-iodo-2-oxopyridin-1(2H)-yl)-2-methyl-2-(methylsulfonyl)butanoate (250 mg, 0.54 mmol) using a procedure analogous to that described for the preparation of ethyl (2R)-4-{5-fluoro-2-oxo-4-[4-(2H-1,2,3-triazol-2-yl)phenyl]pyridin-1(2H)-yl}-2-methyl-2-(methylsulfonyl)butanoate, Example 26, Step B. MS (LCMS) m/z 414.0 (M+1). $^1$H NMR (400 MHz, CHLOROFORM-d) δ ppm 1.33-1.46 (m, 3H) 1.78 (s, 3H) 2.44-2.65 (m, 2H) 3.14 (s, 3H) 3.98-4.16 (m, 1H) 4.25-4.43 (m, 3H) 7.23 (dd, J=5.07, 2.15 Hz, 1H) 7.40-7.61 (m, 5H).

Step D) (2R)-4-(3,5-Difluoro-2-oxo-4-phenylpyridin-1(2H)-yl)-2-methyl-2-(methylsulfonyl)butanoic acid The title compound (91 mg, 79.2%) was obtained as a white solid from ethyl (2R)-4-(3,5-difluoro-2-oxo-4-phenylpyridin-1(2H)-yl)-2-methyl-2-(methylsulfonyl)butanoate (110 mg, 0.27 mmol) using a procedure analogous to that described for the preparation of (2R)-4-{5-fluoro-2-oxo-4-[4-(2H-1,2,3-triazol-2-yl)phenyl]pyridin-1(2H)-yl}-2-methyl-2-(methylsulfonyl)butanoic acid, Example 26, Step C. MS (LCMS) m/z 386.0 (M+1).

Step E) (2R)-4-(3,5-Difluoro-2-oxo-4-phenylpyridin-1(2H)-yl)-2-methyl-2-(methylsulfonyl)-N-(tetrahydro-2H-pyran-2-yloxy)butanamide The title compound (75.9 mg, 66%) was obtained as an off-white solid from (2R)-4-(3,5-difluoro-2-oxo-4-phenylpyridin-1(2H)-yl)-2-methyl-2-(methylsulfonyl)butanoic acid (91 mg, 0.36 mmol) using a procedure analogous to that described for the preparation of 2R)-4-{5-fluoro-2-oxo-4-[4-(2H-1,2,3-triazol-2-yl)phenyl]pyridin-1(2H)-yl}-2-methyl-2-(methylsulfonyl)-N-(tetrahydro-2H-pyran-2-yloxy)butanamide, Example 26, Step D. MS (LCMS) m/z 483.2 (M+1).

Step F) (2R)-4-(3,5-Difluoro-2-oxo-4-phenylpyridin-1(2H)-yl)-N-hydroxy-2-methyl-2-(methylsulfonyl)butanamide The title compound (13.9 mg, 22%) was obtained as a white solid from (2R)-4-(3,5-difluoro-2-oxo-4-phenylpyridin-1(2H)-yl)-2-methyl-2-(methylsulfonyl)-N-(tetrahydro-2H-pyran-2-yloxy)butanamide (75 mg, 0.16 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide Example 26, Step E. MS (LCMS) m/z 401.0 (M+1). $^1$H NMR (400 MHz, DMSO-d$_6$) δ ppm 1.59 (s, 3H) 2.11-2.22 (m, 1H) 2.52-2.62 (m, 1H) 3.10 (s, 3H) 3.79-3.99 (m, 1H) 4.03-4.20 (m, 1H) 7.40-7.64 (m, 5H) 7.98 (dd, J=5.85, 1.95 Hz, 1H) 9.24 (br. S., 1H) 11.01 (s, 1H).

Example 39

(2R)-4-(5-Fluoro-3-methoxy-2-oxo-4-phenylpyridin-1(2H)-yl)-N-hydroxy-2-methyl-2-(methylsulfonyl)butanamide

Step A) (2R)-4-(5-Fluoro-3-methoxy-2-oxo-4-phenylpyridin-1(2H)-yl)-2-methyl-2-(methylsulfonyl)butanoic acid Potassium hydroxide (100 mg, 1.78 mmol) was added to a solution of ethyl (2R)-4-(3,5-difluoro-2-oxo-4-phenylpyridin-1(2H)-yl)-2-methyl-2-(methylsulfonyl)butanoate (77 mg, 0.19 mmol) in tetrahydrofuran:methanol:water (2:2:1 10 mL). The solution was heated to 50° C. and stirred at this temperature for 4 h. The reaction was concentrated and the residue was dissolved in 1 N aq NaOH (50 mL). The aqueous layer was washed with EtOAc (3×50 mL) and acidified to a pH of 3 using concentrated HCl. The solid was collected via filtration and was washed with water (30 mL) and hexanes (30 mL) to afford the title compound as a white solid (70 mg, 95%). MS (LCMS) m/z 398.0 (M+1). $^1$H NMR (400 MHz, METHANOL-d$_4$) δ ppm 1.69-1.79 (m, 3H) 2.30-2.46 (m, 1H) 2.55-2.72 (m, 1H) 3.18 (s, 3H) 3.66 (s, 3H) 4.08-4.22 (m, 1H) 4.23-4.38 (m, 1H) 7.39-7.51 (m, 5H) 7.60 (d, 1H).

Step B) (2R)-4-(5-Fluoro-3-methoxy-2-oxo-4-phenylpyridin-1(2H)-yl)-2-methyl-2-(methylsulfonyl)-N-(tetrahydro-2H-pyran-2-yloxy)butanamide The title compound (52 mg, 83%) was obtained as an off-white solid from (2R)-4-(5-fluoro-3-methoxy-2-oxo-4-phenylpyridin-1(2H)-yl)-2-methyl-2-(methylsulfonyl)butanoic acid (50 mg, 0.13 mmol) using a procedure analogous to that described for the preparation of 2R)-4-{5-fluoro-2-oxo-4-[4-(2H-1,2,3-triazol-2-yl)phenyl]pyridin-1(2H)-yl}-2-methyl-2-(methylsulfonyl)-N-(tetrahydro-2H-pyran-2-yloxy)butanamide, Example 26, Step D. MS (LCMS) m/z 497.0 (M+1).

Step C) (2R)-4-(5-Fluoro-3-methoxy-2-oxo-4-phenylpyridin-1(2H)-yl)-N-hydroxy-2-methyl-2-(methylsulfonyl)butanamide The title compound (20.2 mg, 48%) was obtained as an off-white solid from (2R)-4-(5-fluoro-3-methoxy-2-oxo-4-phenylpyridin-1(2H)-yl)-2-methyl-2-(methylsulfonyl)-N-(tetrahydro-2H-pyran-2-yloxy)butanamide (75 mg, 0.16 mmol) using a procedure analogous to that described for the preparation of (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 413.0 (M+1). $^1$H NMR (400 MHz, METHANOL-d$_4$) δ ppm 1.72 (s, 3H) 2.30-2.50 (m, 1H) 2.55-2.78 (m, 1H) 3.10 (s, 3H) 3.68 (s, 3H) 3.95-4.06 (m, 1H) 4.21-4.37 (m, 1H) 7.37-7.55 (m, 5H) 7.61 (d, 1H).

Example 40

(2R)-4-(5-Fluoro-3-hydroxy-2-oxo-4-phenylpyridin-1(2H)-yl)-N-hydroxy-2-methyl-2-(methylsulfonyl)butanamide

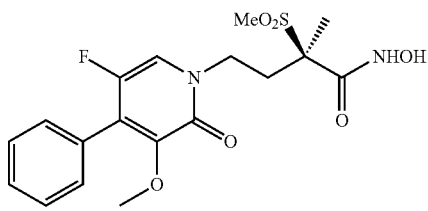

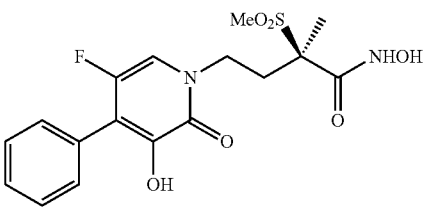

Step A) (2R)-4-(5-Fluoro-3-hydroxy-2-oxo-4-phenylpyridin-1(2H)-yl)-N-hydroxy-2-methyl-2-(methylsulfonyl)butanamide Boron tribromide (760 μL, 0.76 mmol, 1.0 M in dichloromethane) was added to a solution of (2R)-4-(5-fluoro-3-methoxy-2-oxo-4-phenylpyridin-1(2H)-yl)-N-hydroxy-2-methyl-2-(methylsulfonyl)butanamide (156 mg, 0.378 mmol) in DCM (16.0 mL) at 0° C. The reaction was allowed to warm to rt and stirred overnight. The reaction mixture was concentrated to afford a brown solid. The crude product was purified via prepratory HPLC to afford the title compound as a yellow solid (25.4 mg, 16.9%). MS (LCMS) m/z 399.0 (M+1). $^1$H NMR (400 MHz, DMSO-$d_6$) δ ppm 1.59 (s, 3H) 2.11-2.25 (m, 1H) 3.07 (s, 1H) 3.13 (s, 2H) 3.70-3.88 (m, 1H) 4.02-4.26 (m, 1H) 7.11 (d, J=7.81 Hz, 1H) 7.37-7.65 (m, 5H).

Example 41

(2R)-4-[5-Fluoro-4-(4-isoxazol-3-ylphenyl)-2-oxopyridin-1(2H)-yl]-N-hydroxy-2-methyl-2-(methylsulfonyl)butanamide

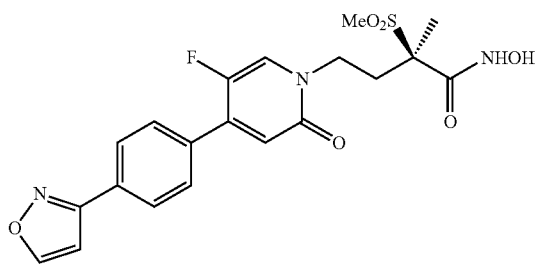

Step A) 3-(4-(4,4,5,5-Tetramethyl-1,3,2-dioxaborolan-2-yl)phenyl)isoxazole

The title compound (730 mg, 67.0%) was obtained as a white solid from 3-(4-bromophenyl)isoxazole (900 mg, 4.02 mmol) using a procedure analogous to that described for the preparation of 2-[4-(4,4,5,5-tetramethyl-1,3,2-dioxaborolan-2-yl)phenyl]-2H-1,2,3-triazole, Example 26, Step A. MS (APCI) m/z 272.1 (M+1). $^1$H NMR (400 MHz, CHLOROFORM-d) δ ppm 1.36-1.41 (m, 12H) 2.42 (s, 3H) 7.61 (d, J=8.00 Hz, 1H) 7.76 (d, J=7.81 Hz, 1H) 7.80 (s, 1H) 7.85 (s, 2H). $^1$H NMR (400 MHz, CHLOROFORM-d) δ ppm 1.35 (s, 12H) 6.66-6.70 (m, 1H) 7.83 (s, 2H) 7.88 (s, 2H) 8.42-8.48 (m, 1H).

Step B) (2R)-4-[5-Fluoro-4-(4-isoxazol-3-ylphenyl)-2-oxopyridin-1(2H)-yl]-2-methyl-2-(methylsulfonyl)-N-(tetrahydro-2H-pyran-2-yloxy)butanamide The title compound (655 mg, 63.4%) was obtained as a colorless oil from 3-(4-(4,4,5,5-tetramethyl-1,3,2-dioxaborolan-2-yl)phenyl)isoxazole (525 mg, 1.94 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (1.00 g, 1.94 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (APCI) m/z 532.3 (M−1). $^1$H NMR (400 MHz, CHLOROFORM-d) δ ppm 1.53-1.97 (m, 9H) 2.31-2.47 (m, 1H) 2.47-2.60 (m, 1H) 3.19 (d, J=2.54 Hz, 3H) 3.53-3.74 (m, 1H) 4.00 (br. s., 1H) 4.12 (s, 1H) 4.27-4.40 (m, 1H) 5.15 (d, J=14.24 Hz, 1H) 6.63-6.75 (m, 2H) 7.42 (d, J=5.46 Hz, 1H) 7.62 (d, J=8.00 Hz, 2H) 7.92 (d, J=8.59 Hz, 2H) 8.49 (d, J=1.56 Hz, 1H) 11.85 (d, J=17.76 Hz, 1H).

Step C) (2R)-4-[5-Fluoro-4-(4-isoxazol-3-ylphenyl)-2-oxopyridin-1(2H)-yl]-N-hydroxy-2-methyl-2-(methylsulfonyl)butanamide A solution of 1.0 M aq HCl (15 mL) was added slowly to a solution of (2R)-4-[5-fluoro-4-(4-isoxazol-3-ylphenyl)-2-oxopyridin-1(2H)-yl]-2-methyl-2-(methylsulfonyl)-N-(tetrahydro-2H-pyran-2-yloxy)butanamide (655 mg, 1.23 mmol) in 1,4-dioxane (30 mL) at rt. The reaction was allowed to stir at rt overnight. The reaction was concentrated to a crude material. Water (30 mL) was added to the crude material and the mixture was boiled for 5 minutes. The mixture was allowed to cool to rt and the solid that formed was collected via filtration and dried under high vacuum to afford the title compound as a light yellow solid (314 mg, 56.9%). MS (APCI) m/z 450.1 (M+1). $^1$H NMR (400 MHz, DMSO-$d_6$) δ ppm 1.55 (s, 3H) 2.10-2.21 (m, 1H) 2.42-2.49 (m, 1H) 3.09 (s, 3H) 3.66-3.85 (m, 1H) 3.96-4.09 (m, 1H) 6.59 (d, J=7.61 Hz, 1H) 7.21 (d, J=1.56 Hz, 1H) 7.71 (dd, J=8.39, 1.76 Hz, 2H) 8.00 (d, J=8.39 Hz, 2H) 8.04 (d, J=6.44 Hz, 1H) 9.03 (d, J=1.56 Hz, 1H) 9.16-9.28 (m, 1H) 11.06 (s, 1H).

Example 42

(2R)-4-[5-Fluoro-4-[4-(1,3-oxazol-2-yl)phenyl]-2-oxopyridin-1(2H)-yl]-N-hydroxy-2-methyl-2-(methylsulfonyl)butanamide

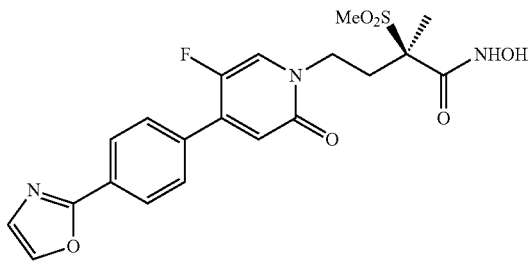

Step A) 2-[4-(4,4,5,5-Tetramethyl-1,3,2-dioxaborolan-2-yl)phenyl]-1,3-oxazole The title compound (240 mg, 34.3%) was obtained as a white solid from 2-(4-iodophenyl)-1,3-oxazole (700 mg, 2.58 mmol) using a procedure analogous to that described for the preparation of 2-[4-(4,4,5,5-tetramethyl-1,3,2-dioxaborolan-2-yl)phenyl]-2H-1,2,3-triazole, Example 26, Step A. MS (APCI) m/z 272.2 (M+1). $^1$H NMR (400 MHz, CHLOROFORM-d) δ ppm 1.35 (s, 12H) 7.23-7.24 (m, 1H) 7.69-7.73 (m, 1H) 7.86-7.91 (m, 2H) 7.98-8.05 (m, 2H).

Step B) (2R)-4-{5-Fluoro-4-[4-(1,3-oxazol-2-yl)phenyl]-2-oxopyridin-1(2H)-yl}-2-methyl-2-(methylsulfonyl)-N-(tetrahydro-2H-pyran-2-yloxy)butanamide The title compound (145 mg, 30.7%) was obtained as a colorless oil from 2-[4-(4,4,5,5-tetramethyl-1,3,2-dioxaborolan-2-yl)phenyl]-1,3-oxazole (240 mg, 0.89 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (435 mg, 0.84 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (APCI) m/z 532.5 (M−1). $^1$H NMR (400 MHz, CHLOROFORM-d) δ ppm 1.52-1.98 (m, 9H) 2.35-2.47 (m, 1H) 2.48-2.60 (m, 1H) 3.20 (d, J=2.93 Hz, 3H) 3.56-3.71 (m, 1H) 3.96-4.07 (m, 1H) 4.12-4.22 (m, 1H) 4.32-4.46 (m, 1H) 5.12-5.23 (m, 1H) 6.69-6.75 (m, 1H) 7.27 (s, 1H) 7.37-7.45 (m, 1H) 7.63 (dd, J=8.39, 1.56 Hz, 2H) 7.75 (s, 1H) 8.14 (d, J=8.39 Hz, 2H) 11.79-11.95 (m, 1H).

Step C) (2R)-4-{5-Fluoro-4-[4-(1,3-oxazol-2-yl)phenyl]-2-oxopyridin-1(2H)-yl}-N-hydroxy-2-methyl-2-(methylsulfonyl)butanamide The title compound (31 mg, 25%) was obtained as a solid from (2R)-4-{5-fluoro-4-[4-(1,3-oxazol-2-yl)phenyl]-2-oxopyridin-1(2H)-yl}-2-methyl-2-(methylsulfonyl)-N-(tetrahydro-2H-pyran-2-yloxy)butanamide (145 mg, 0.27 mmol) using a procedure analogous to that described for the preparation of (2R)-4-[5-fluoro-4-(4-isoxazol-3-ylphenyl)-2-oxopyridin-1(2H)-yl]-N-hydroxy-2-methyl-2-(methylsulfonyl)butanamide, Example 41, Step C. MS (APCI) m/z 450.2 (M+1). $^1$H NMR (400 MHz, DMSO-d$_6$) δ ppm 1.55 (s, 3H) 2.11-2.23 (m, 1H) 2.39-2.47 (m, 1H) 3.09 (s, 3H) 3.61-3.84 (m, 1H) 3.91-4.12 (m, 1H) 6.58 (d, J=7.61 Hz, 1H) 7.41 (s; 1H) 7.72 (d, J=7.02 Hz, 2H) 7.91-8.12 (m, 3H) 8.25 (s, 1H) 9.12-9.29 (m, 1H) 10.87-11.17 (m, 1H).

Example 43

(2R)-4-[5-Fluoro-4-(4-trideuteromethylphenyl)-2-oxopyridin-1(2H)-yl]-N-hydroxy-2-methyl-2-(methylsulfonyl)butanamide

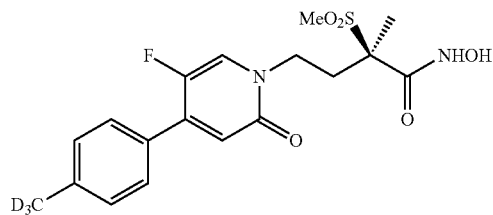

Step A) (2R)-4-[5-Fluoro-4-(4-trideuteromethylphenyl)-2-oxopyridin-1(2H)-yl]-2-methyl-2-(methylsulfonyl)-N-(tetrahydro-2H-pyran-2-yloxy)butanamide The title compound (216 mg, 76.9%) was obtained as a light orange oil from (4-trideuteromethylphenyl)boronic acid (85 mg, 0.61 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (300 mg, 0.58 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (APCI) m/z 482.4 (M−1). $^1$H NMR (400 MHz, CHLOROFORM-d) δ ppm 1.50-1.97 (m, 9H) 2.32-2.44 (m, 1H) 2.44-2.59 (m, 1H) 3.17 (d, J=2.34 Hz, 3H) 3.53-3.69 (m, 1H) 4.00 (br. s., 1H) 4.10-4.20 (m, 1H) 4.31 (br. s., 1H) 5.14 (d, J=14.44 Hz, 1H) 6.65 (dd, J=7.22, 1.56 Hz, 1H) 7.21-7.28 (m, 2H) 7.36 (d, J=5.27 Hz, 1H) 7.38-7.44 (m, 2H) 11.89-12.06 (m, 1H).

Step B) (2R)-4-[5-Fluoro-4-(4-trideuteromethylphenyl)-2-oxopyridin-1(2H)-yl]-N-hydroxy-2-methyl-2-(methylsulfonyl)butanamide The title compound (62 mg, 35%) was obtained as a solid from (2R)-4-[5-fluoro-4-(4-trideuteromethylphenyl)-2-oxopyridin-1(2H)-yl]-2-methyl-2-(methylsulfonyl)-N-(tetrahydro-2H-pyran-2-yloxy)butanamide (145 mg, 0.27 mmol) using a procedure analogous to that described for the preparation of (2R)-4-[5-fluoro-4-(4-isoxazol-3-ylphenyl)-2-oxopyridin-1(2H)-yl]-N-hydroxy-2-methyl-2-(methylsulfonyl)butanamide, Example 41, Step C. MS (APCI) m/z 400.0 (M+1). $^1$H NMR (400 MHz, DMSO-d$_6$) δ ppm 1.54 (s, 3H) 2.14 (br. s., 1H) 2.47 (br. s., 1H) 3.08 (s, 3H) 3.75 (br. s., 1H) 4.02 (br. s., 1H) 6.47 (d, J=7.61 Hz, 1H) 7.28 (d, J=8.00 Hz, 2H) 7.44 (d, J=7.02 Hz, 2H) 7.98 (d, J=6.63 Hz, 1H) 9.21 (s, 1H) 11.07 (s, 1H).

Example 44

(2R)-4-[5-Fluoro-4-(4-trideuteromethoxyphenyl)-2-oxopyridin-1(2H)-yl]-N-hydroxy-2-methyl-2-(methylsulfonyl)butanamide

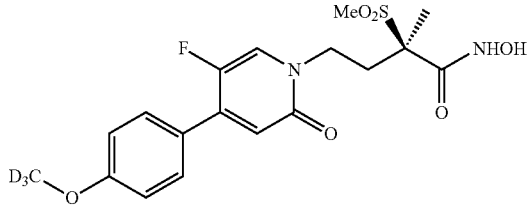

Step A) (2R)-4-[5-Fluoro-4-(4-trideuteromethoxyphenyl)-2-oxopyridin-1(2H)-yl]-2-methyl-2-(methylsulfonyl)-N-(tetrahydro-2H-pyran-2-yloxy)butanamide The title compound (216 mg, 76.9%) was obtained as a colorless oil from (4-trideuteromethoxyphenyl)boronic acid (120 mg, 0.78 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (400 mg, 0.78 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. (122 mg, 31.5%). MS (APCI) m/z 498.3 (M−1). $^1$H NMR (400 MHz, CHLOROFORM-d) δ ppm 1.49-1.98 (m, 9H) 2.38 (dd, J=7.12, 3.80 Hz, 1H) 2.44-2.61 (m, 1H) 3.18 (d, J=2.54 Hz, 3H) 3.65 (d, J=11.51 Hz, 1H) 3.89-4.04 (m, 1H) 4.11-4.22 (m, 1H) 4.24-4.38 (m, 1H) 5.15 (d, J=14.63 Hz, 1H) 6.64 (dd, J=7.41, 1.37 Hz, 1H) 6.96 (d, J=8.78 Hz, 2H) 7.35 (d, J=5.66 Hz, 1H) 7.43-7.51 (m, 2H) 12.02 (d, J=15.02 Hz, 1H).

Step B) (2R)-4-[5-fluoro-4-(4-trideuteromethoxyphenyl)-2-oxopyridin-1(2H)-yl]-N-hydroxy-2-methyl-2-(methylsulfonyl)butanamide The title compound (55 mg, 55%) was obtained as a solid from (2R)-4-[5-fluoro-4-(4-trideuteromethoxyphenyl)-2-oxopyridin-1(2H)-yl]-2-methyl-2-(methylsulfonyl)-N-(tetrahydro-2H-pyran-2-yloxy)butanamide (120 mg, 0.24 mmol) using a procedure analogous to that described for the preparation of (2R)-4-[5-fluoro-4-(4-isoxazol-3-ylphenyl)-2-oxopyridin-1(2H)-yl]-N-hydroxy-2-methyl-2-(methylsulfonyl)butanamide, Example 41, Step C. MS (APCI) m/z 416.1 (M+1). $^1$H NMR (400 MHz, DMSO-d$_6$) δ ppm 1.54 (s, 3H) 2.14 (br. s., 1H) 2.47 (br. s., 1H) 3.08 (s, 3H) 3.74 (br. s., 1H) 4.02 (br. s., 1H) 6.46 (d, J=7.81 Hz, 1H) 7.02 (d, J=8.39 Hz, 2H) 7.51 (d, J=7.41 Hz, 2H) 7.96 (d, J=6.63 Hz, 1H) 9.20 (s, 1H) 11.07 (s, 1H).

Example 45

(2R)-4-[4-(4-Pentadeuteroethoxyphenyl)-5-fluoro-2-oxopyridin-1(2H)-yl]-N-hydroxy-2-methyl-2-(methylsulfonyl)butanamide

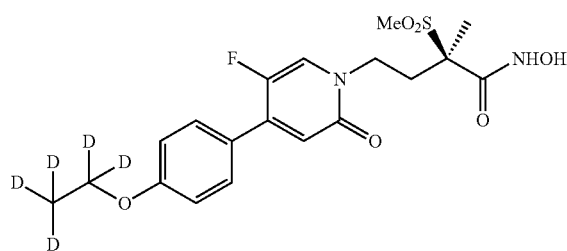

Step A) (2R)-4-[4-(4-Pentadeuteroethoxyphenyl)-5-fluoro-2-oxopyridin-1(2H)-yl]-2-methyl-2-(methylsulfonyl)-N-(tetrahydro-2H-pyran-2-yloxy)butanamide The title compound (184 mg 46.0%) was obtained as a colorless oil from (4-pentadeuteroethoxyphenyl)boronic acid (132 mg, 0.78 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (400 mg, 0.78 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (APCI) m/z 514.4 (M−1). $^1$H NMR (400 MHz, CHLOROFORM-d) δ ppm 1.53-1.97 (m, 9H) 2.39 (dt, J=7.27, 3.68 Hz, 1H) 2.45-2.60 (m, 1H) 3.19 (d, J=2.73 Hz, 3H) 3.65 (d, J=11.51 Hz, 1H) 3.90-4.04 (m, 1H) 4.16 (dd, J=11.22, 2.44 Hz, 1H) 4.24-4.38 (m, 1H) 5.16 (d, J=14.83 Hz, 1H) 6.64 (dd, J=7.42, 1.17 Hz, 1H) 6.95 (d, J=8.59 Hz, 2H) 7.34 (d, J=5.66 Hz, 1H) 7.40-7.52 (m, 2H) 12.03 (br. s., 1H).

Step B) (2R)-4-[4-(4-Pentadeuteroethoxyphenyl)-5-fluoro-2-oxopyridin-1(2H)-yl]-N-hydroxy-2-methyl-2-(methylsulfonyl)butanamide The title compound (152 mg, 98.7%) was obtained as an off-white solid from (2R)-4-[4-(4-pentadeuteroethoxyphenyl)-5-fluoro-2-oxopyridin-1(2H)-yl]-2-methyl-2-(methylsulfonyl)-N-(tetrahydro-2H-pyran-2-yloxy)butanamide (120 mg, 0.24 mmol) using a procedure analogous to that described for the preparation of (2R)-4-[5-fluoro-4-(4-isoxazol-3-ylphenyl)-2-oxopyridin-1(2H)-yl]-N-hydroxy-2-methyl-2-(methylsulfonyl)butanamide, Example 41, Step C. MS (APCI) m/z 432.1 (M+1). $^1$H NMR (400 MHz, DMSO-d$_6$) δ ppm 1.54 (s, 3H) 1.89-2.22 (m, 1H) 2.32-2.47 (m, 1H) 2.92-3.15 (m, 3H) 3.57-3.80 (m, 1H) 4.01 (br. s., 1H) 6.45 (d, J=7.81 Hz, 1H) 7.01 (d, J=8.78 Hz, 2H) 7.50 (d, J=7.22 Hz, 2H) 7.96 (d, J=6.83 Hz, 1H) 9.21 (br. s., 1H) 11.08 (s, 1H).

Example 46

(2R)-4-{4-[4-(Cyclopropyloxy)phenyl]-5-fluoro-2-oxopyridin-1(2H)-yl}-N-hydroxy-2-methyl-2-(methylsulfonyl)butanamide

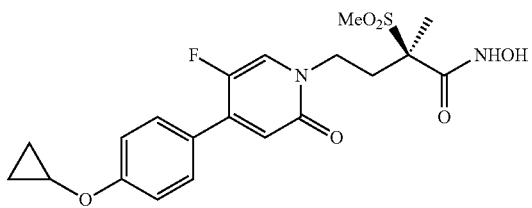

Step A) 2-[4-(Cyclopropyloxy)phenyl]-4,4,5,5-tetramethyl-1,3,2-dioxaborolane

Pd(dppf)Cl$_2$ (770 mg, 0.94 mmol) was added to a degassed suspension of 1-bromo-4-(cyclopropyloxy)benzene (2.0 g, 9.39 mmol), potassium acetate (2.76 g, 28.12 mmol), and 4,4,4',4',5,5,5',5'-octamethyl-2,2'-bi-1,3,2-dioxaborolane (2.62 g, 10.32 mmol) in anhydrous DMSO (20 mL). The reaction was heated to 80° C. and stirred at this temperature for 5 h. The reaction was allowed to cool to rt and diluted with water and diethyl ether. The organic phase was separated and the aqueous phase was extracted with diethyl ether. The organics were combined, dried (MgSO$_4$), filtered, and concentrated in vacuo. Hexanes were added to the residue and the resulting yellow solution was decanted from the brown residue. The yellow solution was concentrated, and the residue was purified via column chromatography using an eluent of 2% ethyl acetate in hexanes to afford title compound as a colorless oil (878 mg, 36%). MS (LCMS) m/z 261.2 (M+1). $^1$H NMR (400 MHz, CHLOROFORM-d) δ ppm 0.74-0.83 (m, 4H) 1.34 (s, 12H) 3.73-3.82 (m, 1H) 7.05 (d, 2H) 7.75 (d, 2H).

Step B) (2R)-4-{4-[4-(Cyclopropyloxy)phenyl]-5-fluoro-2-oxopyridin-1(2H)-yl}-2-methyl-2-(methylsulfonyl)-N-(tetrahydro-2H-pyran-2-yloxy)butanamide The title compound (560 mg 55.3%) was obtained as a colorless oil from 2-[4-(cyclopropyloxy)phenyl]-4,4,5,5-tetramethyl-1,3,2-dioxaborolane (554 mg, 2.13 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (1.0 g, 1.94 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (APCI) m/z 521.4 (M−1). $^1$H NMR (400 MHz, CHLOROFORM-d) δ ppm 0.57-0.82 (m, 4H) 1.42-1.91 (m, 9H) 2.27-2.41 (m, 1H) 2.41-2.58 (m, 1H) 3.13 (s, 4H) 3.45-3.64 (m, 1H) 3.72 (dd, J=5.46, 2.93 Hz, 1H) 3.80-3.98 (m, 1H) 4.12 (d, J=10.93 Hz, 1H) 4.17-4.31 (m, 1H) 5.11 (d, J=13.85 Hz, 1H) 6.59 (d, J=7.41 Hz, 1H) 6.97-7.13 (m, 2H) 7.36 (d, J=5.46 Hz, 1H) 7.43 (d, J=8.59 Hz, 2H) 11.82-12.08 (m, 1H).

Step B) (R)-4-(4-(4-Cyclopropoxyphenyl)-5-fluoro-2-oxopyridin-1(2H)-yl)-N-hydroxy-2-methyl-2-(methylsulfonyl)butanamide The title compound (280 mg, 59.6%) was obtained as an off-white solid from (2R)-4-(4-(4-cyclopropoxyphenyl)-5-fluoro-2-oxopyridin-1(2H)-yl)-2-methyl-2-(methylsulfonyl)-N-(tetrahydro-2H-pyran-2-yloxy)butanamide (560 mg, 1.07 mmol) using a procedure analogous to that described for the preparation of (R)-4-(5-fluoro-4-(4-(isoxazol-3-yl)phenyl)-2-oxopyridin-1(2H)-yl)-N-hydroxy-2-methyl-2-(methylsulfonyl)butanamide, Example 41, Step C. MS (APCI) m/z 439.0 (M+1). $^1$H NMR (400 MHz, DMSO-$d_6$)™ ppm 0.55-0.69 (m, 2H) 0.74-0.85 (m, 2H) 1.54 (s, 3H) 2.03-2.26 (m, 1H) 2.33-2.46 (m, 1H) 3.08 (s, 3H) 3.64-3.80 (m, 1H) 3.88 (dt, J=6.05, 3.02 Hz, 1H) 3.94-4.10 (m, 1H) 6.46 (d, J=7.81 Hz, 1H) 7.02-7.23 (m, 2H) 7.52 (dd, J=8.78, 1.95 Hz, 2H) 7.97 (d, J=6.63 Hz, 1H) 9.21 (s, 1H) 11.08 (s, 1H).

Example 47

(2R)-4-[4-(2,2-Difluoro-1,3-benzodioxol-5-yl)-5-fluoro-2-oxopyridin-1(2H)-yl]-N-hydroxy-2-methyl-2-(methylsulfonyl)butanamide

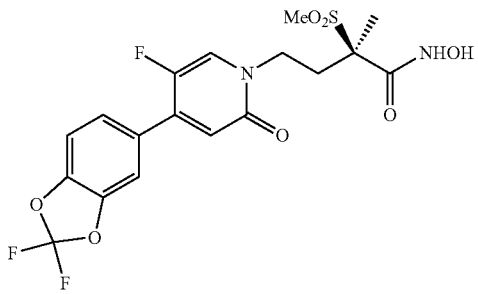

Step A) (2R)-4-[4-(2,2-Difluoro-1,3-benzodioxol-5-yl)-5-fluoro-2-oxopyridin-1(2H)-yl]-2-methyl-2-(methylsulfonyl)-N-(tetrahydro-2H-pyran-2-yloxy)butanamide The title compound (560 mg 55.3%) was obtained as a colorless oil from (2,2-difluoro-1,3-benzodioxol-5-yl)boronic acid (129 mg, 0.639 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (300 g, 0.581 mmol) using a procedure analogous to that described for the preparation of (2R)-4-[5-fluoro-4-(3-fluoro-4-methoxyphenyl)-2-oxopyridin-1(2H)-yl]-2-methyl-2-(methylsulfonyl)-N-(tetrahydro-2H-pyran-2-yloxy)butanamide, Example 19, Step A. MS (LCMS) m/z 545.3 (M−1).

Step B) (2R)-4-[4-(2,2-Difluoro-1,3-benzodioxol-5-yl)-5-fluoro-2-oxopyridin-1(2H)-yl]-N-hydroxy-2-methyl-2-(methylsulfonyl)butanamide Aqueous HCl (1.42 mL, 1.42 mmol) was added to a solution of (2R)-4-[4-(2,2-Difluoro-1,3-benzodioxol-5-yl)-5-fluoro-2-oxopyridin-1(2H)-yl]-2-methyl-2-(methylsulfonyl)-N-(tetrahydro-2H-pyran-2-yloxy)butanamide (259 mg, 0.474 mmol) in ethanol (5 mL) and water (2 mL) and the reaction was stirred overnight at rt. The solid was collected via filtration, washed with water (5×3 mL) and dried under reduced pressure to afford the title compound (143 mg, 65.3%). $^1$H NMR (400 MHz, DMSO-$d_6$) δ ppm 1.58 (s, 3H) 2.07-2.24 (m, 1H) 2.36-2.49 (m, 1H) 3.11 (s, 3H) 3.68-3.86 (m, 1H) 3.98-4.13 (m, 1H) 6.58 (d, J=7.61 Hz, 1H) 7.36-7.49 (m, 1H) 7.55 (d, J=8.39 Hz, 1H) 7.68 (s, 1H) 8.06 (d, J=6.63 Hz, 1H) 9.24 (br. s., 1H) 11.08 (s, 1H).

Example 48

(2R)-4-[5-Fluoro-2-oxo-4-(phenylethynyl)pyridin-1(2H)-yl]-N-hydroxy-2-methyl-2-(methylsulfonyl)butanamide

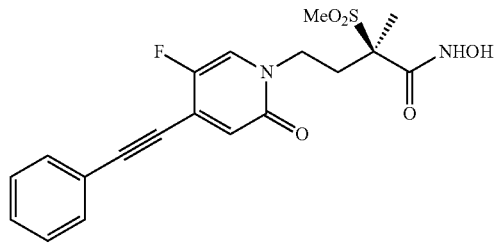

Step A) Ethyl (2R)-4-[5-fluoro-2-oxo-4-(phenylethynyl)pyridin-1(2H)-yl]-2-methyl-2-(methylsulfonyl)butanoate A solution of ethyl (2R)-4-(5-fluoro-4-iodo-2-oxopyridin-1(2H)-yl)-2-methyl-2-(methylsulfonyl)butanoate (500 mg, 1.12 mmol) and diisopropylethylamine (6.0 mL, 30 mmol) in tetrahydrofuran (15 mL) was degassed with nitrogen. Pd(PPh$_3$)$_4$ (65.4 mg, 0.056) and copper iodide (21.8 mg, 0.112 mmol) were added to the solution, followed by phenylacetylene (150 uL, 1.4 mmol). The reaction was allowed to stir until complete via TLC. The reaction was diluted with EtOAc (100 mL) and washed with saturated aq NH$_4$Cl (100 mL) and brine (100 mL), dried (MgSO$_4$), filtered, and concentrated. The crude residue was purified via flash chromatography using a Varian SF15-24 g column and an eluent of EtOAc in hexanes (30-80%) to afford the title compound as a yellow solid (389 mg, 82.6%). MS (LCMS) m/z 420.0 (M+1). $^1$H NMR (400 MHz, CHLOROFORM-d) δ ppm 1.35 (t, 3H) 1.75 (s, 3H) 2.42-2.61 (m, 2H) 3.11 (s, 3H) 3.91-4.00 (m, 1H) 4.19-4.27 (m, 1H) 4.30 (q, J=7.02 Hz, 2H) 6.72 (d, J=6.63 Hz, 1H) 7.27 (t, J=2.34 Hz, 2H) 7.35-7.44 (m, 2H) 7.55-7.60 (m, 2H).

Step B) (2R)-4-[5-Fluoro-2-oxo-4-(phenylethynyl)pyridin-1(2H)-yl]-2-methyl-2-(methylsulfonyl)butanoic acid The title compound (195.1 mg, 72.1%) was obtained as a white solid from ethyl (2R)-4-[5-fluoro-2-oxo-4-(phenylethynyl)pyridin-1(2H)-yl]-2-methyl-2-(methylsulfonyl)butanoate (290 mg, 0.52 mmol) using a procedure analogous to that described for the preparation of ethyl (2R)-4-{5-fluoro-2-oxo-4-[(2H-1,2,3-triazol-2-yl)phenyl]pyridin-1(2H)-yl}-2-methyl-2-(methylsulfonyl)butanoate, Example 26, Step C. MS (LCMS) m/z 392.0 (M+1). $^1$H NMR (400 MHz, DMSO-$d_6$) δ ppm 1.55 (s, 3H) 2.10-2.24 (m, 0H) 2.40-2.56

(m, 1H) 3.16 (s, 3H) 3.87-4.06 (m, 2H) 6.65 (d, J=6.83 Hz, 1H) 7.43-7.55 (m, 3H) 7.57-7.65 (m, 2H) 8.07 (d, J=5.46 Hz, 1H).

Step C) (2R)-4-[5-Fluoro-2-oxo-4-(phenylethynyl)pyridin-1(2H)-yl]-2-methyl-2-(methylsulfonyl)-N-(tetrahydro-2H-pyran-2-yloxy)butanamide The title compound (232 mg, 95.0%) was obtained as a white solid from (2R)-4-[5-fluoro-2-oxo-4-(phenylethynyl) 89yridine-1(2H)-yl]-2-methyl-2-(methylsulfonyl)butanoic acid (195.1 mg, 0.50 mmol) using a procedure analogous to that described for the preparation of (2R)-4-{5-fluoro-2-oxo-4-[4-(2H-1,2,3-triazol-2-yl)phenyl]pyridin-1(2H)-yl}-2-methyl-2-(methylsulfonyl)-N-(tetrahydro-2H-pyran-2-yloxy) butanamide Example 26, Step D.

Step D) (2R)-4-[5-Fluoro-2-oxo-4-(phenylethynyl)90yridine-1(2H)-yl]-N-hydroxy-2-methyl-2-(methylsulfonyl)butanamide The title compound (124.4 mg, 64.7%) was obtained as a white solid from (2R)-4-[5-fluoro-2-oxo-4-(phenylethynyl)90yridine-1(2H)-yl]-2-methyl-2-(methylsulfonyl)-N-(tetrahydro-2H-pyran-2-yloxy)butanamide (232 mg, 0.47 mmol) using a procedure analogous to that described for the preparation of (2R)-4-{5-Fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 407.0 (M+1). $^1$H NMR (400 MHz, DMSO-$d_6$) δ ppm 1.56 (s, 3H) 2.04-2.21 (m, 1H) 2.37-2.49 (m, 1H) 3.10 (s, 3H) 3.69-3.85 (m, 1H) 3.92-4.12 (m, 1H) 6.69 (d, 1H) 7.39-7.57 (m, 3H) 7.57-7.68 (m, 2H) 8.05 (d, J=5.46 Hz, 1H) 9.22 (s, 1H) 11.04 (s, 1H).

Example 49

(2R)-4-{5-Fluoro-2-oxo-4-[3-(1,3-thiazol-2-yloxy)phenyl]pyridin-1(2H)-yl}-N-hydroxy-2-methyl-2-(methylsulfonyl)butanamide

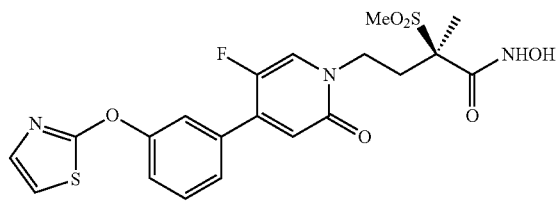

Step A) 2-(3-Iodophenoxy)-1,3-thiazole

Cesium carbonate (4.52 g, 13.87 mmol) was added to 2-bromo-1,3-thiazole (1.90 g, 11.6 mmol) and 3-iodophenol (2.54 g, 11.5 mmol) in anhydrous DMF (30 mL). The reaction was heated to 135° C. and stirred at this temperature overnight. The reaction was allowed to cool, then was poured into water (100 mL), and extracted with EtOAc (3×100 mL). The combined organics were washed with brine (100 mL), dried (MgSO$_4$), filtered, and concentrated. The crude product was purified via flash chromatography using a Varian SF15-24 g column and an eluent of EtOAc in hexanes (0-10%) to afford the title compound as a yellow oil (2.52 g, 71.8%). MS (LCMS) m/z 304.1 (M+1).

Step B) 2-[3-(4,4,5,5-Tetramethyl-1,3,2-dioxaborolan-2-yl)phenoxy]-1,3-thiazole The title compound (1.33 g) was prepared as a crude brown solid from 2-(3-iodophenoxy)-1,3-thiazole (500 mg, 1.65 mmol) using a procedure analogous to that described for 2-[4-(4,4,5,5-tetramethyl-1,3,2-dioxaborolan-2-yl)phenyl]-2H-tetrazole, Example 1, Step A. MS (LCMS) m/z 304.0 (M+1).

Step C) Ethyl (2R)-4-{5-fluoro-2-oxo-4-[3-(1,3-thiazol-2-yloxy)phenyl]pyridin-1(2H)-yl}-2-methyl-2-(methylsulfonyl)butanoate The title compound (534 mg) was prepared as a crude brown oil from 2-[3-(4,4,5,5-tetramethyl-1,3,2-dioxaborolan-2-yl)phenoxy]-1,3-thiazole (1.33 g, 4.39 mmol) and T2 (400 mg, 0.90 mmol) using a procedure analogous to that described for ethyl (2R)-4-[5-fluoro-2-oxo-4-(4-{[trans-4-(tetrahydro-2H-pyran-2-yloxy)cyclohexyl]methoxy}phenyl)pyridin-1(2H)-yl]-2-methyl-2-(methylsulfonyl)butanoate, Example 18, Step D. MS (LCMS) m/z 495.2 (M+1).

Step D) (2R)-4-{5-Fluoro-2-oxo-4-[3-(1,3-thiazol-2-yloxy)phenyl]pyridin-1(2H)-yl}-2-methyl-2-(methylsulfonyl)butanoic acid The title compound (144 mg, 28.4%) was prepared as an off-white solid from ethyl (2R)-4-{5-fluoro-2-oxo-4-[3-(1,3-thiazol-2-yloxy)phenyl]pyridin-1(2H)-yl}-2-methyl-2-(methylsulfonyl)butanoate (538 mg, 1.09 mmol) using a procedure analogous to that described for (2R)-4-{5-fluoro-2-oxo-4-[4-(2H-1,2,3-triazol-2-yl)phenyl]pyridin-1(2H)-yl}-2-methyl-2-(methylsulfonyl)butanoic acid, Example 26, Step C. MS (LCMS) m/z 467.1 (M+1). $^1$H NMR (400 MHz, DMSO-$d_6$) δ ppm 1.57 (s, 3H) 2.12-2.27 (m, 1H) 3.17 (s, 3H) 3.85-4.11 (m, 2H) 6.55 (d, J=7.61 Hz, 1H) 7.24-7.35 (m, 2H) 7.44-7.66 (m, 4H) 8.07 (d, J=6.44 Hz, 1H).

Step E) (2R)-4-{5-Fluoro-2-oxo-4-[3-(1,3-thiazol-2-yloxy)phenyl]pyridin-1(2H)-yl}-2-methyl-2-(methylsulfonyl)-N-(tetrahydro-2H-pyran-2-yloxy)butanamide The title compound (115 mg, 65.8%) was prepared as an off-white solid from (2R)-4-{5-fluoro-2-oxo-4-[3-(1,3-thiazol-2-yloxy)phenyl]pyridin-1(2H)-yl}-2-methyl-2-(methylsulfonyl)butanoic acid (144 mg, 0.31 mmol) using a procedure analogous to that described for (2R)-4-{5-fluoro-2-oxo-4-[4-(2H-1,2,3-triazol-2-yl)phenyl]pyridin-1(2H)-yl}-2-methyl-2-(methylsulfonyl)-N-(tetrahydro-2H-pyran-2-yloxy)butanamide, Example 26, Step D. MS (LCMS) m/z 566.2 (M−1).

Step F) (2R)-4-{5-fluoro-2-oxo-4-[3-(1,3-thiazol-2-yloxy)phenyl]pyridin-1(2H)-yl}-N-hydroxy-2-methyl-2-(methylsulfonyl)butanamide The title compound (66.8 mg, 68.4%) was prepared as a white solid from (2R)-4-{5-fluoro-2-oxo-4-[3-(1,3-thiazol-2-yloxy)phenyl]pyridin-1(2H)-yl}-2-methyl-2-(methylsulfonyl)-N-(tetrahydro-2H-pyran-2-yloxy)butanamide (115 mg, 0.20 mmol) using a procedure analogous to that described for (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide, Example 26, Step E. MS (LCMS) m/z 482.2 (M+1). $^1$H NMR (400 MHz, DMSO-d$_6$) δ ppm 1.57 (s, 3H) 2.09-2.23 (m, 1H) 3.11 (s, 3H) 3.70-3.87 (m, 1H) 3.97-4.14 (m, 1H) 6.58 (d, J=7.61 Hz, 1H) 7.25-7.35 (m, 2H) 7.45-7.67 (m, 4H) 8.06 (d, J=6.44 Hz, 1H) 9.23 (s, 1H) 11.08 (s, 1H).

Biological Examples

In order to assess the compounds biological activity, selected in vitro assays were conducted on selected compounds. One of the assays measured the compounds ability to disrupt the synthesis of lipopolysaccharide, LPS, which is a component of the outer membrane of Gram-negative bacteria. Disruption of this synthesis is lethal to the bacteria. The assay determined the compound's ability to inhibit LpxC, which is the first enzyme in the biosynthetic pathway for LPS (measured as IC$_{50}$). Additionally, MICs (minimal inhibitory concentrations) were determined for several bacteria. The specific protocols are described below:

A) IC$_{50}$ Assay, LpxC Enzyme from *P. aeruginosa* (Labeled as PA LpxC Enzyme IC$_{50}$):

IC$_{50}$ determination in the LpxC enzyme assay was carried out in a similar manner to that described by Malikzay et al in the 2006 Poster, Screening LpxC (UDP-3-O—(R-3-hydroxymyristoyl)-GlcNAc deacetylase) using BioTrove RapidFire HTS Mass Spectrometry (aNew Lead Discovery and bInflammation and Infectious Disease, cStructural Chemistry, Schering-Plough Research Institute, Kenilworth, N.J. 07033, (BioTrove, Inc. 12 Gill St., Suite 4000, Woburn, Mass. 01801). Briefly, *Pseudomonas aeruginosa* LpxC enzyme (0.1 nM) purified from *E. coli*-overexpressing bacteria was incubated at 25° C. in a final volume of 50 ul containing 0.5 uM UDP-3-O—(R-3-hydroxydecanoyl)-N-acetylglucosamine, 1 mg/mL BSA, and 50 mM sodium phosphate buffer, pH 8.0 in the presence and absence of inhibitor compound. At the end of 1 hour, 5 ul of 1 N HCl was added to stop the enzyme reaction, the plates were centrifuged, and then processed with the BioTrove Rapidfire HTMS Mass Spectrometry System. A no-enzyme control was used in calculating the IC$_{50}$ values from the percent conversion values.

B) MIC determinations:

The in vitro antibacterial activity of compounds described in the Examples was evaluated by minimum inhibitory concentration (MIC) testing according to Clinical and Laboratory Standards Institute (CLSI). See: Clinical and Laboratory Standards Institute. Methods for Dilution Antimicrobial Susceptibility Tests for Bacteria that Grow Aerobically; Approved Standard-Eighth Edition. CLSI document M7-A8 [ISBN 1-56238-689-1]. Clinical and Laboratory Standards Institute, 940 West Valley Road, Suite 1400, Wayne, Pa. 19087-1898 USA, 2006; also Clinical and Laboratory Standards Institute. Performance Standards for Antimicrobial Susceptibility Testing; Twentieth Informational Supplement. CLSI document M100-S20 [ISBN 1-56238-716-2]. Clinical and Laboratory Standards Institute.

The MIC determination is a standard laboratory method for evaluating the antibacterial activity of a compound. The MIC represents the lowest drug concentration that inhibits visible growth of bacteria following overnight incubation. In order to determine the MIC value, a range of drug concentrations (e.g. 0.06 μg/mL to 64 μg/mL) are incubated with a defined strain of bacteria. Typically, the drug concentration range is broken down into 2-fold increments (e.g. 0.06 μg/mL, 0.12 μg/mL. 0.25 μg/mL, 0.50 μg/mL, 1.0 μg/mL, etc.) and the various drug concentrations are all individually incubated overnight with approximately the same number of bacteria. The MIC is then determined by visually inspecting the drug effect at each concentration, and identifying the lowest drug concentration that has inhibited bacterial growth as compared to the drug free control. Typically, bacteria continue to grow at drug concentrations lower than the MIC and don't grow at concentrations at and above the MIC.

The MIC values described in Table 2 and 3 below were derived from assays wherein each test compound was evaluated in duplicate. In cases where the duplicate values varied by 0-2-fold, the lower of the two values was reported below. Generally speaking, if the duplicate values varied by more than 2-fold, the assay was considered non-valid and was repeated until the variation between duplicate runs was ≤2-fold. In line with the CLSI guidelines referred to above, both control organisms and reference compounds were utilized in each MIC assay to provide proper quality control. MIC values generated with these control organisms and reference compounds were required to fall within a defined range for the assay to be considered valid and be included herein. Those skilled in the art will recognize that MIC values can and do vary from experiment to experiment. Generally speaking, it should be recognized that MIC values often vary +/−2-fold from experiment to experiment. While a single MIC is reported for each compound and each microorganism, the reader should not conclude that each compound was only tested once. Several of the compounds were subjected to multiple tests. The data reported in Tables 2 and 3 is reflective of the compounds relative activity and different MICs may have been generated on these occasions in line with the guidelines described above.

The following bacterial strains were used in these MIC determinations:

1) *Pseudomonas aeruginosa* UI-18: Wild-type, labeled as PA-7 in Tables 2 and 3;

2) *Acinetobacter baumannii/haemolyticus*: Multidrug-resistant clinical isolate labeled as AB-3167 in Tables 2 and 3;

3) *Escherichia coli* EC-1: VOGEL, mouse virulent labeled as EC-1 in Tables 2 and 3;

4) *Klebsiella pneumoniae*: Ciprofloxacin-resistant isolate, expresses extended-spectrum beta-lactamases (ESBL), clinical isolate, labeled as KP-3700 in Tables 2 and 3.

Table 2, below, shows the results that were obtained with the final products described in Examples 1-47. If a particular table entry is left blank, then the data is not available at the current time.

Column 1 corresponds to the Example number, column 2 provides the IUPAC name, column 3 provides the results from the LpxC enzyme assay described above, and columns 4-7 provide the MIC data as described above.

TABLE 2

| Example | IUPAC NAME | PA:IC50 (μM) | AB-3167 (μg/mL) | EC-1 (μg/mL) | KP-3700 (μg/mL) | PA-7 (μg/mL) |
|---|---|---|---|---|---|---|
| 1 | (2R)-4-{5-fluoro-2-oxo-4-[4-(2H-tetrazol-2-yl)phenyl]pyridin-1(2H)- | 0.00149 | >64.0 | >64.0 | >64.0 | 32 |

TABLE 2-continued

| Example | IUPAC NAME | PA:IC50 (μM) | AB-3167 (μg/mL) | EC-1 (μg/mL) | KP-3700 (μg/mL) | PA-7 (μg/mL) |
|---|---|---|---|---|---|---|
|  | yl}-N-hydroxy-2-methyl-2-(methylsulfonyl)butanamide |  |  |  |  |  |
| 2 | (2R)-4-[5-fluoro-4-(2-fluoro-3-methylphenyl)-2-oxopyridin-1(2H)-yl]-N-hydroxy-2-methyl-2-(methylsulfonyl)butanamide | 0.000595 | >64.0 | 0.25 | 1 | 0.25 |
| 3 | (2R)-4-[4-(4-chlorophenyl)-5-fluoro-2-oxopyridin-1(2H)-yl]-N-hydroxy-2-methyl-2-(methylsulfonyl)butanamide | 0.000325 | 64 | 0.25 | 1 | 0.25 |
| 4 | (2R)-4-[5-fluoro-4-(2-fluorophenyl)-2-oxopyridin-1(2H)-yl]-N-hydroxy-2-methyl-2-(methylsulfonyl)butanamide | 0.000717 | >64.0 | 2 | 4 | 0.5 |
| 5 | (2R)-4-[4-(2,3-dihydro-1-benzofuran-5-yl)-5-fluoro-2-oxopyridin-1(2H)-yl]-N-hydroxy-2-methyl-2-(methylsulfonyl)butanamide | 0.000822 | >64.0 | 1 | 2 | 1 |
| 6 | (2R)-4-[4-(3,4-difluorophenyl)-5-fluoro-2-oxopyridin-1(2H)-yl]-N-hydroxy-2-methyl-2-(methylsulfonyl)butanamide | 0.000833 | >64.0 | 1 | 2 | 0.5 |
| 7 | (2R)-4-{5-fluoro-2-oxo-4-[4-(2,2,2-trifluoroethoxy)phenyl]pyridin-1(2H)-yl}-N-hydroxy-2-methyl-2-(methylsulfonyl)butanamide | 0.000576 | >64.0 | 0.25 | 2 | 1 |
| 8 | (2R)-4-[4-(3,4-dihydro-2H-chromen-6-yl)-5-fluoro-2-oxopyridin-1(2H)-yl]-N-hydroxy-2-methyl-2-(methylsulfonyl)butanamide | 0.000377 | >64.0 | 0.5 | 2 | 1 |
| 19 | (2R)-4-{5-fluoro-4-[4-(methylthio)phenyl]-2-oxopyridin-1(2H)-yl}-N-hydroxy-2-methyl-2-(methylsulfonyl)butanamide | 0.00051 | >64.0 | 0.25 | 1 | 0.5 |
| 10 | (2R)-4-[4-(4-ethoxyphenyl)-5-fluoro-2-oxopyridin-1(2H)-yl]-N-hydroxy-2-methyl-2-(methylsulfonyl)butanamide | 0.000823 | >64.0 | 0.25 | 1 | 1 |
| 11 | (2R)-4-[5-fluoro-2-oxo-4-(4-propylphenyl)pyridin-1(2H)-yl]-N-hydroxy-2-methyl-2-(methylsulfonyl)butanamide | 0.000482 | >64.0 | 0.125 | 0.5 | 0.5 |
| 12 | (2R)-4-{5-fluoro-2-oxo-4-[4-(pentafluoro-6λ-sulfanyl)phenyl]pyridin-1(2H)-yl}-N-hydroxy-2-methyl-2-(methylsulfonyl)butanamide | 0.00114 | >64.0 | 4 | 16 | 4 |
| 13 | (2R)-4-[5-fluoro-4-(3-methylphenyl)-2-oxopyridin-1(2H)-yl]-N-hydroxy-2-methyl-2-(methylsulfonyl)butanamide | 0.00105 | >64.0 | 1 | 4 | 1 |
| 14 | (2R)-4-[5-fluoro-4-(4-fluoro-3-methylphenyl)-2-oxopyridin-1(2H)-yl]-N-hydroxy-2-methyl-2-(methylsulfonyl)butanamide | 0.000758 | >64.0 | 0.5 | 2 | 0.5 |
| 15 | (2R)-4-{5-fluoro-4-[4-(oxetan-3-yloxy)phenyl]-2-oxopyridin-1(2H)-yl}-N-hydroxy-2-methyl-2-(methylsulfonyl)butanamide | 0.00205 | >64.0 | 16 | 32 | 16 |
| 16 | (2R)-4-[4-(4-chloro-2-fluorophenyl)-5-fluoro-2-oxopyridin-1(2H)-yl]-N-hydroxy-2-methyl-2-(methylsulfonyl)butanamide | 0.000336 | >64.0 | 0.25 | 1 | 0.5 |
| 17 | (2R)-4-[5-fluoro-4-(2-fluoro-3-methoxyphenyl)-2-oxopyridin-1(2H)-yl]-N-hydroxy-2-methyl-2-(methylsulfonyl)butanamide | 0.0005 | >64.0 | 0.5 | 1 | 1 |
| 18 | (2R)-4-[5-fluoro-4-{4-[(trans-4-hydroxycyclohexyl)methoxy]phenyl}-2-oxopyridin-1(2H)-yl]-N-hydroxy-2-methyl-2-(methylsulfonyl)butanamide | 0.000463 | >64.0 | 0.125 | 2 | 1 |
| 19 | (2R)-4-[5-fluoro-4-(3-fluoro-4-methoxyphenyl)-2-oxopyridin-1(2H)- | 0.000879 | >64.0 | 2 | 4 | 1 |

TABLE 2-continued

| Example | IUPAC NAME | PA:IC50 (μM) | AB-3167 (μg/mL) | EC-1 (μg/mL) | KP-3700 (μg/mL) | PA-7 (μg/mL) |
|---|---|---|---|---|---|---|
|  | yl]-N-hydroxy-2-methyl-2-(methylsulfonyl)butanamide |  |  |  |  |  |
| 20 | (2R)-4-[5-fluoro-2-oxo-4-(4-pyrimidin-2-ylphenyl)pyridin-1(2H)-yl]-N-hydroxy-2-methyl-2-(methylsulfonyl)butanamide | 0.000945 | >64.0 | 0.125 | 0.5 | 1 |
| 21 | (2R)-4-{5-fluoro-4-[4-(5-methoxypyrimidin-2-yl)phenyl]-2-oxopyridin-1(2H)-yl}-N-hydroxy-2-methyl-2-(methylsulfonyl)butanamide | 0.000436 | >64.0 | 0.125 | 0.5 | 1 |
| 22 | (2R)-4-{5-fluoro-4-[4-(4-methoxy-2H-1,2,3-triazol-2-yl)phenyl]-2-oxopyridin-1(2H)-yl}-N-hydroxy-2-methyl-2-(methylsulfonyl)butanamide | 0.000181 | >64.0 | ≤0.0600 | 0.125 | 0.5 |
| 23 | (2R)-4-{5-fluoro-4-[4-(4-methyl-2H-1,2,3-triazol-2-yl)phenyl]-2-oxopyridin-1(2H)-yl}-N-hydroxy-2-methyl-2-(methylsulfonyl)butanamide | 0.000287 | >64.0 | 0.06 | 0.125 | 0.5 |
| 24 | (2R)-4-(5-fluoro-2-oxo-4-quinoxalin-6-ylpyridin-1(2H)-yl)-N-hydroxy-2-methyl-2-(methylsulfonyl)butanamide | 0.00123 | >64.0 | 4 | 8 | 4 |
| 25 | (2R)-4-[5-fluoro-4-(3-methoxyphenyl)-2-oxopyridin-1(2H)-yl]-N-hydroxy-2-methyl-2-(methylsulfonyl)butanamide | 0.000412 | >64.0 | 1 | 4 | 2 |
| 26 | (2R)-4-{5-fluoro-2-oxo-4-[4-(2H-1,2,3-triazol-2-yl)phenyl]pyridin-1(2H)-yl}-N-hydroxy-2-methyl-2-(methylsulfonyl)butanamide | 0.0000743 | >64.0 | ≤0.0600 | ≤0.0600 | 0.25 |
| 27 | (2R)-4-[5-fluoro-4-(2-fluoro-4-methoxyphenyl)-2-oxopyridin-1(2H)-yl]-N-hydroxy-2-methyl-2-(methylsulfonyl)butanamide | 0.0000498 | >64.0 | 0.25 | 0.5 | 0.5 |
| 28 | (2R)-4-[5-fluoro-4-(4-methoxyphenyl)-2-oxopyridin-1(2H)-yl]-N-hydroxy-2-methyl-2-(methylsulfonyl)butanamide | 0.000564 | >64.0 | 1 | 1 | 0.5 |
| 29 | (2R)-4-[5-fluoro-4-(4-methylphenyl)-2-oxopyridin-1(2H)-yl]-N-hydroxy-2-methyl-2-(methylsulfonyl)butanamide | 0.000514 | >64.0 | 0.5 | 1 | 0.5 |
| 30 | (2R)-4-{5-fluoro-2-oxo-4-[4-(trifluoromethoxy)phenyl]pyridin-1(2H)-yl}-N-hydroxy-2-methyl-2-(methylsulfonyl)butanamide | 0.000106 | >64.0 | 0.25 | 2 | 0.5 |
| 31 | (2R)-4-[5-fluoro-4-(4-fluorophenyl)-2-oxopyridin-1(2H)-yl]-N-hydroxy-2-methyl-2-(methylsulfonyl)butanamide | 0.000213 | >64.0 | 1 | 4 | 0.5 |
| 32 | (2R)-4-{5-fluoro-4-[4-(6-methoxypyridin-3-yl)phenyl]-2-oxopyridin-1(2H)-yl}-N-hydroxy-2-methyl-2-(methylsulfonyl)butanamide | 0.0004 | >64.0 | ≤0.0600 | 1 | 1 |
| 33 | (2R)-4-{4-[4-(difluoromethoxy)phenyl]-5-fluoro-2-oxopyridin-1(2H)-yl}-N-hydroxy-2-methyl-2-(methylsulfonyl)butanamide | 0.0000606 | >64.0 | 0.5 | 2 | 0.5 |
| 34 | (2R)-4-[5-fluoro-4-(4-methoxy-3-methylphenyl)-2-oxopyridin-1(2H)-yl]-N-hydroxy-2-methyl-2-(methylsulfonyl)butanamide | 0.000834 | >64.0 | 0.25 | 2 | 0.5 |
| 35 | (2R)-4-{4-[4-(difluoromethoxy)-3-fluorophenyl]-5-fluoro-2-oxopyridin-1(2H)-yl}-N-hydroxy-2-methyl-2-(methylsulfonyl)butanamide | 0.000589 | >64.0 | 1 | 2 | 0.5 |
| 36 | (2R)-4-{5-fluoro-4-[3-fluoro-4-(2H-1,2,3-triazol-2-yl)phenyl]-2- | 0.000398 | >64.0 | 0.5 | 1 | 1 |

TABLE 2-continued

| Example | IUPAC NAME | PA:IC50 (μM) | AB-3167 (μg/mL) | EC-1 (μg/mL) | KP-3700 (μg/mL) | PA-7 (μg/mL) |
|---|---|---|---|---|---|---|
| | oxopyridin-1(2H)-yl}-N-hydroxy-2-methyl-2-(methylsulfonyl)butanamide | | | | | |
| 37 | (2R)-4-{5-fluoro-4-[3-methyl-4-(2H-1,2,3-triazol-2-yl)phenyl]-2-oxopyridin-1(2H)-yl}-N-hydroxy-2-methyl-2-(methylsulfonyl)butanamide | | >64.0 | 0.5 | 1 | 1 |
| 38 | (2R)-4-(3,5-difluoro-2-oxo-4-phenylpyridin-1(2H)-yl)-N-hydroxy-2-methyl-2-(methylsulfonyl)butanamide | 0.00055 | >64.0 | 1 | 2 | 0.5 |
| 39 | (2R)-4-(5-fluoro-3-methoxy-2-oxo-4-phenylpyridin-1(2H)-yl)-N-hydroxy-2-methyl-2-(methylsulfonyl)butanamide | 0.00807 | 64 | 4 | 8 | 8 |
| 40 | (2R)-4-(5-fluoro-3-hydroxy-2-oxo-4-phenylpyridin-1(2H)-yl)-N-hydroxy-2-methyl-2-(methylsulfonyl)butanamide | >0.100 | 64 | 16 | 32 | 16 |
| 41 | (2R)-4-[5-fluoro-4-(4-isoxazol-3-ylphenyl)-2-oxopyridin-1(2H)-yl]-N-hydroxy-2-methyl-2-(methylsulfonyl)butanamide | 0.000237 | 16 | 0.5 | 0.25 | 0.5 |
| 42 | (2R)-4-{5-fluoro-4-[4-(1,3-oxazol-2-yl)phenyl]-2-oxopyridin-1(2H)-yl}-N-hydroxy-2-methyl-2-(methylsulfonyl)butanamide | 0.000328 | >64.0 | 0.25 | 0.25 | 1 |
| 43 | (2R)-4-[5-fluoro-4-(4-methylphenyl)-2-oxopyridin-1(2H)-yl]-N-hydroxy-2-methyl-2-(methylsulfonyl)butanamide-d_3_ | 0.000653 | >64.0 | 0.25 | 1 | 0.5 |
| 44 | (2R)-4-[5-fluoro-4-(4-methoxyphenyl)-2-oxopyridin-1(2H)-yl]-N-hydroxy-2-methyl-2-(methylsulfonyl)butanamide-d_3_ | 0.000664 | >64.0 | 0.25 | 1 | 0.25 |
| 45 | (2R)-4-[4-(4-ethoxyphenyl)-5-fluoro-2-oxopyridin-1(2H)-yl]-N-hydroxy-2-methyl-2-(methylsulfonyl)butanamide-d_5_ | 0.000547 | >64.0 | 0.125 | 0.5 | 0.5 |
| 46 | (2R)-4-{4-[4-(cyclopropyloxy)phenyl]-5-fluoro-2-oxopyridin-1(2H)-yl}-N-hydroxy-2-methyl-2-(methylsulfonyl)butanamide | 0.000229 | >64.0 | 0.125 | 0.5 | 0.5 |
| 47 | (2R)-4-[4-(2,2-difluoro-1,3-benzodioxol-5-yl)-5-fluoro-2-oxopyridin-1(2H)-yl]-N-hydroxy-2-methyl-2-(methylsulfonyl)butanamide | | >64.0 | 0.25 | 1 | 0.5 |
| 48 | (2R)-4-[5-fluoro-2-oxo-4-(phenylethynyl)pyridin-1(2H)-yl]-N-hydroxy-2-methyl-2-(methylsulfonyl)butanamide | 0.000555 | >64.0 | 0.06 | 0.25 | 0.5 |
| 49 | (2R)-4-{5-Fluoro-2-oxo-4-[3-(1,3-thiazol-2-yloxy)phenyl]pyridin-1(2H)-yl}-N-hydroxy-2-methyl-2-(methylsulfonyl)butanamide | 0.000758 | >64 | 0.25 | 1 | 2 |

Examples 50 to 125

The compounds named below can be made following the general procedures outlined in Examples 1-49 above. Products are typically derived from a Suzuki-Miyaura cross coupling, as described above utilizing the appropriate starting materials, with optional deprotection of a terminal hydroxamic acid protecting group. Methods used to describe the synthesis of the precursors or coupling partners such as boronic acids or esters are known to those skilled in the art.

In Table 3 below, column 1 corresponds to the Example number, column 2 provides the IUPAC name, columns 3-6 provide in vitro biological data generated in the same manner as in Table 2, columns 7 and 8 provide the retention times and mass spectra generated via LCMS, using the method described below. All data is not currently available for all compounds, as indicated by a blank cell in Table 3.

The LCMS retention times reported in column 7 were generated in the following manner:

Gradient:

0.05% TFA 95:5 to 5:95 Water:ACN

Flow rate: 1.3 mL/min

Column dimensions: Acquity HPLC BEH C18 1.7 μm 2.1×30 mm.

Run time: 1.1 minutes

TABLE 3

| Example Number | IUPAC NAME | PA:IC50 (μM) | AB-3167 (μg/mL) | EC-1 (μg/mL) | PA:UC12120 (μg/mL) | Retention Time | Mass |
|---|---|---|---|---|---|---|---|
| 50 | 4-[5-fluoro-2-oxo-4-(3-oxo-2,3-dihydro-1H-isoindol-5-yl)pyridin-1(2H)-yl]-N-hydroxy-2-methyl-2-(methylsulfonyl)butanamide | 0.0682 | >64.0 | >64.0 | >64.0 | 0.42 | 438.1 |
| 51 | 4-[5-fluoro-4-(1H-indazol-6-yl)-2-oxopyridin-1(2H)-yl]-N-hydroxy-2-methyl-2-(methylsulfonyl)butanamide | 0.0039 | >64.0 | >64.0 | >64.0 | 0.49 | 423.1 |
| 52 | 2-fluoro-4-{5-fluoro-1-[4-(hydroxyamino)-3-methyl-3-(methylsulfonyl)-4-oxobutyl]-2-oxo-1,2-dihydropyridin-4-yl}-N-methylbenzamide | 0.0022 | >64.0 | 64 | 32 | 0.45 | 458.1 |
| 53 | 4-[5-fluoro-4-(4-hydroxyphenyl)-2-oxopyridin-1(2H)-yl]-N-hydroxy-2-methyl-2-(methylsulfonyl)butanamide | 0.0042 | >64.0 | >64.0 | 64 | 0.46 | 399 |
| 54 | 4-[4-(2,5-dimethoxyphenyl)-5-fluoro-2-oxopyridin-1(2H)-yl]-N-hydroxy-2-methyl-2-(methylsulfonyl)butanamide | >0.100 | >64.0 | >64.0 | >64.0 | 0.58 | 443.1 |
| 55 | 4-(5,5'-difluoro-2'-oxo-3,4'-bipyridin-1'(2'H)-yl)-N-hydroxy-2-methyl-2-(methylsulfonyl)butanamide | 0.0668 | >64.0 | >64.0 | 64 | | |
| 56 | 4-[4-(3-chloro-5-fluorophenyl)-5-fluoro-2-oxopyridin-1(2H)-yl]-N-hydroxy-2-methyl-2-(methylsulfonyl)butanamide | 0.0020 | >64.0 | 8 | 2 | | |
| 57 | 4-[5-fluoro-4-(2-methyl-3-oxo-2,3-dihydro-1H-isoindol-5-yl)-2-oxopyridin-1(2H)-yl]-N-hydroxy-2-methyl-2-(methylsulfonyl)butanamide | 0.0210 | >64.0 | >64.0 | >64.0 | 0.46 | 452.1 |
| 58 | 4-[4-(4-cyano-3-fluorophenyl)-5-fluoro-2-oxopyridin-1(2H)-yl]-N-hydroxy-2-methyl-2-(methylsulfonyl)butanamide | 0.0026 | >64.0 | 32 | 8 | | |
| 59 | 4-[5-fluoro-4-(4-methoxyphenyl)-2-oxopyridin-1(2H)-yl]-N-hydroxy-2-methyl-2-(methylsulfonyl)butanamide | 0.0010 | >64.0 | 1 | 1 | | |
| 60 | 4-{4-[4-(1-cyano-1-methylethyl)phenyl]-5-fluoro-2-oxopyridin-1(2H)-yl}-N-hydroxy-2-methyl-2-(methylsulfonyl)butanamide | 0.0039 | >64.0 | 32 | 4 | 0.61 | 450.1 |
| 61 | 4-[4-(3-acetamidophenyl)-5-fluoro-2-oxopyridin-1(2H)-yl]-N-hydroxy-2-methyl-2-(methylsulfonyl)butanamide | >0.100 | >64.0 | >64.0 | >64.0 | 0.47 | 440.1 |
| 62 | 4-[4-(3,5-difluoro-4-methoxyphenyl)-5-fluoro-2-oxopyridin-1(2H)-yl]-N-hydroxy-2-methyl-2-(methylsulfonyl)butanamide | 0.0020 | >64.0 | 4 | 2 | 0.62 | 449 |
| 62 | 4-[4-(3,5-difluorophenyl)-5-fluoro-2-oxopyridin-1(2H)-yl]-N-hydroxy-2-methyl-2-(methylsulfonyl)butanamide | 0.0031 | >64.0 | 8 | 1 | 0.61 | 419 |
| 64 | 4-[5-fluoro-4-(2-methyl-1-oxo-2,3-dihydro-1H-isoindol-5-yl)-2-oxopyridin-1(2H)-yl]-N-hydroxy-2-methyl-2-(methylsulfonyl)butanamide | 0.0072 | >64.0 | >64.0 | 64 | 0.44 | 452.1 |
| 65 | 4-(5'-fluoro-2'-oxo-3,4'-bipyridin-1'(2'H)-yl)-N-hydroxy-2-methyl-2-(methylsulfonyl)butanamide | 0.0823 | >64.0 | >64.0 | 32 | 0.31 | 384.1 |
| 66 | 4-[4-(4-chloro-2-fluorophenyl)-5-fluoro-2-oxopyridin-1(2H)-yl]-N-hydroxy-2-methyl-2-(methylsulfonyl)butanamide | 0.0008 | 64 | 0.5 | 0.5 | | |
| 67 | 4-[5-fluoro-4-(4-fluoro-3-methoxyphenyl)-2-oxopyridin-1(2H)-yl]-N-hydroxy-2-methyl-2-(methylsulfonyl)butanamide | 0.0045 | 64 | 16 | 4 | 0.59 | 431 |

TABLE 3-continued

| Example Number | IUPAC NAME | PA:IC50 (μM) | AB-3167 (μg/mL) | EC-1 (μg/mL) | PA:UC12120 (μg/mL) | Retention Time | Mass |
|---|---|---|---|---|---|---|---|
| 68 | 4-{5-fluoro-1-[4-(hydroxyamino)-3-methyl-3-(methylsulfonyl)-4-oxobutyl]-2-oxo-1,2-dihydropyridin-4-yl}-N,N-dimethylbenzamide | 0.0343 | >64.0 | >64.0 | >64.0 | 0.46 | 454.1 |
| 69 | 4-(5'-fluoro-2-methoxy-2'-oxo-3,4'-bipyridin-1'(2'H)-yl)-N-hydroxy-2-methyl-2-(methylsulfonyl)butanamide | 0.0166 | >64.0 | 64 | 8 | | |
| 70 | 4-(6-cyano-5'-fluoro-2'-oxo-3,4'-bipyridin-1'(2'H)-yl)-N-hydroxy-2-methyl-2-(methylsulfonyl)butanamide | 0.0333 | >64.0 | >64.0 | 64 | 0.47 | 409 |
| 71 | 4-[5-fluoro-4-(3-methyl-3H-imidazo[4,5-b]pyridin-6-yl)-2-oxopyridin-1(2H)-yl]-N-hydroxy-2-methyl-2-(methylsulfonyl)butanamide | >0.100 | >64.0 | >64.0 | >64.0 | 0.37 | 438.1 |
| 72 | 4-(5-fluoro-4-furo[3,2-b]pyridin-6-yl-2-oxopyridin-1(2H)-yl)-N-hydroxy-2-methyl-2-(methylsulfonyl)butanamide | 0.0348 | >64.0 | 64 | 32 | 0.44 | 424 |
| 73 | 4-(3',5-difluoro-2-oxo-4,4'-bipyridin-1(2H)-yl)-N-hydroxy-2-methyl-2-(methylsulfonyl)butanamide | 0.0083 | >64.0 | >64.0 | 8 | 0.43 | 402 |
| 74 | 4-[4-(4-cyano-3-methoxyphenyl)-5-fluoro-2-oxopyridin-1(2H)-yl]-N-hydroxy-2-methyl-2-(methylsulfonyl)butanamide | 0.0059 | >64.0 | 64 | 16 | | |
| 75 | 4-(5'-fluoro-5,6-dimethoxy-2'-oxo-3,4'-bipyridin-1'(2'H)-yl)-N-hydroxy-2-methyl-2-(methylsulfonyl)butanamide | 0.0454 | >64.0 | >64.0 | >64.0 | 0.51 | 444.1 |
| 76 | 4-[4-(4-ethoxyphenyl)-5-fluoro-2-oxopyridin-1(2H)-yl]-N-hydroxy-2-methyl-2-(methylsulfonyl)butanamide | 0.0011 | >64.0 | 0.25 | 0.5 | 0.63 | 427.1 |
| 77 | 4-{4-[4-(2-cyanoethyl)phenyl]-5-fluoro-2-oxopyridin-1(2H)-yl}-N-hydroxy-2-methyl-2-(methylsulfonyl)butanamide | 0.0026 | >64.0 | 32 | 4 | 0.54 | 436.1 |
| 78 | 4-(5-fluoro-2-oxo-4-phenylpyridin-1(2H)-yl)-N-hydroxy-2-methyl-2-(methylsulfonyl)butanamide | 0.0028 | >64.0 | 4 | 1 | 0.57 | 383.1 |
| 79 | 4-[4-{4-[(dimethylamino)methyl]phenyl}-5-fluoro-2-oxopyridin-1(2H)-yl]-N-hydroxy-2-methyl-2-(methylsulfonyl)butanamide | 0.0359 | >64.0 | >64.0 | 16 | 0.37 | 440.1 |
| 80 | 4-(5'-fluoro-6-hydroxy-2'-oxo-3,4'-bipyridin-1'(2'H)-yl)-N-hydroxy-2-methyl-2-(methylsulfonyl)butanamide | >0.100 | >64.0 | >64.0 | >64.0 | 0.35 | 400 |
| 81 | 4-[4-(4-acetamidophenyl)-5-fluoro-2-oxopyridin-1(2H)-yl]-N-hydroxy-2-methyl-2-(methylsulfonyl)butanamide | 0.0243 | >64.0 | 64 | 32 | 0.45 | 440.1 |
| 82 | 4-[4-(3-cyanophenyl)-5-fluoro-2-oxopyridin-1(2H)-yl]-N-hydroxy-2-methyl-2-(methylsulfonyl)butanamide | 0.0130 | >64.0 | 64 | 8 | | |
| 83 | 4-(5,5'-difluoro-6-methyl-2'-oxo-3,4'-bipyridin-1'(2'H)-yl)-N-hydroxy-2-methyl-2-(methylsulfonyl)butanamide | 0.0275 | >64.0 | >64.0 | 32 | 0.49 | 416.1 |
| 84 | 4-{5-fluoro-1-[4-(hydroxyamino)-3-methyl-3-(methylsulfonyl)-4-oxobutyl]-2-oxo-1,2-dihydropyridin-4-yl}-N-methylbenzamide | 0.0145 | >64.0 | >64.0 | >64.0 | 0.43 | 440.1 |
| 85 | 4-[5'-fluoro-6-(hydroxymethyl)-2'-oxo-3,4'-bipyridin-1'(2'H)-yl]-N-hydroxy-2-methyl-2-(methylsulfonyl)butanamide | >0.100 | >64.0 | >64.0 | >64.0 | 0.32 | 414.1 |

TABLE 3-continued

| Example Number | IUPAC NAME | PA:IC50 (µM) | AB-3167 (µg/mL) | EC-1 (µg/mL) | PA:UC12120 (µg/mL) | Retention Time | Mass |
|---|---|---|---|---|---|---|---|
| 86 | 4-[5-fluoro-4-(4-fluorophenyl)-2-oxopyridin-1(2H)-yl]-N-hydroxy-2-methyl-2-(methylsulfonyl)butanamide | 0.0017 | >64.0 | 4 | 1 | | |
| 87 | 4-(5-fluoro-2-oxo-4-quinolin-3-ylpyridin-1(2H)-yl)-N-hydroxy-2-methyl-2-(methylsulfonyl)butanamide | 0.0061 | >64.0 | 16 | 8 | 0.46 | 434.1 |
| 88 | 4-{5-fluoro-4-[4-(1-methoxyethyl)phenyl]-2-oxopyridin-1(2H)-yl}-N-hydroxy-2-methyl-2-(methylsulfonyl)butanamide | 0.0076 | >64.0 | 16 | 4 | 0.59 | 441.1 |
| 89 | 4-(5'-fluoro-6-methoxy-2'-oxo-3,4'-bipyridin-1'(2'H)-yl)-N-hydroxy-2-methyl-2-(methylsulfonyl)butanamide | 0.0031 | >64.0 | 8 | 2 | | |
| 90 | 4-(5-chloro-5'-fluoro-2'-oxo-2,4'-bipyridin-1'(2'H)-yl)-N-hydroxy-2-methyl-2-(methylsulfonyl)butanamide | 0.0125 | >64.0 | 64 | 16 | | |
| 91 | 4-{4-[4-(cyanomethyl)phenyl]-5-fluoro-2-oxopyridin-1(2H)-yl}-N-hydroxy-2-methyl-2-(methylsulfonyl)butanamide | 0.0023 | >64.0 | 16 | 4 | 0.52 | 422.1 |
| 92 | 4-(2'-ethoxy-5-fluoro-2-oxo-4,4'-bipyridin-1(2H)-yl)-N-hydroxy-2-methyl-2-(methylsulfonyl)butanamide | 0.0057 | >64.0 | 8 | 8 | 0.54 | 428.1 |
| 93 | 4-{5-fluoro-4-[3-(methoxymethyl)phenyl]-2-oxopyridin-1(2H)-yl}-N-hydroxy-2-methyl-2-(methylsulfonyl)butanamide | 0.0142 | >64.0 | 32 | 8 | | |
| 94 | 4-[4-(2-cyanophenyl)-5-fluoro-2-oxopyridin-1(2H)-yl]-N-hydroxy-2-methyl-2-(methylsulfonyl)butanamide | 0.0323 | 32 | 8 | 32 | 0.52 | 408 |
| 95 | 4-[4-(4-ethoxy-3-fluorophenyl)-5-fluoro-2-oxopyridin-1(2H)-yl]-N-hydroxy-2-methyl-2-(methylsulfonyl)butanamide | 0.0012 | 64 | 1 | 2 | 0.63 | 445.1 |
| 96 | 4-[5-fluoro-4-(2-methylquinolin-7-yl)-2-oxopyridin-1(2H)-yl]-N-hydroxy-2-methyl-2-(methylsulfonyl)butanamide | 0.0108 | >64.0 | 16 | 32 | 0.39 | 448.1 |
| 97 | 4-[4-(2,4-difluorophenyl)-5-fluoro-2-oxopyridin-1(2H)-yl]-N-hydroxy-2-methyl-2-(methylsulfonyl)butanamide | 0.0012 | >64.0 | 4 | 1 | 0.59 | 419 |
| 98 | 4-[4-(3,4-dimethoxyphenyl)-5-fluoro-2-oxopyridin-1(2H)-yl]-N-hydroxy-2-methyl-2-(methylsulfonyl)butanamide | 0.0285 | >64.0 | 64 | 32 | 0.53 | 443.1 |
| 99 | 4-(6-ethoxy-5'-fluoro-2'-oxo-3,4'-bipyridin-1'(2'H)-yl)-N-hydroxy-2-methyl-2-(methylsulfonyl)butanamide | 0.0025 | >64.0 | 2 | 2 | | |
| 100 | 4-[5-fluoro-4-(3-methoxyphenyl)-2-oxopyridin-1(2H)-yl]-N-hydroxy-2-methyl-2-(methylsulfonyl)butanamide | 0.0025 | >64.0 | 4 | 2 | 0.58 | 413.1 |
| 101 | 4-[4-(4-cyano-2-methoxyphenyl)-5-fluoro-2-oxopyridin-1(2H)-yl]-N-hydroxy-2-methyl-2-(methylsulfonyl)butanamide | 0.0052 | >64.0 | 64 | 8 | 0.55 | 438.1 |
| 102 | 4-[4-(4-chloro-3-cyanophenyl)-5-fluoro-2-oxopyridin-1(2H)-yl]-N-hydroxy-2-methyl-2-(methylsulfonyl)butanamide | 0.0021 | >64.0 | 4 | 4 | 0.6 | 442 |
| 103 | 4-[5-fluoro-4-(2-fluorophenyl)-2-oxopyridin-1(2H)-yl]-N-hydroxy-2-methyl-2-(methylsulfonyl)butanamide | 0.0014 | >64.0 | 4 | 0.5 | 0.57 | 401.1 |
| 104 | 4-(5'-fluoro-2-isopropoxy-2'-oxo-3,4'-bipyridin-1'(2'H)-yl)-N- | >0.100 | 32 | 8 | 32 | | |

TABLE 3-continued

| Example Number | IUPAC NAME | PA:IC50 (µM) | AB-3167 (µg/mL) | EC-1 (µg/mL) | PA:UC12120 (µg/mL) | Retention Time | Mass |
|---|---|---|---|---|---|---|---|
| | hydroxy-2-methyl-2-(methylsulfonyl)butanamide | | | | | | |
| 105 | 4-{5-fluoro-4-[4-fluoro-3-(hydroxymethyl)phenyl]-2-oxopyridin-1(2H)-yl}-N-hydroxy-2-methyl-2-(methylsulfonyl)butanamide | | >64.0 | >64.0 | >64.0 | 0.49 | 431.1 |
| 106 | 4-[5-fluoro-2-oxo-4-(2-pyrrolidin-1-ylpyrimidin-5-yl)pyridin-1(2H)-yl]-N-hydroxy-2-methyl-2-(methylsulfonyl)butanamide | 0.0568 | >64.0 | 32 | 64 | 0.5 | 454.1 |
| 107 | 4-[4-(4-chlorophenyl)-5-fluoro-2-oxopyridin-1(2H)-yl]-N-hydroxy-2-methyl-2-(methylsulfonyl)butanamide | 0.0010 | >64.0 | 1 | 0.25 | 0.64 | 417 |
| 108 | 4-[5-fluoro-2-oxo-4-(1-oxo-2,3-dihydro-1H-isoindol-5-yl)pyridin-1(2H)-yl]-N-hydroxy-2-methyl-2-(methylsulfonyl)butanamide | 0.0072 | >64.0 | >64.0 | >64.0 | 0.4 | 438.1 |
| 109 | 4-[4-(4-chloro-3-hydroxyphenyl)-5-fluoro-2-oxopyridin-1(2H)-yl]-N-hydroxy-2-methyl-2-(methylsulfonyl)butanamide | 0.0073 | >64.0 | 32 | 32 | 0.56 | 433 |
| 110 | 4-{5-fluoro-4-[2-(methoxymethyl)phenyl]-2-oxopyridin-1(2H)-yl}-N-hydroxy-2-methyl-2-(methylsulfonyl)butanamide | >0.100 | >64.0 | >64.0 | >64.0 | 0.56 | 427.1 |
| 111 | 4-[5-fluoro-4-(2-fluoro-3-methoxy-5-methylphenyl)-2-oxopyridin-1(2H)-yl]-N-hydroxy-2-methyl-2-(methylsulfonyl)butanamide | 0.0030 | >64.0 | 4 | 4 | 0.61 | 445.1 |
| 112 | 4-[4-(3-ethoxyphenyl)-5-fluoro-2-oxopyridin-1(2H)-yl]-N-hydroxy-2-methyl-2-(methylsulfonyl)butanamide | 0.0031 | >64.0 | 2 | 4 | | |
| 113 | 4-[5'-fluoro-2'-oxo-6-(trifluoromethyl)-3,4'-bipyridin-1'(2'H)-yl]-N-hydroxy-2-methyl-2-(methylsulfonyl)butanamide | 0.0296 | >64.0 | >64.0 | 32 | 0.58 | 452 |
| 114 | 4-[4-(4-cyano-3-methylphenyl)-5-fluoro-2-oxopyridin-1(2H)-yl]-N-hydroxy-2-methyl-2-(methylsulfonyl)butanamide | 0.0013 | >64.0 | 4 | 2 | 0.57 | 422.1 |
| 115 | 4-{4-[2-(dimethylamino)pyrimidin-5-yl]-5-fluoro-2-oxopyridin-1(2H)-yl}-N-hydroxy-2-methyl-2-(methylsulfonyl)butanamide | 0.0741 | >64.0 | 32 | 32 | 0.48 | 428.1 |
| 116 | 4-[5-fluoro-4-(3-fluorophenyl)-2-oxopyridin-1(2H)-yl]-N-hydroxy-2-methyl-2-(methylsulfonyl)butanamide | 0.0010 | >64.0 | 4 | 1 | 0.58 | 401.1 |
| 117 | 4-[4-(2,3-difluorophenyl)-5-fluoro-2-oxopyridin-1(2H)-yl]-N-hydroxy-2-methyl-2-(methylsulfonyl)butanamide | 0.0008 | >64.0 | 2 | 0.5 | 0.59 | 419.1 |
| 118 | 4-[5-fluoro-4-(2-fluoro-3-methoxyphenyl)-2-oxopyridin-1(2H)-yl]-N-hydroxy-2-methyl-2-(methylsulfonyl)butanamide | 0.0007 | >64.0 | 1 | 1 | 0.57 | 431.1 |
| 119 | 4-[4-(3-cyano-5-methoxyphenyl)-5-fluoro-2-oxopyridin-1(2H)-yl]-N-hydroxy-2-methyl-2-(methylsulfonyl)butanamide | 0.0508 | >64.0 | >64.0 | 64 | 0.57 | 438.1 |
| 120 | 4-[4-(2,3-dihydro-1-benzofuran-5-yl)-5-fluoro-2-oxopyridin-1(2H)-yl]-N-hydroxy-2-methyl-2-(methylsulfonyl)butanamide | 0.0009 | >64.0 | 2 | 1 | 0.57 | 425.1 |
| 121 | 4-[5-fluoro-2-oxo-4-(1H-pyrazol-3-yl)pyridin-1(2H)-yl]-N-hydroxy-2-methyl-2-(methylsulfonyl)butanamide | | >64.0 | >64.0 | >64.0 | | |

TABLE 3-continued

| Example Number | IUPAC NAME | PA:IC50 (µM) | AB-3167 (µg/mL) | EC-1 (µg/mL) | PA:UC12120 (µg/mL) | Retention Time | Mass |
|---|---|---|---|---|---|---|---|
| 122 | 4-{5-fluoro-4-[2-fluoro-3-(hydroxymethyl)phenyl]-2-oxopyridin-1(2H)-yl}-N-hydroxy-2-methyl-2-(methylsulfonyl)butanamide | 0.0024 | | | | 0.46 | 431.1 |
| 123 | 4-{4-[3-(2-amino-2-oxoethyl)phenyl]-5-fluoro-2-oxopyridin-1(2H)-yl}-N-hydroxy-2-methyl-2-(methylsulfonyl)butanamide | | >64.0 | >64.0 | >64.0 | 0.43 | 440.1 |
| 124 | 4-[4-(4-cyanophenyl)-5-fluoro-2-oxopyridin-1(2H)-yl]-N-hydroxy-2-methyl-2-(methylsulfonyl)butanamide | 0.0034 | >64.0 | 32 | 8 | 0.53 | 408 |
| 125 | 4-[5-fluoro-4-(2-methoxyphenyl)-2-oxopyridin-1(2H)-yl]-N-hydroxy-2-methyl-2-(methylsulfonyl)butanamide | 0.0129 | >64.0 | 64 | 8 | 0.57 | 413.1 |

What is claimed is:

1. A compound of the formula Ia

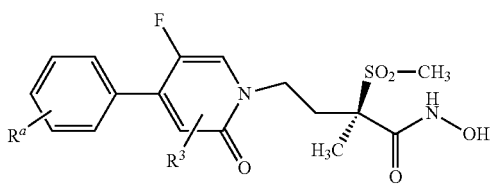

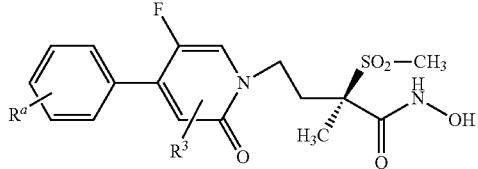

or a pharmaceutically acceptable salt thereof,
in which;

$R^3$ is represented by hydrogen, halogen, hydroxy, cyano, $C_1$-$C_3$alkyl, $C_1$-$C_3$alkoxy, trifluoromethyl or trifluoromethoxy;

$R^a$ is represented by one or more substituents selected from the group consisting of $C_1$-$C_3$alkyl, $C_1$-$C_3$ alkoxy, fluorine, chlorine, hydroxy, trifluoromethyl and trifluoromethoxy.

2. The compound (2R)-4-[5-Fluoro-4-(2-fluoro-4-methoxyphenyl)-2-oxopyridin-1(2H)-yl]-N-hydroxy-2-methyl-2-(methylsulfonyl)butanamide, or a pharmaceutically acceptable salt thereof.

3. A pharmaceutical composition comprising a therapeutically effective amount of a compound, or a pharmaceutically acceptable salt thereof according to claim 1 in admixture with at least one pharmaceutically acceptable excipient.

4. A method for treating a Gram-negative bacterial infection in a patient, the method comprising administering a therapeutically effective amount of a compound according to claim 1 to a patient in need of treatment thereof.

5. A pharmaceutical composition comprising a therapeutically effective amount of (2R)-4-[5-Fluoro-4-(2-fluoro-4-methoxyphenyl)-2-oxopyridin-1(2H)-yl]-N-hydroxy-2-methyl-2-(methylsulfonyl)butanamide, or a pharmaceutically acceptable salt thereof in admixture with at least one pharmaceutically acceptable excipient.

6. A method for treating a Gram-negative bacterial infection in a patient, the method comprising administering a therapeutically effective amount of (2R)-4-[5-Fluoro-4-(2-fluoro-4-methoxyphenyl)-2-oxopyridin-1(2H)-yl]-N-hydroxy-2-methyl-2-(methylsulfonyl)butanamide, or a pharmaceutically acceptable salt thereof to a patient in need of treatment thereof.

7. A method for treating a Gram-negative bacterial infection in a patient, the method comprising contacting the bacteria in said patient with a therapeutically effective amount of a compound of the formula Ia or a pharmaceutically acceptable salt thereof,
in which;

$R^3$ is represented by hydrogen, halogen, hydroxy, cyano, $C_1$-$C_3$alkyl, $C_1$-$C_3$alkoxy, trifluoromethyl or trifluoromethoxy;

$R^a$ is represented by one or more substituents selected from the group consisting of $C_1$-$C_3$alkyl, $C_1$-$C_3$ alkoxy, fluorine, chlorine, hydroxy, trifluoromethyl and trifluoromethoxy.

8. A method of treating a Gram-negative bacterial infection in a patient, the method comprising contacting the bacteria in said patient with a therapeutically effective amount of (2R)-4-[5-Fluoro-4-(2-fluoro-4-methoxyphenyl)-2-oxopyridin-1 (2H)-yl]-N-hydroxy-2-methyl-2-(methylsulfonyl)butanamide, or a pharmaceutically acceptable salt thereof.

9. The method according to claim 8 wherein the compound is (2R)-4-[5-Fluoro-4-(2-fluoro-4-methoxyphenyl)-2-oxopyridin-1(2H)-yl]-N-hydroxy-2-methyl-2-(methylsulfonyl)butanamide.

10. The method according to claim 8 wherein the Gram-negative bacterial infection is caused by a Gram-negative bacteria selected from the group consisting of *Acinetobacter baumannii*, *Acinetobacter spp.*, *Citrobacter spp.*, *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia*, and *Pseudomonas aeruginosa*.

11. The method according to claim 8 wherein the Gram-negative bacterial infection is selected from the group consisting of nosocomial pneumonia, urinary tract infection, bacteremia, sepsis, skin infection, soft-tissue infection, intraabdominal infection, lung infection, endocarditis, diabetic foot infection, osteomyelitis and central nervous system infection.

* * * * *